United States Patent
Liu

(10) Patent No.: US 10,406,250 B2
(45) Date of Patent: Sep. 10, 2019

(54) SUICIDE CONTRAST AGENTS TARGETING HIV RESERVOIRS FOR THERANOSTIC ERADICATION

(71) Applicant: The General Hospital Corporation, Boston, MA (US)

(72) Inventor: Philip K. Liu, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 134 days.

(21) Appl. No.: 15/036,512

(22) PCT Filed: Nov. 14, 2014

(86) PCT No.: PCT/US2014/065613
§ 371 (c)(1),
(2) Date: May 13, 2016

(87) PCT Pub. No.: WO2015/073773
PCT Pub. Date: May 21, 2015

(65) Prior Publication Data
US 2016/0263253 A1    Sep. 15, 2016

Related U.S. Application Data

(60) Provisional application No. 61/904,238, filed on Nov. 14, 2013.

(51) Int. Cl.
| | |
|---|---|
| *A61B 5/055* | (2006.01) |
| *A61K 49/12* | (2006.01) |
| *A61K 49/00* | (2006.01) |
| *A61K 49/18* | (2006.01) |
| *C12Q 1/68* | (2018.01) |
| *C12N 15/113* | (2010.01) |
| *A61K 47/69* | (2017.01) |

(52) U.S. Cl.
CPC ........ *A61K 49/126* (2013.01); *A61K 47/6923* (2017.08); *A61K 49/0002* (2013.01); *A61K 49/0032* (2013.01); *A61K 49/0093* (2013.01); *A61K 49/1833* (2013.01); *A61K 49/1866* (2013.01); *A61K 49/1872* (2013.01); *C12N 15/113* (2013.01); *C12Q 1/68* (2013.01); *C12N 2310/11* (2013.01); *C12N 2310/315* (2013.01); *C12N 2310/3517* (2013.01); *C12N 2310/3519* (2013.01); *C12N 2320/32* (2013.01)

(58) Field of Classification Search
CPC .. A61K 49/00; A61K 49/126; A61K 49/1872; A61K 49/0002; A61K 49/1866; A61K 49/0093; A61K 49/0032; A61K 47/00; A61K 47/6923; A61K 49/1833; C12N 15/113; C12N 2320/32; C12N 2310/3517; C12N 2310/315; C12N 2310/3519; C12N 2310/11; C12Q 1/68
USPC .... 424/1.11, 1.65, 1.73, 1.77, 1.81, 9.1, 9.2, 424/9.3, 9.32, 9.322, 9.323, 9.34, 9.341, 424/9.35, 9.351, 9.36
See application file for complete search history.

(56) References Cited

U.S. PATENT DOCUMENTS

| | | | |
|---|---|---|---|
| 5,629,413 A | | 5/1997 | Peterson et al. |
| 8,268,982 B2 | * | 9/2012 | Mitsuhashi ............ C12Q 1/686 435/183 |
| 2008/0311155 A1 | | 12/2008 | Nicolette et al. |
| 2010/0120022 A1 | | 5/2010 | Ayalon-Soffer et al. |
| 2010/0239504 A1 | | 9/2010 | Liu et al. |
| 2010/0310473 A1 | * | 12/2010 | Liu ...................... A61K 9/0048 424/9.323 |
| 2011/0129421 A1 | * | 6/2011 | Liu .................... A61K 49/1866 424/9.1 |

FOREIGN PATENT DOCUMENTS

EP    0617132 A2    9/1994

OTHER PUBLICATIONS

Messam et al "Stages of Restricted HIV-1 Infection in Astrocyte Cultures Derived from Human Fetal Brain Tissue" Journal of NeuroVirology vol. 6, pp. S90-S94, 2000.
Thompson et al "Brain Cell Reservoirs of Latent Virus in Presymptomatic HIV-Infected Individuals" The American Journal of Pathology vol. 179, pp. 1623-1629, 2011.

* cited by examiner

*Primary Examiner* — D. L. Jones
(74) *Attorney, Agent, or Firm* — Cesari and McKenna, LLP

(57) ABSTRACT

We have developed a model system of HIV reservoirs in neural cells by generating chimeric phosphorothioate-modified oligodeoxynucleotides (sODN) that specifically interact with neural cell DNA or RNA, and that further comprise a sequence of the HIV genome. In particular, we have conjugated the chimera sODN to a delivery vehicle (e.g. a superparamagnetic iron oxide nanoparticle (SPIO)) and have demonstrated specific delivery to neural cells, in vitro and in vivo. These model systems can be used to screen for agents that specifically target latent viral infection. In particular, using the model system, we have developed suicide MRI contrast agents that can be used to reduce the number of neural cells which harbor the virus, also provided herein. Our model system is translatable to other latent viruses as well.

14 Claims, 18 Drawing Sheets
Specification includes a Sequence Listing.

SPECIFIC UPTAKE OF SPION-fos BUT NOT SPION-gfap IN Fos+/GFA- NEURONS IN NORMAL AND RESTING MOUSE BRAINS NEURONS WITH Fos ANTIGEN MRI OF NEURONS BY SPION-cfos

GFAP NULL NEURONS

MRI OF gfap mRNA NEGATIVE NEURON BY SPION-gfap

MRI OF BACKGROUND (NO INFUSION) CONTROL AT THE DENTATE GYRUS (DG)

ARROWS: NEURONAL FORMATION IN THE DENTATE GYRUS (DG)

Figure 10
A. Temporal change in R2* maps (10-120 s⁻¹)

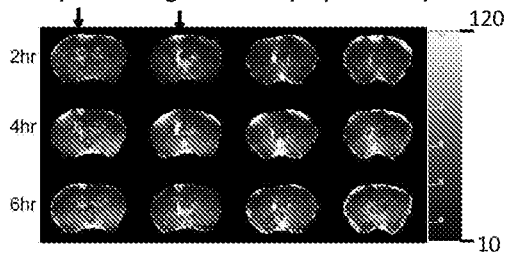

B. Outlines of Region of Interest

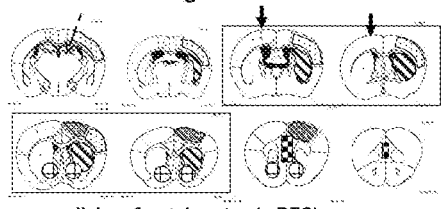

- medial prefrontal cortex (mPFC)
- Nucleus Accumbens (NAc)
- Caudate Putamen (CPu)
- Somatosensory cortex (SSC)
- Motor cortex (MC)
Arrows: ICV sites; dash arrow: hippocampus (HIPPO)

C. Temporal ΔR2* profiles in different brain regions at contralateral hemisphere

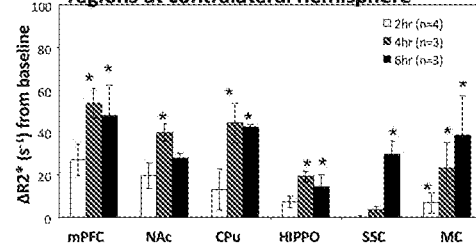

D. R2* contrast to Noise Ratio

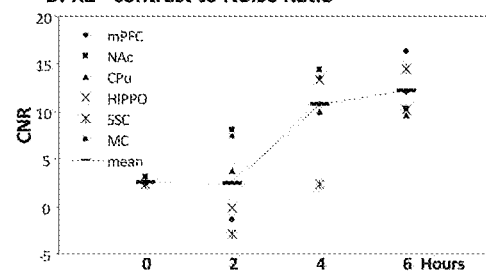

Figure 11

A. ΔR2* maps

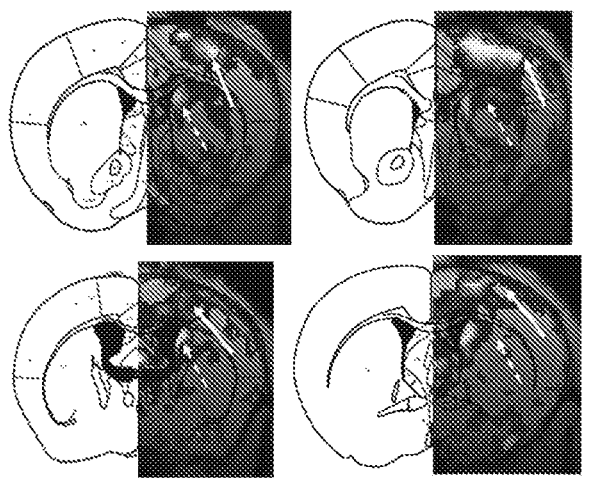

B. Ex vivo Mouse SVZ
NORMAL

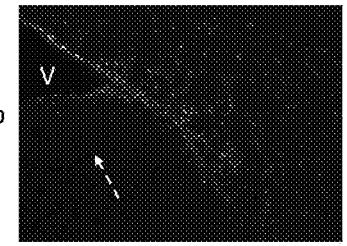

A8 SVZ K83

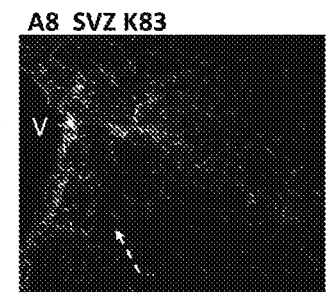

ΔR2* (POST − PRE BEACON)/PRE X 100%
I. HIV RESERVOIR (3 HR) + BEACON
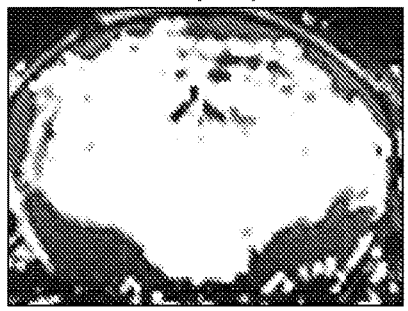 
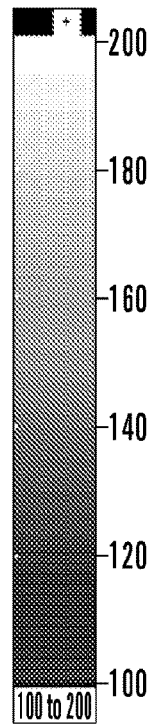
II. CONTROL RESERVOIR (3 HR) + BEACON
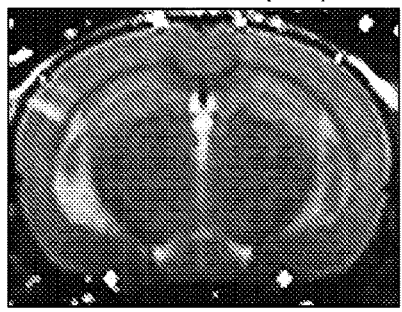 
HIV RESERVOIR = Cy3-[+]hiv-vif-ASgfap;
CONTROL = Cy3-[-]hiv-vif-ASgfap;
BEACON = SPION-[-]hiv-vif (MRI)
*FIG. 12D*

SEQUENCE LISTING

<160> NUMBER OF SEQ ID NOS: 57

<210> SEQ ID NO 1
<211> LENGTH: 20
<212> TYPE: DNA
<213> ORGANISM: Rattus norvegicus

```
<400> SEQUENCE: 1
tgatacgtct ccgctccatc                                              20

<210> SEQ ID NO 2
<211> LENGTH: 21
<212> TYPE: DNA
<213> ORGANISM: Mus musculus

<400> SEQUENCE: 2
tgtctccgct ccatcctgcc c                                            21

<210> SEQ ID NO 3
<211> LENGTH: 22
<212> TYPE: DNA
<213> ORGANISM: Homo sapiens

<400> SEQUENCE: 3
cgtcaagctc cacatggacc tg                                           22

<210> SEQ ID NO 4
<211> LENGTH: 20
<212> TYPE: DNA
<213> ORGANISM: Rattus norvegicus

<400> SEQUENCE: 4
gatggagcgg agacgtatca                                              20

<210> SEQ ID NO 5
<211> LENGTH: 21
<212> TYPE: DNA
<213> ORGANISM: Mus musculus

<400> SEQUENCE: 5
gggcaggatg gagcggagac a                                            21

<210> SEQ ID NO 6
<211> LENGTH: 22
<212> TYPE: DNA
<213> ORGANISM: Homo sapiens

<400> SEQUENCE: 6
caggtccatg tggagcttga cg                                           22

<210> SEQ ID NO 7
<211> LENGTH: 22
<212> TYPE: DNA
<213> ORGANISM: Homo sapiens

<400> SEQUENCE: 7
cgtcaagctc cacatggacc tg                                           22

<210> SEQ ID NO 8
<211> LENGTH: 22
<212> TYPE: DNA
<213> ORGANISM: Homo sapiens

<400> SEQUENCE: 8
caggtccatg tggagcttga cg                                           22

<210> SEQ ID NO 9
<211> LENGTH: 21
<212> TYPE: DNA
```

<213> ORGANISM: Human immunodeficiency virus

<400> SEQUENCE: 9
gtccttcctt gccacagttg a　　　　　　　　　　　　　　　　　　　　　21

<210> SEQ ID NO 10
<211> LENGTH: 21
<212> TYPE: DNA
<213> ORGANISM: Human immunodeficiency virus

<400> SEQUENCE: 10
ctactgcccc ttcacctttc c　　　　　　　　　　　　　　　　　　　　　21

<210> SEQ ID NO 11
<211> LENGTH: 20
<212> TYPE: DNA
<213> ORGANISM: Human immunodeficiency virus

<400> SEQUENCE: 11
tttctgctat gttggcaccc　　　　　　　　　　　　　　　　　　　　　　20

<210> SEQ ID NO 12
<211> LENGTH: 21
<212> TYPE: DNA
<213> ORGANISM: Human immunodeficiency virus

<400> SEQUENCE: 12
tactgtccta agccatggag c　　　　　　　　　　　　　　　　　　　　　21

<210> SEQ ID NO 13
<211> LENGTH: 21
<212> TYPE: DNA
<213> ORGANISM: Human immunodeficiency virus

<400> SEQUENCE: 13
atccacacaa ctatggctgc t　　　　　　　　　　　　　　　　　　　　　21

<210> SEQ ID NO 14
<211> LENGTH: 21
<212> TYPE: DNA
<213> ORGANISM: Human immunodeficiency virus

<400> SEQUENCE: 14
ccctaccaac tctttgccct a　　　　　　　　　　　　　　　　　　　　　21

<210> SEQ ID NO 15
<211> LENGTH: 21
<212> TYPE: DNA
<213> ORGANISM: Human immunodeficiency virus

<400> SEQUENCE: 15
ctggtccgtc tggttgttaa g　　　　　　　　　　　　　　　　　　　　　21

<210> SEQ ID NO 16
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 16
cctgaccagg cagaccacta attcatctac attattgata cgtctccgct ccatc　　　55

```
<210> SEQ ID NO 17
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 17
cctctggtcc gtctggttgt taagatctac attattgata cgtctccgct ccatc        55

<210> SEQ ID NO 18
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 18
cctgaccagg cagaccacta attcatctac attatgatgg agcggagacg tatca        55

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
gtctccgctc catcctgccc                                               20

<210> SEQ ID NO 20
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 20
cctgaccagg cagaccaact aattcatcta cattatgtct ccgctccatc ctgccc       56

<210> SEQ ID NO 21
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 21
cctctggtcc gtctggttga ttaagatcta cattatgtct ccgctccatc ctgccc       56

<210> SEQ ID NO 22
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 22
cctgaccagg cagaccaact aattcatcta cattattctg gcgccggtta cagaac       56

<210> SEQ ID NO 23
<211> LENGTH: 56
<212> TYPE: DNA
<213> ORGANISM: Artificial Sequence
<220> FEATURE:
<223> OTHER INFORMATION: Synthetic oligonucleotide
```

<400> SEQUENCE: 23
cctctggtcc gtctggttga ttaagatcta cattattctg gcgccggtta cagaac         56

<210> SEQ ID NO 24
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 24
atctacatta t                                                          11

<210> SEQ ID NO 25
<211> LENGTH: 3
<212> TYPE: DNA
<213> ORGANISM: Artificial Sequence
<220> FEATURE:
<223> OTHER INFORMATION: Synthetic oligonucleotide

<400> SEQUENCE: 25 cct                                                                    3

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 26
gggatcgttc agagtcta                                                   18

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 27
tagactctga acgatccc                                                   18

<210> SEQ ID NO 28
<211> LENGTH: 9719
<212> TYPE: DNA
<213> ORGANISM: Human immunodeficiency virus

<400> SEQUENCE: 28
tggaagggct aattcactcc caacgaagac aagatatcct tgatctgtgg atctaccaca     60
cacaaggcta cttccctgat tagcagaact acacaccagg gccagggatc agatatccac    120
tgacctttgg atggtgctac aagctagtac cagttgagcc agagaagtta gaagaagcca    180 acaaggaga gaacaccagc ttgttacacc ctgtgagcct gcatggaatg gatgacccgg     240
agagagaagt gttagagtgg aggtttgaca gccgcctagc atttcatcac atggcccgag    300
agctgcatcc ggagtacttc aagaactgct gacatcgagc ttgctacaag gactttccg    360 ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600

```
agaccctttt agtcagtgtg gaaaatctct agcagtggcg cccgaacagg gacctgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgatgggaa    840
aaaattcggt taaggccagg gggaagaaa aaatataaat taaaacatat agtatgggca    900
agcagggagc tagaacgatt cgcagttaat cctggcctgt tagaaacatc agaaggctgt    960
agacaaatac tgggacagct acaaccatcc cttcagacag gatcagaaga acttagatca   1020
ttatataata cagtagcaac cctctattgt gtgcatcaaa ggatagagat aaaagacacc   1080
aaggaagctt tagacaagat agaggaagag caaaacaaaa gtaagaaaaa agcacagcaa   1140
gcagcagctg acacaggaca cagcaatcag gtcagccaaa attaccctat agtgcagaac   1200
atccagggca aatggtaca tcaggccata tcacctagaa ctttaaatgc atgggtaaaa   1260
gtagtagaag agaaggcttt cagcccagaa gtgataccca tgttttcagc attatcagaa   1320
ggagccaccc cacaagattt aaacaccatg ctaaacacag tggggggaca tcaagcagcc   1380
atgcaaatgt taaaagagac catcaatgag gaagctgcag aatgggatag agtgcatcca   1440
gtgcatgcag ggcctattgc accaggccag atgagagaac caaggggaag tgacatagca   1500
ggaactacta gtacccttca ggaacaaata ggatggatga caataatcc acctatccca   1560 gtaggagaaa tttataaaag atggataatc ctgggattaa ataaaatagt aagaatgtat   1620
agccctacca gcattctgga cataagacaa ggaccaaagg aaccctttag agactatgta   1680
gaccggttct ataaaactct aagagccgag caagcttcac aggaggtaaa aaattggatg   1740
acagaaacct tgttggtcca aaatgcgaac ccagattgta agactatttt aaaagcattg   1800
ggaccagcgg ctacactaga agaaatgatg acagcatgtc agggagtagg aggacccggc   1860
cataaggcaa gagttttggc tgaagcaatg agccaagtaa caaattcagc taccataatg   1920
atgcagagag gcaattttag gaaccaaaga aagattgtta agtgtttcaa ttgtggcaaa   1980
gaagggcaca cagccagaaa ttgcagggcc cctaggaaaa agggctgttg gaaatgtgga   2040
aaggaaggac accaaatgaa agattgtact gagagacagg ctaattttt agggaagatc   2100 tggccttcct acaagggaag gccagggaat tttcttcaga gcagaccaga gccaacagcc   2160
ccaccagaag agagcttcag gtctggggta gagacaacaa ctccccctca gaagcaggag   2220
ccgatagaca aggaactgta tcctttaact tccctcaggt cactctttgg caacgacccc   2280
tcgtcacaat aaagataggg gggcaactaa aggaagctct attagataca ggagcagatg   2340
atacagtatt agaagaaatg agtttgccag gaagatggaa accaaaaatg atagggggaa   2400
ttggaggttt tatcaaagta agacagtatg atcagatact catagaaatc tgtggacata   2460
aagctatagg tacagtatta gtaggaccta cacctgtcaa cataattgga agaaatctgt   2520
tgactcagat tggttgcact ttaaattttc ccattagccc tattgagact gtaccagtaa   2580
aattaaagcc aggaatggat ggcccaaaag ttaaacaatg gccattgaca gaagaaaaaa   2640
taaaagcatt agtagaaatt tgtacagaga tggaaaagga agggaaaatt tcaaaaattg   2700
ggcctgaaaa tccatacaat actccagtat ttgccataaa gaaaaagac agtactaaat   2760 ggagaaaatt agtagatttc agagaactta ataagagaac tcaagacttc tgggaagttc   2820
aattaggaat accacatccc gcagggttaa aaagaaaaa atcagtaaca gtactggatg   2880
tgggtgatgc atatttttca gttcccttag atgaagactt caggaagtat actgcattta   2940
```

```
ccatacctag tataaacaat gagacaccag ggattagata tcagtacaat gtgcttccac      3000
agggatggaa aggatcacca gcaatattcc aaagtagcat gacaaaaatc ttagagcctt      3060
ttagaaaaca aaatccagac atagttatct atcaatacat ggatgatttg tatgtaggat      3120
ctgacttaga aatagggcag catagaacaa aaatagagga gctgagacaa catctgttga      3180
ggtggggact taccacacca gacaaaaaac atcagaaaga acctccattc ctttggatgg      3240
gttatgaact ccatcctgat aaatggacag tacagcctat agtgctgcca gaaaagaca       3300 gctggactgt caatgacata cagaagttag tggggaaatt gaattgggca agtcagattt      3360
acccagggat taaagtaagg caattatgta aactccttag aggaaccaaa gcactaacag      3420
aagtaatacc actaacagaa gaagcagagc tagaactggc agaaaacaga gagattctaa      3480
aagaaccagt acatggagtg tattatgacc catcaaaaga cttaatagca gaaatacaga      3540
agcaggggca aggccaatgg acatatcaaa tttatcaaga gccatttaaa aatctgaaaa      3600
caggaaaata tgcaagaatg aggggtgccc acactaatga tgtaaaacaa ttaacagagg      3660
cagtgcaaaa aataaccaca gaaagcatag taatatgggg aaagactcct aaatttaaac      3720
tgcccataca aaaggaaaca tgggaaacat ggtggacaga gtattggcaa gccacctgga      3780
ttcctgagtg ggagtttgtt aatacccctc ccttagtgaa attatggtac cagttagaga      3840
aagaacccat agtaggagca gaaaccttct atgtagatgg ggcagctaac agggagacta      3900
aattaggaaa agcaggatat gttactaata gaggaagaca aaaagttgtc ccctaactg       3960 acacaacaaa tcagaagact gagttacaag caatttatct agctttgcag gattcgggat      4020
tagaagtaaa catagtaaca gactcacaat atgcattagg aatcattcaa gcacaaccag      4080
atcaaagtga atcagagtta gtcaatcaaa taatagagca gttaataaaa aaggaaaagg      4140
tctatctggc atgggtacca gcacacaaag gaattggagg aaatgaacaa gtagataaat      4200
tagtcagtgc tggaatcagg aaagtactat ttttagatgg aatagataag cccaagatg       4260 aacatgagaa atatcacagt aattggagag caatggctag tgattttaac ctgccacctg      4320
tagtagcaaa agaaatagta gccagctgtg ataaatgtca gctaaaagga gagccatgc       4380 atggacaagt agactgtagt ccaggaatat ggcaactaga ttgtacacat ttagaaggaa      4440
aagttatcct ggtagcagtt catgtagcca gtggatatat agaagcagaa gttattccag      4500
cagaaacagg gcaggaaaca gcatattttc ttttaaaatt agcaggaaga tggccagtaa      4560
aaacaataca tactgacaat ggcagcaatt tcaccggtgc tacggttagg gccgcctgtt      4620
ggtgggcggg aatcaagcag gaatttggaa ttccctacaa tccccaaagt caaggagtag      4680
tagaatctat gaataaagaa ttaaagaaaa ttataggaca ggtaagagat caggctgaac      4740
atcttaagac agcagtacaa atggcagtat tcatccacaa ttttaaaaga aaggggggga      4800 ttgggggta cagtgcaggg gaaagaatag tagacataat agcaacagac atacaaacta      4860
aagaattaca aaaacaaatt acaaaaattc aaaattttcg ggtttattac agggacagca      4920
gaaatccact ttggaaagga ccagcaaagc tcctctggaa aggtgaaggg gcagtagtaa      4980
tacaagataa tagtgacata aaagtagtgc caagaagaaa agcaaagatc attagggatt      5040
atggaaaaca gatggcaggt gatgattgtg tggcaagtag acaggatgag gattagaaca      5100
tggaaaagtt tagtaaaaca ccatatgtat gtttcaggga agctagggg atggttttat       5160 agacatcact atgaaagccc tcatccaaga ataagttcag aagtacacat cccactaggg      5220
gatgctagat tggtaataac aacatattgg ggtctgcata caggagaaag agactggcat      5280
ttgggtcagg gagtctccat agaatggagg aaaaagagat atagcacaca agtagaccct      5340
```

```
gaactagcag accaactaat tcatctgtat tactttgact gttttttcaga ctctgctata   5400 agaaaggcct tattaggaca catagttagc cctaggtgtg aatatcaagc aggacataac   5460
aaggtaggat ctctacaata cttggcacta gcagcattaa taacaccaaa aaagataaag   5520
ccacctttgc ctagtgttac gaaactgaca gaggatagat ggaacaagcc ccagaagacc   5580
aagggccaca gagggagcca cacaatgaat ggacactaga gcttttagag gagcttaaga   5640
atgaagctgt tagacatttt cctaggattt ggctccatgg cttagggcaa catatctatg   5700
aaacttatgg ggatacttgg gcaggagtgg aagccataat aagaattctg caacaactgc   5760
tgtttatcca ttttcagaat tgggtgtcga catagcagaa taggcgttac tcgacagagg   5820
agagcaagaa atggagccag tagatcctag actagagccc tggaagcatc caggaagtca   5880
gcctaaaact gcttgtacca attgctattg taaaaagtgt tgctttcatt gccaagtttg   5940
tttcataaca aaagccttag gcatctccta tggcaggaag aagcggagac agcgacgaag   6000
agctcatcag aacagtcaga ctcatcaagc ttctctatca aagcagtaag tagtacatgt   6060
aacgcaacct ataccaatag tagcaatagt agcattagta gtagcaataa taatagcaat   6120
agttgtgtgg tccatagtaa tcatagaata taggaaaata ttaagacaaa gaaaaataga   6180
caggttaatt gatagactaa tagaaagagc agaagacagt ggcaatgaga gtgaaggaga   6240
aatatcagca cttgtggaga tgggggtgga gatgggcac catgctcctt gggatgttga   6300
tgatctgtag tgctacagaa aaattgtggg tcacagtcta ttatggggta cctgtgtgga   6360
aggaagcaac caccactcta ttttgtgcat cagatgctaa agcatatgat acagaggtac   6420
ataatgtttg ggccacacat gcctgtgtac ccacagaccc caacccacaa gaagtagtat   6480
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gaggtaaggt gcagaaagaa tatgcatttt tttataaact tgatataata ccaatagata   6780
atgatactac cagctataag ttgacaagtt gtaacacctc agtcattaca caggcctgtc   6840
caaaggtatc ctttgagcca attcccatac attattgtgc cccggctggt tttgcgattc   6900
taaaatgtaa taataagacg ttcaatggaa caggaccatg tacaaatgtc agcacagtac   6960
aatgtacaca tggaattagg ccagtagtat caactcaact gctgttaaat ggcagtctag   7020
cagaagaaga ggtagtaatt agatctgtca atttcacgga caatgctaaa accataatag   7080
tacagctgaa cacatctgta gaaattaatt gtacaagacc caacaacaat acaagaaaaa   7140
gaatccgtat ccagagagga ccaggagag catttgttac aataggaaaa ataggaaata   7200
tgagacaagc acattgtaac attagtagag caaaatggaa taacacttta aaacagatag   7260
ctagcaaatt aagagaacaa tttggaaata taaaacaat aatctttaag caatcctcag   7320
gaggggaccc agaaattgta acgcacagtt ttaattgtgg aggggaattt ttctactgta   7380
attcaacaca actgtttaat agtacttggt taatagtac ttggagtact gaagggtcaa   7440
ataacactga aggaagtgac acaatcaccc tcccatgcag aataaaacaa attataaaca   7500
tgtggcagaa agtaggaaaa gcaatgtatg cccctcccat cagtggacaa attagatgtt   7560
catcaaatat tacagggctg ctattaacaa gagatggtgg taatagcaac aatgagtccg   7620
agatcttcag acctggagga ggagatatga gggacaattg gagaagtgaa ttatataaat   7680
```

| | |
|---|---|
| ataaagtagt aaaaattgaa ccattaggag tagcacccac caaggcaaag agaagagtgg | 7740 |
| tgcagagaga aaaaagagca gtgggaatag gagctttgtt ccttgggttc ttgggagcag | 7800 |
| caggaagcac tatgggcgca gcctcaatga cgctgacggt acaggccaga caattattgt | 7860 |
| ctggtatagt gcagcagcag aacaatttgc tgagggctat tgaggcgcaa cagcatctgt | 7920 |
| tgcaactcac agtctggggc atcaagcagc tccaggcaag aatcctggct gtggaaagat | 7980 |
| acctaaagga tcaacagctc ctggggattt ggggttgctc tggaaaactc atttgcacca | 8040 |
| ctgctgtgcc ttggaatgct agttggagta ataaatctct ggaacagatt tggaatcaca | 8100 |
| cgacctggat ggagtgggac agagaaatta acaattacac aagcttaata cactccttaa | 8160 |
| ttgaagaatc gcaaaaccag caagaaaaga atgaacaaga attattggaa ttagataaat | 8220 |
| gggcaagttt gtggaattgg tttaacataa caaattggct gtggtatata aaattattca | 8280 |
| taatgatagt aggaggcttg gtaggtttaa gaatagtttt tgctgtactt tctatagtga | 8340 |
| atagagttag gcagggatat tcaccattat cgtttcagac ccacctccca accccgaggg | 8400 |
| gacccgacag gcccgaagga atagaagaag aaggtggaga gagagacaga gacagatcca | 8460 |
| ttcgattagt gaacggatcc ttggcactta tctgggacga tctgcggagc ctgtgcctct | 8520 |
| tcagctacca ccgcttgaga gacttactct tgattgtaac gaggattgtg gaacttctgg | 8580 |
| gacgcagggg gtgggaagcc ctcaaatatt ggtggaatct cctacagtat tggagtcagg | 8640 |
| aactaaagaa tagtgctgtt agcttgctca atgccacagc catagcagta gctgagggga | 8700 |
| cagatagggt tatagaagta gtacaaggag cttgtagagc tattcgccac atacctagaa | 8760 |
| gaataagaca gggcttggaa aggattttgc tataagatgg gtggcaagtg gtcaaaaagt | 8820 |
| agtgtgattg gatggcctac tgtaagggaa agaatgagac gagctgagcc agcagcagat | 8880 |
| agggtgggag cagcatctcg agacctggaa aaacatggag caatcacaag tagcaataca | 8940 |
| gcagctacca atgctgcttg tgcctggcta gaagcacaag aggaggagga ggtgggtttt | 9000 |
| ccagtcacac ctcaggtacc tttaagacca atgacttaca aggcagctgt agatcttagc | 9060 |
| cacttttta aagaaaaggg gggactggaa gggctaattc actcccaaag aagacaagat | 9120 |
| atccttgatc tgtggatcta ccacacacaa ggctacttcc ctgattagca gaactacaca | 9180 |
| ccagggccag gggtcagata tccactgacc tttggatggt gctacaagct agtaccagtt | 9240 |
| gagccagata agatagaaga ggccaataaa ggagagaaca ccagcttgtt acaccctgtg | 9300 |
| agcctgcatg gatggatga cccggagaga gaagtgttag agtggaggtt tgacagccgc | 9360 |
| ctagcatttc atcacgtggc ccgagagctg catccggagt acttcaagaa ctgctgacat | 9420 |
| cgagcttgct acaagggact ttccgctggg gactttccag ggaggcgtgg cctgggcggg | 9480 |
| actggggagt ggcgagccct cagatcctgc atataagcag ctgcttttg cctgtactgg | 9540 |
| gtctctctgg ttagaccaga tctgagcctg ggagctctct ggctaactag ggaacccact | 9600 |
| gcttaagcct caataaagct tgccttgagt gcttcaagta gtgtgtgccc gtctgttgtg | 9660 |
| tgactctggt aactagagat ccctcagacc ctttagtca gtgtggaaaa tctctagca | 9719 |

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29

| | |
|---|---|
| aactcggggg agatcccttc ca | 22 |

```
<210> SEQ ID NO 30
<211> LENGTH: 25
<212> TYPE: DNA
<213> ORGANISM: Artificial sequence
<220> FEATURE:
<223> OTHER INFORMATION: Antisense cfos oligonucleotide

<400> SEQUENCE: 30
catcatggtc gtggtttggg caaac                                              25

<210> SEQ ID NO 31
<211> LENGTH: 25
<212> TYPE: DNA
<213> ORGANISM: Artificial sequence
<220> FEATURE:
<223> OTHER INFORMATION: Sense cfos oligonucleotide

<400> SEQUENCE: 31
gtttgcccaa accacgacca tgatg                                              25

<210> SEQ ID NO 32
<211> LENGTH: 26
<212> TYPE: DNA
<213> ORGANISM: Artificial sequence
<220> FEATURE:
<223> OTHER INFORMATION: Antisense actin oligonucleotide

<400> SEQUENCE: 32
gagggagagc atagccctcg tagatg                                             26

<210> SEQ ID NO 33
<211> LENGTH: 26
<212> TYPE: DNA
<213> ORGANISM: Artificial sequence
<220> FEATURE:
<223> OTHER INFORMATION: Sense actin oligonucleotide

<400> SEQUENCE: 33
catctacgag ggctatgctc tccctc                                             26

<210> SEQ ID NO 34
<211> LENGTH: 22
<212> TYPE: DNA
<213> ORGANISM: Artificial Sequence
<220> FEATURE:
<223> OTHER INFORMATION: Antisense fosB oligonucleotide

<400> SEQUENCE: 34
ccttagcgga tgttgaccct gg                                                 22

<210> SEQ ID NO 35
<211> LENGTH: 22
<212> TYPE: DNA
<213> ORGANISM: Artificial Sequence
<220> FEATURE:
<223> OTHER INFORMATION: Sense fosB oligonucleotide

<400> SEQUENCE: 35
ccagggtcaa catccgctaa gg                                                 22

<210> SEQ ID NO 36
<211> LENGTH: 24
<212> TYPE: DNA
<213> ORGANISM: Artificial Sequence
<220> FEATURE:
```

<223> OTHER INFORMATION: Antisense deltafosB oligonucleotide

<400> SEQUENCE: 36
acttgaactt cactcggcca gcgg                                           24

<210> SEQ ID NO 37
<211> LENGTH: 20
<212> TYPE: DNA
<213> ORGANISM: Artificial Sequence
<220> FEATURE:
<223> OTHER INFORMATION: Antisense mmp9 oligonucleotide

<400> SEQUENCE: 37
tacatgagcg cttccggcac                                                20

<210> SEQ ID NO 38
<211> LENGTH: 20
<212> TYPE: DNA
<213> ORGANISM: Artificial Sequence
<220> FEATURE:
<223> OTHER INFORMATION: Sense mmp9 oligonucleotide

<400> SEQUENCE: 38
gtgccggaag cgctcatgta                                                20

<210> SEQ ID NO 39
<211> LENGTH: 25
<212> TYPE: DNA
<213> ORGANISM: Artificial Sequence
<220> FEATURE:
<223> OTHER INFORMATION: Nestin oligonucleotide

<400> SEQUENCE: 39
tcccaaggaa atgcagcttc tgctt                                          25

<210> SEQ ID NO 40
<211> LENGTH: 20
<212> TYPE: DNA
<213> ORGANISM: Mus musculus

<400> SEQUENCE: 40
gtctccgctc catcctgccc                                                20

<210> SEQ ID NO 41
<211> LENGTH: 20
<212> TYPE: DNA
<213> ORGANISM: Mus musculus

<400> SEQUENCE: 41
aagggcctgc ctctcagcct                                                20

<210> SEQ ID NO 42
<211> LENGTH: 20
<212> TYPE: DNA
<213> ORGANISM: Artificial Sequence
<220> FEATURE:
<223> OTHER INFORMATION: Antisense hdac5 AS2 oligonucleotide

<400> SEQUENCE: 42
aggctgagag gcaggcccct                                                20

<210> SEQ ID NO 43
<211> LENGTH: 23
<212> TYPE: DNA
<213> ORGANISM: Artificial Sequence

```
<220> FEATURE:
<223> OTHER INFORMATION: Antisense MAO-A oligonucleotide

<400> SEQUENCE: 43
aatcctgaga tgccgcctcc aat                                              23

<210> SEQ ID NO 44
<211> LENGTH: 25
<212> TYPE: DNA
<213> ORGANISM: Artificial Sequence
<220> FEATURE:
<223> OTHER INFORMATION: Sense MAO-A oligonucleotide

<400> SEQUENCE: 44
atacatcagc tccgccctcg gactt                                            25

<210> SEQ ID NO 45
<211> LENGTH: 24
<212> TYPE: DNA
<213> ORGANISM: Artificial Sequence
<220> FEATURE:
<223> OTHER INFORMATION: Antisense UCPB oligonucleotide

<400> SEQUENCE: 45
agggccccct tcatgaggtc atat                                             24

<210> SEQ ID NO 46
<211> LENGTH: 20
<212> TYPE: DNA
<213> ORGANISM: Homo sapiens

<400> SEQUENCE: 46
tggcgccggt tacagaacca                                                  20

<210> SEQ ID NO 47
<211> LENGTH: 23
<212> TYPE: RNA
<213> ORGANISM: Artificial Sequence
<220> FEATURE:
<223> OTHER INFORMATION: Mature miR-9 oligonucleotide

<400> SEQUENCE: 47
ucauacagcu agauaaccaa aga                                              23

<210> SEQ ID NO 48
<211> LENGTH: 18
<212> TYPE: RNA
<213> ORGANISM: Artificial Sequence
<220> FEATURE:
<223> OTHER INFORMATION: Precursor miR-9-pri-1 oligonucleotide

<400> SEQUENCE: 48
agauaacaac caaccccg                                                    18

<210> SEQ ID NO 49
<211> LENGTH: 18
<212> TYPE: RNA
<213> ORGANISM: Artificial Sequence
<220> FEATURE:
<223> OTHER INFORMATION: Precursor miR-9-pri-2 oligonucleotide

<400> SEQUENCE: 49
agauaacaac ucgcuucc                                                    18

<210> SEQ ID NO 50
```

```
<211> LENGTH: 18
<212> TYPE: RNA
<213> ORGANISM: Artificial Sequence
<220> FEATURE:
<223> OTHER INFORMATION: Precursor miR-9-pri-3 oligonucleotide

<400> SEQUENCE: 50
agagagaaac gggccucc                                                   18

<210> SEQ ID NO 51
<211> LENGTH: 21
<212> TYPE: DNA
<213> ORGANISM: Human immunodeficiency virus

<400> SEQUENCE: 51
tcaactgtgg caaggaagga c                                               21

<210> SEQ ID NO 52
<211> LENGTH: 21
<212> TYPE: DNA
<213> ORGANISM: Human immunodeficiency virus

<400> SEQUENCE: 52
ggaaaggtga aggggcagta g                                               21

<210> SEQ ID NO 53
<211> LENGTH: 20
<212> TYPE: DNA
<213> ORGANISM: Human immunodeficiency virus

<400> SEQUENCE: 53
gggtgccaac atagcagaaa                                                 20

<210> SEQ ID NO 54
<211> LENGTH: 21
<212> TYPE: DNA
<213> ORGANISM: Human immunodeficiency virus

<400> SEQUENCE: 54
gctccatggc ttaggacagt a                                               21

<210> SEQ ID NO 55
<211> LENGTH: 21
<212> TYPE: DNA
<213> ORGANISM: Human immunodeficiency virus

<400> SEQUENCE: 55
agcagccata gttgtgtgga t                                               21

<210> SEQ ID NO 56
<211> LENGTH: 21
<212> TYPE: DNA
<213> ORGANISM: Human immunodeficiency virus

<400> SEQUENCE: 56
tagggcaaag agttggtagg g                                               21

<210> SEQ ID NO 57
<211> LENGTH: 21
```

```
<212> TYPE: DNA
<213> ORGANISM: Human immunodeficiency virus

<400> SEQUENCE: 57
cttaacaacc agacggacca g                                      21
```

SUICIDE CONTRAST AGENTS TARGETING HIV RESERVOIRS FOR THERANOSTIC ERADICATION

CROSS REFERENCE TO RELATED APPLICATIONS

This application is the National Stage of International Application PCT/US2014/065613 filed on Nov. 14, 2014, which claims benefit under 35 U.S.C. 119(e) of U.S. Provisional Patent Application Ser. No. 61/904,238 filed on Nov. 14, 2013. The content of both applications is incorporated herein by reference in its entirety.

FEDERALLY SPONSORED RESEARCH

This invention was made with US Government support under grants EB013678 and DA029829 awarded by the National Institutes of Health. The US Government has certain rights in the invention.

SEQUENCE LISTING

A computer readable file containing a sequence listing is being electronically co-filed herewith via EFS-Web. The computer readable file, submitted under 37 CFR § 1.821(e), will also serve as the copy required by 37 § CFR 1.821(c). The file (filename "29R4206.TXT") was created on May 10, 2016 and has a size of 23,215 bytes.

The content of the computer readable file is hereby incorporated by reference in its entirety.

FIELD OF INVENTION

One aspect of the present invention relates to in vitro and in vivo models of HIV reservoirs (latent infection). Another aspect of the invention relates to suicide agents to treat latent HIV infection (reduce the number of cells with HIV reservoirs).

BACKGROUND

At the end of 2009, an estimated 1,148,200 persons aged 13 and older were living with HIV infection in the United States; approximately 50,000 people in the United States are newly infected with HIV each year. Worldwide, there were about 2.5 million new cases of HIV in 2011. About 34.2 million people are living with HIV around the world. (Centers for Disease Control and Prevention).

The eradication of HIV-1 from infected individuals is stymied by the persistence of the virus in a stable reservoir of latently infected CD4$^+$ T cells. Latently infected cells can be found in all HIV-1 infected individuals at a very low frequency and allow the virus to persist despite antiretroviral therapy for the lifetime of an infected patient. Current efforts are focused on identifying small molecules or immune strategies to eliminate these latently infected cells.

Treatment failure due to low drug penetration in the CSF and CNS is high and treating latent HIV is challenging. Regular MRI and CT can establish CNS damage but not viral infection of the brain. Accordingly, there is a need in the art for the agents that can detect and treat latent HIV infection.

SUMMARY

Herein we have developed both in vitro and in vivo animal models of HIV reservoirs (latent HIV infection). We have also developed agents "suicide agents" that can specifically reduce the number of latent HIV infected neural cells. We have developed an MRI iron oxide molecule attached to a nucleic acid sequence that binds to HIV specific genes and thereby delivers a toxic compound to the infected cell ("a suicide contrast agent). We have developed a RNA-targeting MRI contrast agent that can be delivered to the brain of a living subject for detection. We have further developed agents to that, when coupled with MRI, will reduce latent HIV by selectively killing only infected neural cells. Such customized contrast agents specifically target HIV viral RNA within the cell We have developed a model system of HIV reservoirs in neural cells by generating chimeric phosphorothioate-modified oligodeoxynucleotides (sODN) that specifically interact with neural cell DNA or RNA, and that further comprise a sequence of the HIV genome. In particular, we have conjugated the chimera sODN to a delivery vehicle (e.g. a superparamagnetic iron oxide nanoparticle (SPIO)) and have demonstrated specific delivery to neural cells, in vitro and in vivo. These model systems can be used to screen for agents that specifically target latent viral infection. Using the model system, we have develop suicide MRI contrast agents that can be used to reduce the number of neural cells that harbor the virus.

Accordingly, one aspect of the invention provides neural cells comprising a phosphorothioate-modified oligodeoxynucleotide (sODN), wherein the sODN comprises a) a neural target DNA nucleotide sequence that targets a sequence in the neural cell and b) a mRNA coding sequence of the HIV genome. These neural cells are useful for testing of agents that can be used to specifically eradicate cells with latent HIV infection, having HIV reservoirs. In certain embodiments the neural cells are in vitro, e.g. in a cell culture. In certain embodiments, the neural cells are in vivo. In certain embodiments, the sODN further comprises a linker. The neural target DNA nucleotide sequence that targets a sequence in the neural cell, can target mRNA or genomic DNA, for example target mRNA of a protein of neurons such as cFos, actin, FosB, deltafosB, matrix metalloproteinase-9 (mmp9), nestin, glilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4). Example RNA sequences of the HIV genome, include for example, gag, pol, VPr2, vpr1, vpu, gp160, or vif.

In another aspect of the invention, methods for making of the in vitro and in vivo animal models of HIV reservoirs are provided. The methods comprise administering a phosphorothioate-modified oligodeoxynucleotide (sODN), wherein the sODN comprises a) a neural target DNA nucleotide sequence that targets a sequence in the neural cell and b) a mRNA coding sequence of the HIV genome, as described.

Another aspect of the invention relates to the development of contrast agents that selectively result in cell death of neural cells having HIV reservoirs. These agents can be used in combination with MRI for treatment of latent HIV infection.

An exemplary method for the generation of latent HIV reservoir infection is described herein. However, one of skill in the art will understand from the method that the same technology and steps can be used to generate in vitro and in vivo animal models for other viruses that have latent neural reservoir infection by using a mRNA coding sequence (or DNA genomic sequence) of the virus of interest, e.g. Chicken pox virus, Herpes simplex viruses I and II, hepatitis viruses A, B, C and D, and Ebola virus.

Thus, in still another aspect of the invention, methods for generating models of latent viral infection in the central nervous system are provided. The methods comprise contacting a neural cell with a contrast agent (e.g. a superparamagnetic iron oxide nanoparticle (SPIO)) linked to a phosphorothioate-modified oligodeoxynucleotide (sODN), wherein the sODN comprises a) a neural target DNA nucleotide sequence that targets a sequence in the neural cell and b) a mRNA coding sequence of the viral genome, e.g. wherein the viral genome is selected from the group consisting of HIV I and II, Chicken pox virus, Herpes simplex viruses I and II, hepatitis viruses A, B, C and D, and Ebola virus.

BRIEF DESCRIPTION OF THE DRAWINGS

FIG. 4.1 is a schematic and gel electrophoresis FIG. 4.2. $^{32}$P-sODN-cfos is hybridized to RNA (left) and the hybrids are released to single-stranded sODN after digestion with RNases (as illustrated in cartoon on the right), see also (Liu et al., 1994).

FIGS. 10a to 10D. The contrast to noise ratio (CNR) of SPION-gfap stabilized at ~15 in living mouse brain at 6 hrs after delivery (see Liu et al., 2013, FIG. 5A to 5 D).

FIGS. 11a to 11B. Show MRI maps. ΔR2* maps show a reduction in glial cell population in the striatum. Gliogenesis is present in the septum (short arrows), SSC (solid arrows) and SVZ (broken arrows), as detected by MRI and SPION-gfap and validated by ex vivo microscopy (B) (Liu et al., 2013). The results show target-precision of our contrast agent reflects the location of cell mass based on unique gene transcript within.

FIGS. 12A to 12D show MRIs. Detecting HIV reservoir in living mouse brain. We determined the stability of the recombinant HIV reservoirs and MR beacons in the CSF of mice and NHP to be for 24 hours, at 37° C. In proof-of-concept studies, we acquired MRI for pre-infusion baseline R2* maps one day before MRI (12A). We transfected the sODN of reservoir (Cy3[+]hivT531-ASgfap, B) or control (Cy3[−]hivT531-ASgfap,C) to live mouse brains (n=2 each) at 120 pmol/kg (icy) (bottom panels of respective B & C) and allowed uptake for 3 hours. We then delivered the beacon (SPION-[−]hivT531, 4 mg Fe per kg, i.p.). MRI was acquired again at 24 hrs after Beacon delivery (top panels of 12B & 12C). An increase in the rate of signal reduction (ΔR2* maps in 12D) is clearly shown in mouse brains with HIV reservoir (I), but not the control (II). Color scale bar at right shows change in R2* (per sec).

FIG. 17A are images of the brain of live mouse that show the proof of concept to demonstrate target-guided delivery and detection of a foreign gene in a viral genome after infection: FIG. 17B no foreign gene is detected in placebo control, both are live mice, See Example 3. FIG. 17C is postmortem necropsy examination of antigen expressed from this foreign gene; FIG. 17D show no such antigen.

FIG. 18A: Schiff bases are common enzymatic intermediates where an amine reacts with an aldehyde or ketone of a cofactor or substrate. FIG. 18B Thioether linkages (C-S-C) are important in biology (amino acid methionine and cofactor biotin).

DETAILED DESCRIPTION

Figure 1:
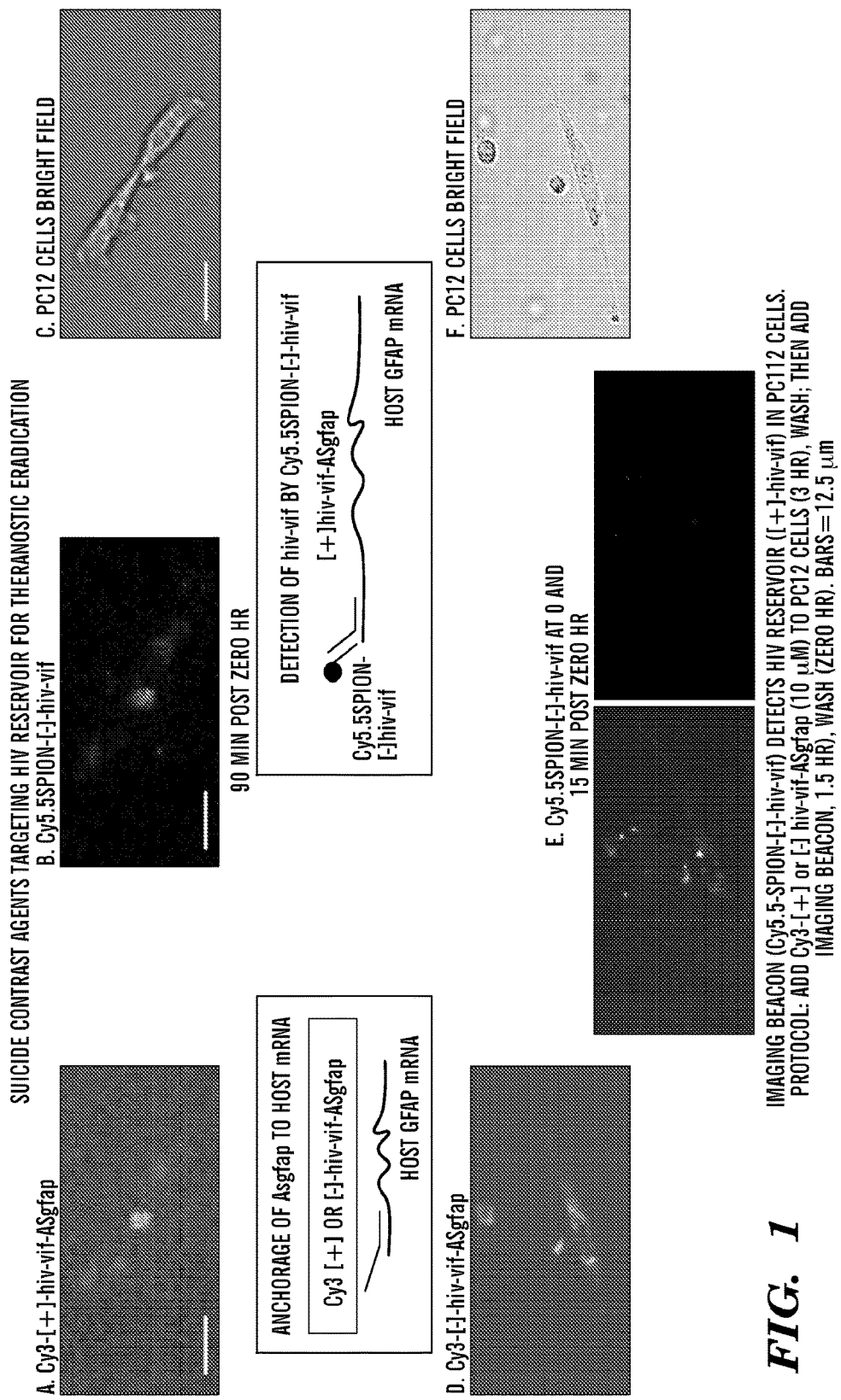
FIGS. 1A to 1F indicate that imaging beacon Cy5.5-SPION-[−]-hiv vif detects HIV reservoir ([+]-hiv-vif) in PC12 cells. We transfected PC12 cells with sODN (30 pmol/ml) of either sODN for reservoir or control (Cy3 labeled [+] or [−]-hiv-vif-ASgfap, respectively). Upon completion of transfection, the sODN were removed by washing and replacing DNA-free medium; we exposed the cells again by adding imaging beacon (Cy5.5-SPION-[−] hiv-vif) for 90 min. The cells were washed again to remove excess Cy5.5-SPION-[−]hiv-vif. At this time point, which we refer to as the zero hr, we observed retention of both Cy3-labeled reservoir and control sODN at zero hour (panels 1A and 1D). Retention of the imaging beacon by both groups at zero hour indicates cell uptake (1B and especially Panel E [left]). By 15 min the signal was no longer visible in the control group (Panel E right); by contrast, it remained visible in the reservoir group 90 min after zero hr (1B). A bright-field photo shows the location of PC12 cells (Panels 1C & 1F). The protocol was repeated using the cytotoxic beacon (Gd-[−]hiv-vif, 28 nmol Gd or 28 pmol sODN per ml). Colony-forming ability was reduced by 50% (p=0.034, paired t test (one tail) in cells with the reservoir, as confirmed by two tests (average from 40% and 61%). Cells with the control sODN were 100% of those without transfection. The mechanism of killing is the precise delivery of toxic Gd to and with retention in cells that harbor the reservoir sODN. This result suggests this unique strategy using suicide beacon is safe to cells without the reservoir. Additional target sites (polymerase [pol] & and envelope glycoprotein 120 [gp120]) are being made for reservoir sODN in which there will be partial gene sequence (pol, vif and gp120) for Gd-[−]-hiv-pol-vif-gp120. Combination theranostic beacons on multiple HIV genomes may increase Gd per reservoir sODN and avoid reduced specificity if RNA genome mutates.
Figure 2:
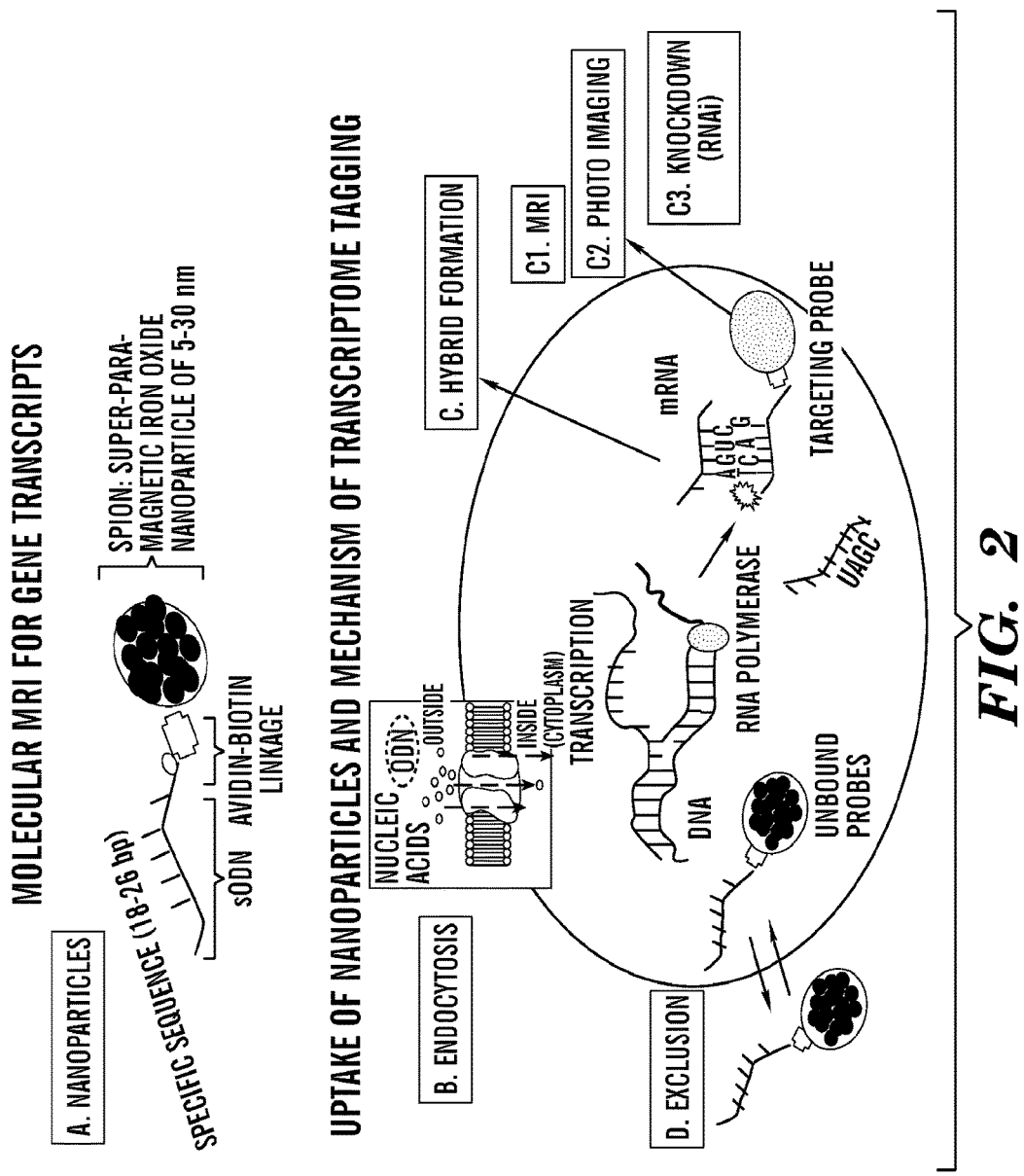
FIG. 2. Shows a schematic of contrast agent (e.g. labeled with SPION) uptake. Adapted from (Liu et al., 2013)
Figure 3:
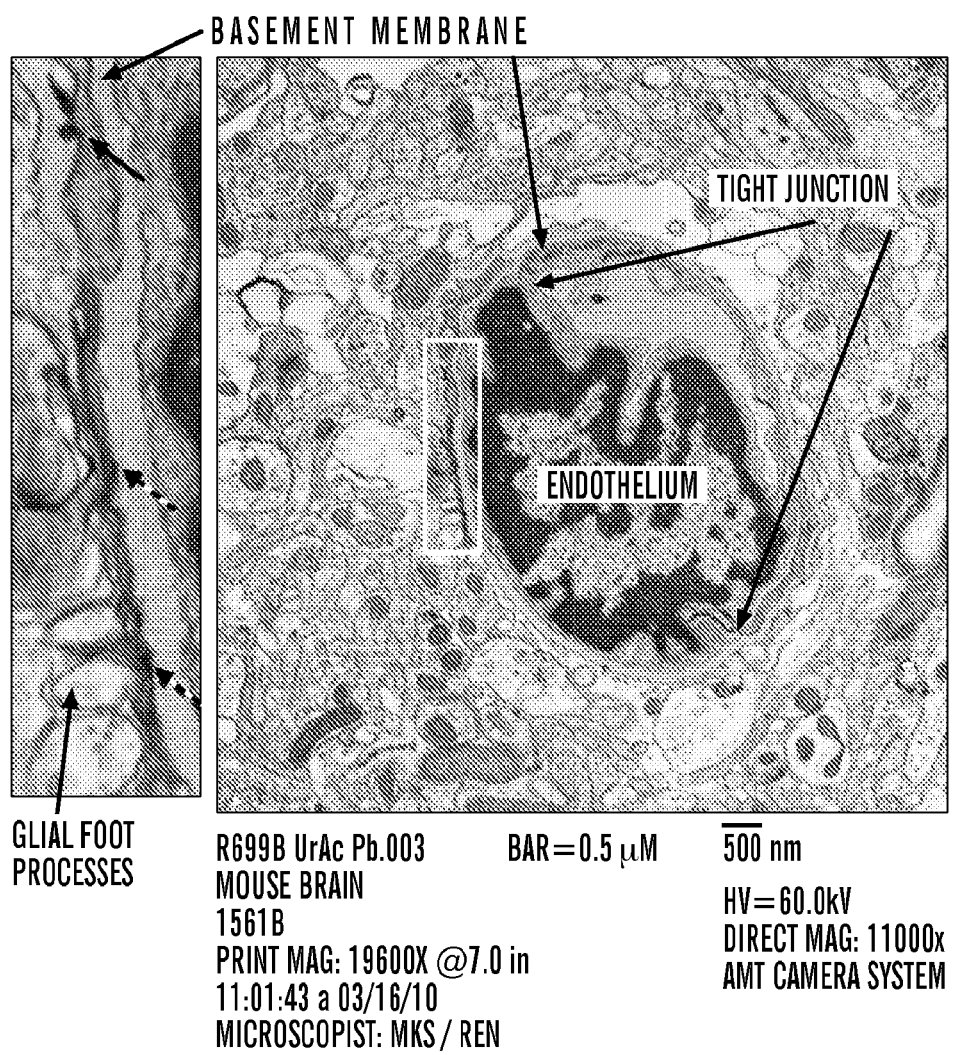
FIG. 3. Electron micrograph. Uptake by endocytosis (Liu et al., 2013) SPION-DNA, full stain of a microvessel (arrows showing tight junction and basement membrane). Electron dense nanoparticles (EDNs) passing perivascular space (arrows, enlargement of the box) and enclosed in membrane (asterisks, enlargement of the box).
Figure 4:
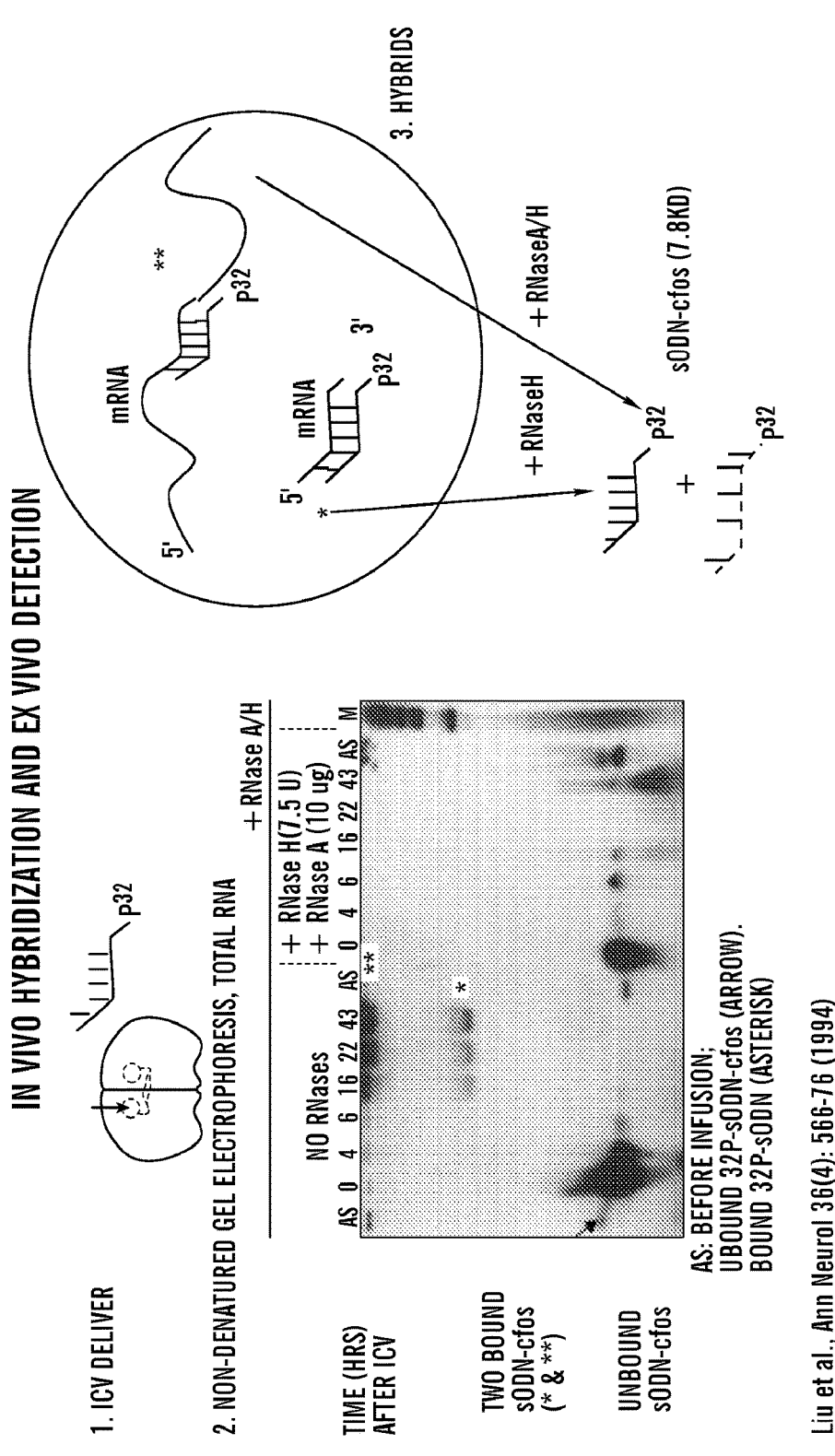
FIG. 4.

One aspect of the present invention provides in vitro and in vivo models of HIV reservoirs found in neural cells and central nervous system (CNS). Methods for making the models are also provided. Another aspect of the present invention provides suicide contrast agents that when coupled with MRI, selectively reduce the number of cells having HIV reservoirs.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "oligonucleotide" refers to a polymer or oligomer of nucleotide or nucleoside monomers comprising naturally occurring bases sugars and intersugar (backbone) linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake, increased stability in the presence of nucleases, and the like.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences between sODN and the target sequence, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., in cytoplasm or nucleus. However, where two oligonucleotides are designed to form, upon hybridization, one or more single stranded overhangs, such overhangs shall not be regarded as mismatches with regard to the determination of complementarity. For example, when making the in vitro and in vivo models the HIV mRNA sequence overhangs to serve as the reservoir.

"Complementary" sequences, as used herein, can also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein can be used with respect to the base matching between the sense strand ((+) strand) and the antisense strand ((−) strand)) of RNA or sense and antisense DNA.

As used herein, a polynucleotide that is "substantially complementary to at least part of" a target gene refers to a polynucleotide that is substantially complementary to a contiguous portion of a target gene of interest (e.g., an mRNA encoded by a target gene (e.g antisense (−) oligonucleotide binds to HIV coding mRNA or to mRNA of Fos, Actin, FosB, detafosB, MMP9, nestin, gfap, hdac5AS2, lba1, and Oct4; and (sense (+) binds only the genomic target gene sequence, e.g. non-coding strand of a target gene (e.g (+) oligonucleotide binds to non-coding strand of of Fos, Actin, FosB, detafosB, MMP9, nestin, gfap, hdac5AS2, lba1, and Oct4, HIV non-coding). For example, a polynucleotide is complementary to at least a part of a target mRNA if the sequence is substantially complementary to a non-interrupted portion of an mRNA encoded by a target gene.

The terms "decrease", "reduced", "reduction", "decrease" or "inhibit" are all used herein generally to mean a decrease by a statistically significant amount. In certain embodiments, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% as compared to a reference level. The reference level is a control level in the absence of agent/treatment, e.g. with respect to suicide agents, the number of cells harboring HIV reservoirs in a subject in the absence of treatment with the suicide agent cells, e.g. as determined using detection agents.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. The reference level is a control level in the absence of agent/treatment.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

The terms "individual", "subject", "host", and "patient" are used interchangeably herein and refer to any mammalian subject for whom diagnosis, treatment, or therapy is desired, particularly humans.

A "variant" nucleic acid refers to a nucleic acid having at least 70%, 75%, 80%, 85%, 90%, 95%, 98%, or 99% sequence identity with a native sequence. Such variants wherein one or more nucleic acids are added at the 5' or 3' end, or within, the native sequence; or from about one to forty nucleotides are deleted, and optionally substituted by one or more bases.

As used herein, the term "treating" and "treatment" refers to administering to a subject an effective amount of a composition (e.g. suicide contrast agent) so that the subject has a reduction in latent infection or a reduction in at least one symptom of the HIV disease or an improvement in the disease, for example, beneficial or desired clinical results. For purposes of this invention, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission, whether detectable or undetectable. The effect can be monitored by monitoring viral load. One of skill in the art realizes that a treatment improves the disease condition, and is not intended to be a complete cure for the disease. The treatment is "effective" if the progression of a disease is reduced or halted, or the latent stores of HIV are reduced, e.g. as monitored using MRI detection agents with AS-HIV sODN.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. For example, reference to a "suicide contrast agent", includes a plurality of such agents includes reference to one or more agents and equivalents thereof known to those skilled in the art, and so forth, it is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

A nucleic acid that hybridizes or binds "specifically" to a target nucleic acid hybridizes or binds preferentially to the target, and does not substantially bind to other molecules or compounds in a biological sample.

As used herein, "paramagnetic" means having positive magnetic susceptibility and lacking magnetic hysteresis (ferromagnetism).

As used herein, "superparamagnetic" means having positive magnetic susceptibility and lacking magnetic hysteresis (ferromagnetism) at temperatures below the Curie or the Neel temperature of the material.

As used herein, the term "ran" refers to a randomized nucleotide sequence. sODN-Ran is an randomized sequence which has no target in the mammalian cells. For example, "+"Ran: GGGATCGTTCAGAGTCTA (SE ID NO: 26) and "−"Ran: TAGACTCTGAACGATCCC (SE ID NO: 27).

Methods for generating models of latent viral infection are provided (e.g. latent HIV reservoir infection, HIV I and II, Chicken pox virus, Herpes simplex viruses I and II, hepatitis viruses A, B, C and D, and Ebola virus). An exemplary method for the generation of latent HIV reservoir infection is described herein. However, one of skill in the art will understand from the method that the same technology and steps can be used to generate in vitro and in vivo animal models for other viruses that have latent reservoir infection by using a mRNA coding sequence (or DNA genomic sequence) of the virus of interest.

Accordingly, in one aspect of the invention, methods for generating models of latent viral infection in the central nervous system are provided. The methods comprise contacting a neural cell with a contrast agent (e.g. a superparamagnetic iron oxide nanoparticle (SPIO)) linked to a phosphorothioate-modified oligodeoxynucleotide (sODN), wherein the sODN comprises a) a neural target DNA nucleotide sequence that targets a sequence in the neural cell and b) a mRNA coding sequence of the viral genome, e.g. wherein the viral genome is selected from the group consisting of HIV I and II, Chicken pox virus, Herpes simplex viruses I and II, hepatitis viruses A, B, C and D, and Ebola virus.

In another aspect, a method for generating a model of latent HIV infection in the central nervous system is provided. The method comprises contacting a neural cell with a contrast agent (e.g. a superparamagnetic iron oxide nanoparticle (SPIO)) linked to a phosphorothioate-modified oligodeoxynucleotide (sODN), wherein the sODN comprises a) a neural target DNA nucleotide sequence that targets a sequence in the neural cell and b) a mRNA coding sequence of the HIV genome.

The contacting of neural cells can be done in vitro (e.g. by adding the sODN (e.g. SPIO linked sODN) to cell culture media) or in vivo (e.g. by administering the SPIO linked sODN to the mammal using intracerebroventricular delivery (ICV)). In vivo and in vitro cell contacting are well known in the art and, for example, are described in detail in Liu et al. (MRI reveals different effects of amphetamine exposure on neuroglia in vivo) 2013, The FASEB Journal 27: 1-13; and in Liu et al. (DNA BASES MRI Probes for Specific Detection of Chronic Exposure to Amphetamine in Living Brains) 2009, Neurobiology of disease 29(34):10663-10670; See also examples herein In one embodiment the neural cell is selected from the group consisting of a glial cell, a neuron, a pericyte (neural progenitor cell) and a cell of the epithelia of the neurovascular unit.

In one embodiment, the neural target DNA nucleotide sequence is an antisense sequence ("–" strand) that targets mRNA of a protein selected from the group consisting of cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1Iba1), and octamer-binding transcription factor 4 (OCT4).

In one embodiment, the neural target DNA sequence is a sense sequence ("+" stand) that targets the transcribe strand of genomic DNA, selected from the group consisting of cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1Iba1), and octamer-binding transcription factor 4 (OCT4).

Example antisense and sense sequences to the target genomic ("+") and mRNA ("–") of cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1Iba1), and octamer-binding transcription factor 4 (OCT4) are provided under the heading sequences (e.g. SEQ ID NO.'s: 30-50, as indicated). The DNA sequence that targets the mRNA or genomic DNA of the neural target gene are complimentary to at least a portion of the mRNA or genomic DNA respectively, and can be determined by one of skill in the art. The mRNA and DNA sequences are readily available in the Gene Bank database, see, for example the Gene Bank Accession numbers listed under the "SEQUENCES" heading herein. In certain embodiments, the neural target DNA nucleotide sequence that targets a sequence in the neural cell is at least 10 nucleotides (nts) in length, at least 15 nts in length, at least 20 nts in length, or more. Typically the target DNA nucleotide sequence that targets a sequence in the neural cell ranges from 10-30 nts in length.

In one embodiment, the neural target DNA sequence targets gfap mRNA.

In one embodiment, the gfap comprises a "–" strand sequence selected from the group consisting of SEQ ID NO: 1, SEQ ID NO: 2 and SEQ ID NO: 3. Herein SEQ ID NO: 1 is TGATACGTCTCCGCTCCATC of rats; SEQ ID NO: 2 is TGTCTCCGCTCCATCCTGCCC of mouse, and SEQ ID NO: 3 is CGTCAAGCTCCACATGGACCTG of humans.

In one embodiment, the neural target DNA sequence targets gfap genomic DNA. In certain embodiments the neural target DNA sequence targets gfap genomic DNA is selected from ("+") strand SEQ ID NO: 4, SEQ ID NO: 5, and SEQ ID NO: 6. Herein SEQ ID NO 4 is GATGGAGCG-GAGACGTATCA of rats, SEQ ID NO: 5 is GGGCAG-GATGGAGCGGAGACA of mice; and SEQ ID NO: 6 is CAGGTCCATGTGGAGCTTGACG of humans.

In one embodiment, the neural target DNA sequence that targets gfap genomic DNA comprises SEQ ID NO: 7 or SEQ ID No: 8 of human glioma cells. Herein, ("–" strand SEQ ID NO: 7 is CGTCAAGCTCCACATGGACCTG of human; ("+" strand SEQ ID NO: 8 is CAGGTCCATGTGGAGCT-TGACG of humans.

In one embodiment, the mRNA coding sequence of the HIV genome is selected from the group consisting of gag, pol, VPr2, vpr1, vpu, gp160, or vif. The mRNA coding sequence may be a portion of the mRNA coding sequence, e.g. at least 18 nts in length, typically less than 30 nucleotides in length of contiguous sequence. In certain embodiments the mRNA coding sequence is selected from the group consisting of the "+" sense sequences of HIV-gag sequence, 21 nucleotides TCAACTGTG-GCAAGGAAGGAC (SEQ ID NO: 51); HIV-pol sequence, 21 nucleotides GGAAAGGTGAAGGGGCAGTAG (SEQ ID NO: 52); HIV-Vpr2 sequence, 20 nucleotides GGGT-GCCAACATAGCAGAAA (SEQ ID NO: 53); HIV-Vpr1 sequence, 21 nucleotides GCTCCATGGCTTAGGACA-GTA (SEQ ID NO: 54); HIV-Vpu sequence, 21 nucleotides AGCAGCCATAGTTGTGTGGAT (SEQ ID NO: 55); HIV-Gp160 sequence, 21 nucleotides TAGGGCAAAGAGTTG-GTAGGG (SEQ ID NO: 56); and HIV-vif sequence, 21 nucleotides CTTAACAACCAGACGGACCAG (SEQ ID NO: 57). In one embodiment the antisense sequences are used, e.g. SEQ ID NO: 9 to SEQ ID NO: 15.

Figure 16:
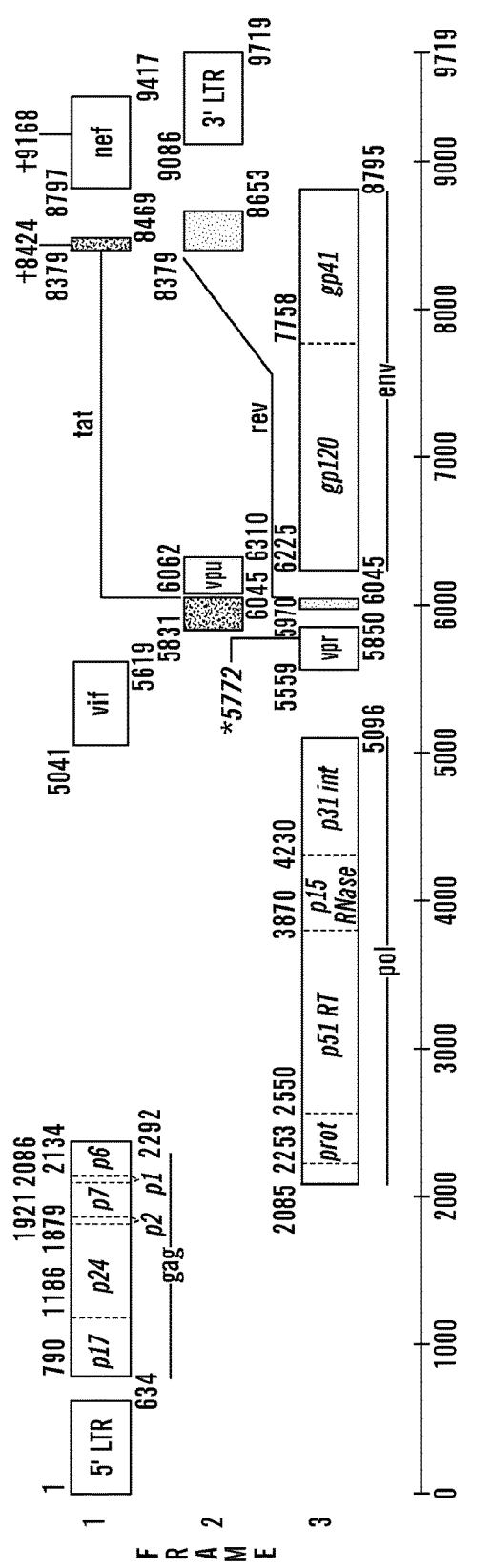
FIG. 16 is adapted from Landmarks of the HIV-1 genome HXB2 (K03455) an exemplary schematic depicting of the open reading frames of the HIV genome, which are shown as rectangles. HIVHXB2CG is a 9719 bp RNA complete genome; The complete genome is found at GENBANK ACCESSION K03455; gene ID GI:1906382. The gene start, indicated by the small number in the upper left corner of each rectangle, normally records the position of the a in the ATG start codon for that gene, while the number in the lower right records the last position of the stop codon. For pol, the start is taken to be the first T in the sequence TTTTTTAG, which forms part of the stem loop that potentiates ribosomal slippage on the RNA and a resulting −1 frameshift and the translation of the Gag-Pol polyprotein. The tat and rev spliced exons are shown as shaded rectangles. In HXB2, *5772 marks position of frameshift in the vpr gene caused by an "extra" T relative to most other subtype B viruses; !6062 indicates a defective ACG start codon in vpu; †8424, and †9168 mark premature stop codons in tat and nef. See Korber et al., Numbering Positions in HIV Relative to HXB2CG, in the database compendium, Human Retroviruses and AIDS, 1998.

Any mRNA sense coding sequence of gag, pol, VPr2, vpr1, vpu, gp160, or vif can be used, and can be determined by those of skill in the art. A representative genomic HIV sequence is given herein as SEQ ID NO: 28, FIG. 16 of the specification describes the location of the mRNA coding sequences. The portion of the mRNA coding sequence used is typically at least 18 nts in length and less than 30 nts. One of skill in the art can also design antisense to any of the mRNA coding sequence of HIV (SEQ ID NO: 28 and FIG. 16), for example to generate the suicide contrast agents and detection agents described herein.

In one embodiment, the mRNA coding sequence of the HIV genome is a vif mRNA coding sequence. In one embodiment, the vif mRNA coding sequence comprises SEQ ID NO: 57.

In certain embodiments, the sequence of a) (i.e. the neural target DNA nucleotide sequence that targets a sequence in the neural cell) is separated from the sequence of b) (i.e. the mRNA coding sequence of the HIV genome) by a separation linker. The linker sequence comprises nucleotides, but typically not greater than about 19 or 20 nucleotides. In one embodiment the linker is about 10 to about 20 nucleotides. In one embodiment, for the separation linker a random sequence not present in the mammalian cells can be used, e.g. RAN, SEQ ID NO: 27 or SEQ ID NO: 26. In one embodiment the separation linker is ATCTACATTAT (SEQ ID NO: 24).

In one embodiment the sODN further comprises a linker for attachment of delivery vehicle, e.g. a superparamagnetic iron oxide nanoparticle (SPIO). In one embodiment the linker for attachment to the delivery vehicle is the nucleotide sequence CCT (SEQ ID NO: 25).

In one embodiment, the sODN comprises a) a nucleotide sequence that targets gfap mRNA and b) a mRNA coding sequence of vif, and wherein the sODN comprises a sequence selected from the group consisting of SEQ ID NO: 16, SEQ ID NO: 17, SEQ ID NO: 18, SEQ ID NO: 19, SEQ ID NO: 20, and SEQ ID NO: 21.

For mice sODN "+HIVvif-rgfap", 56 nucleotides is CCT/GACCAGGCAGACCACTAATTC/ATCTACATTAT/TGA-TACGTCTCCGCT CCATC is SEQ ID NO: 16.

sODN "–HIVvif-rgfap" 56 nucleotides is CCT/CTGGTCCGTCTGGTTGTTAAG/ATCTACATTAT/TGA-TACGTCTCCGCT CCATC is SEQ ID NO: 17.

sODN "+HIVvif+rgfap"56 nucleotides is CCT/GACCAGGCAGACCACTAATTC/ATCTACATTAT/GATG-GAGCGGAGAC GTATCA is SEQ ID NO: 18.

For mouse brains sODN (hivT531gfap, and control HIV(– or a)T532gfap GTCTCCGCTCCATCCTGCCC is SEQ ID NO: 19.

sODN+HIVvif-mgfap is 56 nucleotides CCT/GACCAG-GCAGACCAACTAATTC/ATCTACATTAT/GTCTC-CGCTCCATC CTGCCC is SEQ ID NO: 20.

sODN –HIVvif-mgfap is 56 nucleotides CCT/CTGGTC-CGTCTGGTTGATTAAG/ATCTACATTAT/GTCTC-CGCTCCATC CTGCCC is SEQ ID NO: 21. Space/–HIVvif in (minus strand of HIV)/spacer/targeting sequence to mouse gfap mRNA]

In one embodiments the sODN comprises a) a nucleotide sequence that targets Oct4 mRNA and b) a mRNA coding sequence of vif, and wherein the sODN comprises a sequence selected from SEQ ID NO: 22 or SEQ ID NO: 23.

sODN+hivvif-Oct4 is 56 nucleotides CCT/GACCAG-GCAGACCAACTAATTC/ATCTACATTAT/TCTGGCGC-CGGTT ACAGAAC (SEQ ID NO 22)

sODN hivvif-Oct4 is 56 nucleotides CCT/CTGGTC-CGTCTGGTTGATTAAG/ATCTACATTAT/TCTGGCGC-CGGTTA CAGAAC (SEQ ID NO: 23).

In one embodiment, the superparamagnetic iron oxide nanoparticle (SPIO) is linked to the phosphorothioate-modified oligodeoxynucleotide (sODN) by a Schiff-base linkage (See Example). In one embodiment, the superparamagnetic iron oxide nanoparticle (SPIO) linked to the phosphorothioate-modified oligodeoxynucleotide (sODN) by an avidin-biotin linkage (See Example).

In one embodiment the neural cell is in vitro. In one embodiment, the neural cell is in vitro in tissue, e.g. a brain tissue segment. In one embodiment, the neural cell is in a population of neural cells in culture, thereby creating an in vitro model system for latent HIV reservoir infection (See Examples).

Also provided herein are the neural cells produced by the method of contacting the neural cells with the sODNs of the invention. In certain embodiments, the neural cell is in vivo in a non-human animal, thereby generating an animal model of latent HIV reservoir infection. Any mammal wherein the sODN's are administered can serve as the animal model system. For example, in one embodiment, the non-human animal is selected from the group consisting of a rat, a mouse, and a rhesus macaque.

Accordingly, another aspect of the invention is a neural cell [in vitro or in vivo] comprising a phosphorothioate-modified oligodeoxynucleotide (sODN), wherein the sODN comprises a) a neural target DNA nucleotide sequence that targets a sequence in the neural cell and b) a mRNA coding sequence of the HIV genome.

In certain embodiments the sequence of a) is separated from the sequence of b) by a linker. In one embodiment the separation linker is ATCTACATTAT (SEQ ID NO: 24). In one embodiment the sODN further comprises a linker for attachment of delivery vehicle, e.g. a superparamagnetic iron oxide nanoparticle (SPIO). In one embodiment the linker for attachment to the delivery vehicle is the nucleotide sequence CCT (SEQ ID NO: 25).

In certain embodiments, the neural cell comprises sODN as described where the neural target DNA nucleotide sequence is an antisense sequence ("–" strand) that targets mRNA of a protein selected from the group consisting of, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

In certain embodiments, the neural cell comprises sODN as described where the neural target DNA sequence is a sense sequence ("+" stand) that targets the transcribe strand of genomic DNA, selected from the group consisting of, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

In certain embodiments, the neural cell comprises sODN as described where the neural target DNA sequence targets gfap mRNA.

In certain embodiments, the neural cell comprises sODN as described where the gfap comprises a "–" strand sequence selected from the group consisting of SEQ ID NO: 1, SEQ ID NO: 2 and SEQ ID NO: 3.

In certain embodiments, the neural cell comprises sODN as described where the neural target DNA sequence targets gfap genomic DNA. In certain embodiments, the neural cell comprises sODN as described where the neural target DNA sequence targets gfap genomic DNA is selected from ("+") strand SEQ ID NO: 4, SEQ ID NO: 5 and SEQ ID NO: 6.

In certain embodiments, the neural cell comprises sODN as described where the neural target DNA sequence that targets gfap genomic DNA comprises SEQ ID NO: 7 or SEQ ID No: 8 of human glioma cells.

In certain embodiments, the neural cell comprises sODN as described where the mRNA coding sequence of the HIV genome is selected from the group consisting of gag, pol, VPr2, vpr1, vpu, gp160, or vif. In certain embodiments the mRNA coding sequence is selected from the group consisting of the "+" sense sequences of HIV-gag sequence, 21 nucleotides TCAACTGTGGCAAGGAAGGAC (SEQ ID NO: 51); HIV-pol sequence, 21 nucleotides GGAAAGGT-GAAGGGGCAGTAG (SEQ ID NO: 52); HIV-Vpr2 sequence, 20 nucleotides GGGTGCCAACATAGCAGAAA (SEQ ID NO: 53); HIV-Vpr1 sequence, 21 nucleotides GCTCCATGGCTTAGGACAGTA (SEQ ID NO: 54); HIV-Vpu sequence, 21 nucleotides AGCAGCCATAGTTGT-GTGGAT (SEQ ID NO: 55); HIV-Gp160 sequence, 21 nucleotides TAGGGCAAAGAGTTGGTAGGG (SEQ ID NO: 56); and HIV-vif sequence, 21 nucleotides CTTAACAACCAGACGGACCAG (SEQ ID NO: 57)

In certain embodiments, the neural cell comprises sODN as described where the mRNA coding sequence of the HIV genome is a vif mRNA coding sequence.

In certain embodiments, the neural cell comprises sODN as described where the vif mRNA coding sequence comprises SEQ ID NO: 57.

In certain embodiments, the neural cell comprises an sODN that comprises a) a nucleotide sequence that targets gfap mRNA and b) a mRNA coding sequence of vif, and wherein the sODN comprises a sequence selected from the group consisting of SEQ ID NO: 16, SEQ ID NO: 17, SEQ ID NO: 18, SEQ ID NO: 19, SEQ ID NO: 20, and SEQ ID NO: 21.

In certain embodiments, the neural cell comprises an sODN that comprises a) a nucleotide sequence that targets Oct4 mRNA and b) a mRNA coding sequence of vif, and wherein the sODN comprises a sequence selected from SEQ ID NO: 22 or SEQ ID NO: 23.

In certain embodiments, the neural cell is selected from the group consisting of a glial cell, a neuron, a pericyte (neural progenitor cell) and a cell of the epithelia of the neurovascular unit.

In certain embodiments, the neural cell that comprises an sODN as described is in vivo. Accordingly, also provided are non-human mammal models of HIV reservoirs (latent HIV infection). In certain embodiments, the non-human animal is selected from the group consisting of a rat, a mouse, and a rhesus macaque.

MRI Contrast Agents and Detection Agents

The sODNs described herein can be coupled to any MRI contrast agent. There are two types of contrast agents useful for MRI imaging: T1 and T2 agents. The presence of T1 agent, such as manganese and gadolinium, reduces the longitudinal spin-lattice relaxation time (T1) and results in localized signal enhancement in T1 weighted images. On the other hand, the presence of a strong T2 agent, such as iron, will reduce the spin-spin transverse relaxation time (T2) and results in localized signal reduction in T2 weighted images. Optimal MRI contrast can be achieved via proper administration of contrast agent dosage, designation of acquisition parameters such as repetition time (TR), echo spacing (TE) and RF pulse flip angles.

Specific examples of such magnetic nanoparticles include MIONs as described, e.g., in U.S. Pat. No. 5,492,814; Whitehead, U.S. Pat. No. 4,554,088; Molday, U.S. Pat. No. 4,452,773; Graman, U.S. Pat. No. 4,827,945; and Toselson et al., Bioconj. Chemistry, 10:186-191 (1999), superparamagnetic iron oxide particles (SPIOs), SPIONs, USPIOs, and CLIO particles (see, e.g., U.S. Pat. No. 5,262,176). Some of these products are available on the market, such as Feridex IV®, Abdoscan® and Lumirem® as contrast agents. Superparamagnetic agents may be magnetized more than paramagnetic agents due to their ca. 1000 times higher magnetic moment, which provides a higher relaxivity (Andre E. Merbach and Eva Toth (Eds.), *The Chemistry of Contrast Agents in Medicinal Magnetic Resonance Imaging*, Wiley, New York, 2001, p. 38; ISBN 0471607789). Superparamagnetic iron oxide crystalline structures have the general formula $[Fe_2^{3+}O_3]x[Fe_2^{3+}O_3(M2^+O)]1-x$ where $1 \geq x \geq 0$. M2+ may be a divalent metal ion such as iron, manganese, nickel, cobalt, magnesium, copper or a combination thereof. When the metal ion (M2+) is ferrous ion ($Fe^{2+}$) and x=0, the SPIO agent is magnetite ($Fe^3O_4$), and when x=1, the SPIO agent is maghemite ($\gamma$-$Fe_2O_3$).

Paramagnetic and superparamagnetic materials or ferromagnetic contrast agents for MRI are also described in: AE Merbach and Toth E. 2001, The Chemistry of Contrast Agents in Medical Magnetic Resonance Imaging, 2001, John Wiley & Sons. Paramagnetic contrast agents based substances include small gadolinium chelates (III) (Gd-DTPA, Gd-DTPA-BMA, Gd-DOTA, Gd-DO3A) (E. Toth et al., The Chemistry of Contrast Agents in Medical Magnetic Resonance Imaging 2001, John Wiley & Sons, 45) and contrast agents based on superparamagnetic nanoparticles of iron oxide core with very small (<30A-USPIO ultrasmall superparamagnetic iron oxide particles), or small (<200A, rum superparamagnetic SPIO-oxide) (RN Muller et al., The Chemistry of Contrast Agents in Medical Magnetic Resonance Imaging, 2001, John Wiley & Sons, 417). Paramagnetic agents induce an increase in image intensity in MRI T1 weighted sequences (positive contrast enhancement) and superparamagnetic agents induced a decrease in the magnetic resonance signal is T2-weighted sequences (negative contrast enhancement). The contrast agent can be coupled (linked) to either the 5' or 3' ends of the sODN to AS-ODN, either covalently or non-covalently.

For detection, the sODNs described herein can be conjugated to a reporter labels, for example cy3 or cy5. Labels and methods of conjugating are well known to those of skill in the art, See Examples herein, See also Liu et al., Ann Neurol., 36:566-76, 1994; and Cui et al., J. Neurosci., 19:1335-44, 1999; Sandberg et al., J. Neuro-Oncology, 58:187-192, 2002; and Liu et al., Magn. Reson. Med. 51:978-87, 2004, incorporated by reference in their entirety.

One aspect of the invention provides suicide MRI contrast agent that selectively kills cells harboring HIV. These suicide MRI contrast agents comprise a) a toxic magnetic resonance imaging (MRI) contrast agent linked to b) an antisense phosphorothioate-modified oligodeoxynucleotide (AS-sODN), wherein an AS-ODN comprises a nucleotide sequence that binds to a mRNA coding sequence of the HIV genome. In certain embodiments, the toxic agent is gadolinium, a T1 agent, or a contrast agent used in CEST e.g. chemical exchange saturation transfer, such as Gadolinium III or lanthanide III ions. These agents are slightly negative charged for interaction with cell membrane and is internalized by endocytosis within living cells.

In one embodiment, the suicide agent comprises an AS-sODN that targets an HIV mRNA coding sequence selected from the group consisting of gag, pol, VPr2, vpr1, vpu, gp160, or vif. Any sequence of the HIV coding sequence can be targeted. See for Example the HIV genome of SEQ ID NO: 28 and FIG. 16. In certain embodiments, the AS-sODN comprises a nucleotide sequence selected from the group consisting of: SEQ ID NO: 9. SEQ ID NO: 10, SEQ ID NO: 11, SEQ ID NO: 12, SEQ ID NO: 13, SEQ ID NO: 14, SEQ ID NO: 15. The HIV-gag sequence is 21 nucleotides GTC-CTTCCTTGCCACAGTTGA (SEQ ID NO: 9); The HIV-pol sequence is 21 nucleotides CTACTGCCCCTTCAC-CTTTCC (SEQ ID NO: 10); The HIV-Vpr2 sequence is 20 nucleotides TTTCTGCTATGTTGGCACCC (SEQ ID NO: 11); The HIV-Vpr1 sequence is 21 nucleotides TACTGTC-CTAAGCCATGGAGC (SEQ ID NO: 12); The HIV-Vpu sequence is 21 nucleotides ATCCACACAACTATGGCT-GCT (SEQ ID NO: 13); The HIV-Gp160 sequence is 21 nucleotides CCCTACCAACTCTTTGCCCTA (SEQ ID NO: 14); and HIV-vif sequence, 21 nucleotides CTGGTC-CGTCTGGTTGTTAAG (SEQ ID NO: 15)—

The suicide contrast agents described herein that selectively kill cells harboring HIV comprise a toxic MRI contrast agent linked to an AS-ODN that binds to the coding sequence of HIV. In certain embodiments, the toxic MRI contrast agent comprises gadolinium III ($Gd^{3+}$) or Lanthanide ($Ln^{3+}$). In one embodiment, the toxic agent is selected from the group consisting of gadolinium ($Gd^{3+}$), dysprosium ($Dy^{3+}$), and from agents that are used for paracest contrast.

In one embodiment, the sODNs described herein are coupled to SPIO contrast agents, (e.g. detection agents). In one embodiment, the sODNs described herein are coupled to SPIO and to a toxic agent, such as Gd, and are used as suicide contrast agents. In one embodiment, the sODNs described herein are coupled to the toxic MRI contrast agent only, e.g. gadolinium III ($Gd^{3+}$) or Lanthanide ($Ln^{3+}$), and is not to SPIO.

In certain embodiments, the AS-ODNs that targets an HIV mRNA coding sequence, e.g. SEQ ID NO's: 9 to 15, is coupled (linked) to a superparamagnetic iron oxide nanoparticle, and used as a detection reagent, e.g. for the detection of latent viral reservoirs in the brain. Superparamagnetic iron oxide nanoparticles (SPIO) are well known in the art as MRI contrast agents and are further described in U.S. Patent Application 2007/0140974. In certain embodiments, the detection conjugate further comprises a reporter, e.g. Cy-5 or the like.

In certain embodiments, the superparamagnetic iron oxide nanoparticle (SPIO) is linked to the phosphorothioate-modified oligodeoxynucleotide (sODN) by a Schiff-base linkage (See Example).

In certain embodiments, the superparamagnetic iron oxide nanoparticle (SPIO) linked to the phosphorothioate-modified oligodeoxynucleotide (sODN) by an avidin-biotin linkage (See Example), methods of avidin biotin linkage are well known to those of skill in the art.

Figure 18A:
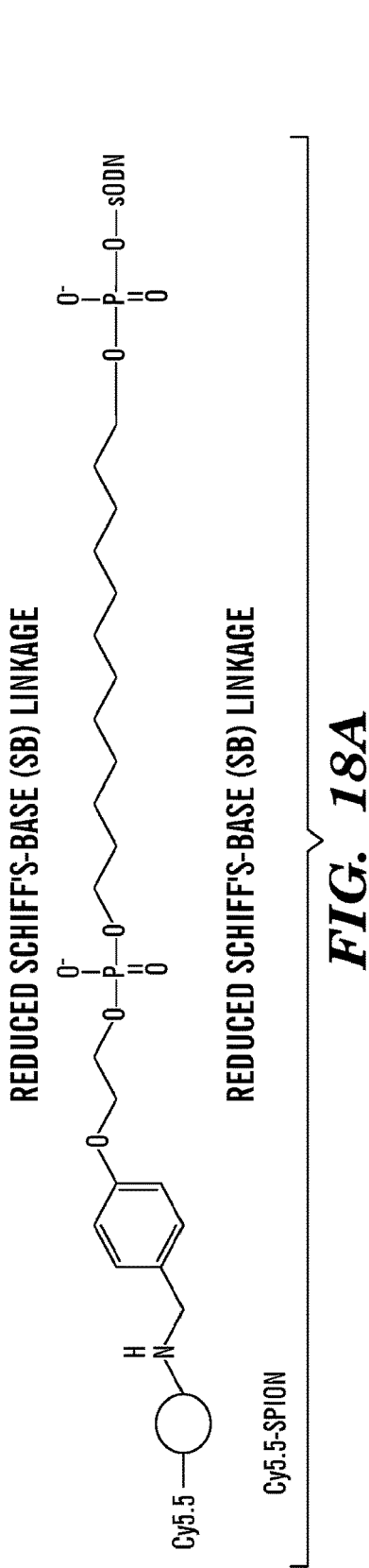
FIGS. 18A and 18B are compounds.
Figure 18B:
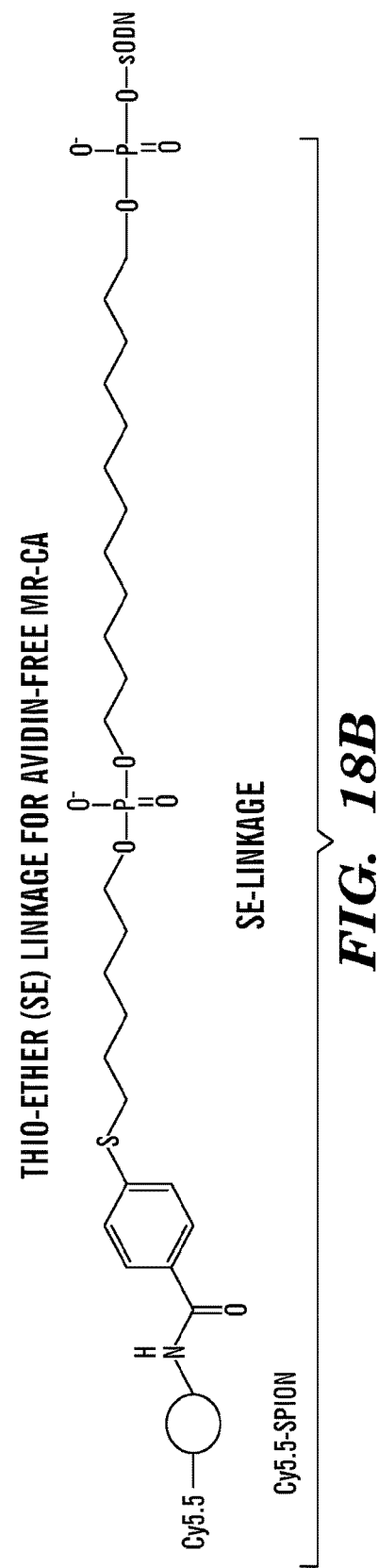

We have also generated avidin-free linkages in magnetic resonance (MR) contrast agents (CA): The MR-CA prototype uses NeutrAvidin (NA)-biotin conjugation; we have generated a second generation CAs using amines (on Dextran coating of SPION) and aldehyde in sODN via Schiff-base (SB) reaction (a NA-free MR-CA) to promote future use in humans (See FIGS. 18A & 18B). We compared SPION-SB-actin (our new NA-free MR-CA) and its application to image pericytes to that of SPION-NA-action, the prototype with NA MR-CA, See Liu et al. 2013, except a higher dose of SPION-SB-actin is needed than the prototype MR-CA (Liu C H, Yang J, Ren J Q, Liu C M, You Z, Liu P K (2013) MRI reveals differential effects of amphetamine exposure on neuroglia in vivo. FASEB journal: official publication of the Federation of American Societies for Experimental Biology 27:712-724).

We compared SPION-NA-actin (n=2, 2494 & 2500) and SPION-SB-actin (n=3, 2496, 2497, & 2499) targeting α-actin mRNA of pericytes in the subventricular zone (SVZ) to mice after cerebral ischemia (BCAO-60) using R2* maps by MRI (Liu et al., 2012). Color scale (below the R2* maps) shows R2* values (red to yellow=70–100 R2*) in which significant elevation of R2* values above baseline expression were observed, (data not shown). We conclude that SPION-SB-sODN can be as effective as SPION-NA-sODN (i.p.=intraperitoneal injection). The same is found for SPION-SE-actin (thioether linkage). The significance of this new MR-CA is to reduce immunoreaction in humans, therefore, this new MR-CA will have high impact for future human use.

Delivery of Contrast Agents

The suicide contrast agent or detection agents that hybridize to a portion of the HIV genome can be administered by delivery to the brain. To be delivered to the brain, one can use convection-enhanced delivery to the cerebral ventricles such as to the lateral ventricle (Liu et al., Ann Neurol., 36:566-76, 1994; and Cui et al., J. Neurosci., 19:1335-44, 1999) or the 4th ventricles (Sandberg et al., J. Neuro-Oncology, 58:187-192, 2002). Delivery can also be intrathecal (Liu et al., Magn. Reson. Med. 51:978-87, 2004) or by any additional routes that lead directly or indirectly to brain cells. The general methodology is described in detail in WO 2006/023888. See also the Examples described herein.

In certain embodiments, the suicide agent (beacon) can be administered using intracranial injection (icy route) for homogenous distribution. In certain embodiments delivery can be done by intraperitoneal (i.p.) injection. The suicide agents, (e.g. Gd-[-]-hiv-vif, a cytotoxic T1 contrast agent) may additionally be linked to, Adriamaycin, Doxil or Myocet for enhanced eradication of host cells. Thus, in certain embodiments, the suicide MRI contrast agent is further linked to Adriamaycin, Doxil or Myocet.

Methods for determining targeted drug delivery in latent HIV infection (i.e. HIV reservoirs) in a subject are also provided. The method comprises administering to a subject the suicide MRI contrast agent that selectively kills cells harboring HIV and treating subject with magnetic resonance. In certain embodiments these sODNs for testing are selected from the following (HIV–gag, HIV–pol, HIV–Vpr2, HIV–Vpr1, HIV–Vpu, HIV–gp160 and HIV–vif) and (HIV+gag, HIV+pol, HIV+Vpr2, HIV+Vpr1, HIV+Vpu, HIV+gp160 and HIV+vif) which are linked to Gd3+, Dy3+ or Ln3+(no need for cellular mRNA targeting).

Methods of reducing latent HIV infection in a subject are also provided. The methods comprise administering to a subject the suicide MRI contrast agent that selectively kills cells harboring HIV, and treating subject with magnetic resonance.

For administration, e.g., to an experimental rodent, Maquaqe, or human patient, the conjugate contrast agent (e.g. suicide sODN or detection sODN) can be diluted in a physiologically acceptable fluid such as buffered saline, dextrose or mannitol. Preferably, the solution is isotonic. Alternatively, the conjugate can be lyophilized and reconstituted with a physiological fluid before injection. The conjugate can be administered parenterally, e.g., by intravenous (IV) injection, subcutaneous injection, or intramuscular administration, depending on the tissue to be imaged. For imaging the brain, a useful route of administration is the intracerebroventricular (ICV) route. When administered intravenously (IV) or intraperitoneally (i.p.), the conjugate can be administered at various rates, e.g., as rapid bolus administration or slow infusion.

When administered by IV injection and superparamagnetic iron particles are used as the paramagnetic label, useful dosages are between about 0.1 and 10.0 mg of iron per kg, e.g., between 0.2 and 5 mg/kg for a 1.5 Tesla medical scanner. As is known in this art, there is a field dependence component in determining the contrast dosage. Doses of iron higher than 10 mg/kg should be avoided because of the inability of iron to be excreted. These types of contrast agents can be used at a dosage of 0.001 to 0.1 mg/kg body weight for ICV administration in the rodents.

When administered by IV injection and chelated gadolinium is used as the paramagnetic label, the dose will be between 10 micromoles and 1000 micromoles gadolinium/kg, e.g., between 50 and 100 micromoles gadolinium/kg. Doses above 1000 micromoles/kg produce hyperosmotic solutions for injection In certain embodiments, the reduction in latent reservoirs is determined by first using a detection agent AS-ODN to detect the HIV reservoirs, and an area map determined, and positive reservoirs quantitated (see examples), this value can be compared to detection levels after treatment with the suicide agent. Treatment has occurred for example when there is decrease in latent virus detected, e.g. as indicated at a decrease of about 10%, about 30%, about 50%, about 60%, about 70%, about 80%, or more, as compared to frequency observed prior to treatment.

In some embodiments of the present invention may be defined in any of the following numbered paragraphs:

Paragraph 1. A neural cell comprising a phosphorothioate-modified oligodeoxynucleotide (sODN), wherein the sODN comprises a) a neural target DNA nucleotide sequence that targets a sequence in the neural cell and b) a mRNA coding sequence of the HIV genome.

Paragraph 2. The neural cell of paragraph 1, wherein the neural target DNA nucleotide sequence is an antisense sequence ("−" strand) that targets mRNA of a protein selected from the group consisting of Ran, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

Paragraph 3. The neural cell of any of paragraphs 1-2, wherein the neural target DNA sequence is a sense sequence ("+" stand) that targets the transcribe strand of genomic DNA, selected from the group consisting of Ran, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

Paragraph 4. The neural cell of paragraph 2, wherein the neural target DNA sequence targets gfap mRNA.

Paragraph 5. The neural cell of paragraph 4, wherein the gfap comprises a "−" strand sequence selected from the group consisting of SEQ ID NO: 1, SEQ ID NO: 2 and SEQ ID NO: 3.

Paragraph 6. The neural cell of paragraph 3, wherein the neural target DNA sequence targets gfap genomic DNA.

Paragraph 7. The neural cell of paragraph 5 or paragraph 6, wherein the neural target DNA sequence that targets gfap genomic DNA comprises SEQ ID NO: 7 or SEQ ID No: 8 of human glioma cells.

Paragraph 8. The neural cell of any of paragraphs 1-6, wherein the mRNA coding sequence of the HIV genome is selected from the group consisting of gag, pol, VPr2, vpr1, vpu, gp160, or vif.

Paragraph 9. The neural cell of paragraph 8, wherein the mRNA coding sequence of the HIV genome is a vif mRNA coding sequence.

Paragraph 10. The neural cell of paragraph 9, wherein the vif mRNA coding sequence comprises SEQ ID NO: 57.

Paragraph 11. The neural cell of paragraph 1, wherein the sODN comprises a) a nucleotide sequence that targets gfap mRNA and b) a mRNA coding sequence of vif, and wherein the sODN comprises a sequence selected from the group consisting of SEQ ID NO: 16, SEQ ID NO: 17, SEQ ID NO: 18, SEQ ID NO: 19, SEQ ID NO: 20, and SEQ ID NO: 21.

Paragraph 12. The neural cell of paragraph 1, wherein the sODN comprises a) a nucleotide sequence that targets Oct4 mRNA and b) a mRNA coding sequence of vif, and wherein the sODN comprises a sequence selected from SEQ ID NO: 22 or SEQ ID NO: 23.

Paragraph 13. The neural cell of any of paragraphs 1-12, wherein the superparamagnetic iron oxide nanoparticle (SPIO) is linked to the phosphorothioate-modified oligodeoxynucleotide (sODN) by a Schiff-base linkage.

Paragraph 14. The neural cell of any of paragraphs 1-13, wherein the superparamagnetic iron oxide nanoparticle (SPIO) linked to the phosphorothioate-modified oligodeoxynucleotide (sODN) by an avidin-biotin linkage.

Paragraph 15. The neural cell of any of paragraphs 1-14, wherein the neural cell is in vitro.

Paragraph 16. The neural cell of paragraph 15, wherein the neural cell is in a population of neural cells in culture.

Paragraph 17. The neural cell of any of paragraphs 1-14, wherein the neural cell is in vivo.

Paragraph 18. The neural cell of any of paragraphs 1-17, wherein the neural cell is selected from the group consisting of a glial cell, a neuron, a pericyte (neural progenitor cell) and a cell of the epithelia of the neurovascular unit.

Paragraph 19. A cell culture comprising the neural cell of any of paragraphs 1-18.

Paragraph 20. A non-human mammal comprising the neural cell of any of paragraphs 1-19.

Paragraph 21. The non-human mammal of paragraph 20, wherein the non-human animal is selected from the group consisting of a rat, a mouse, and a rhesus macaque.

Paragraph 22. A suicide contrast agent that selectively kills cells harboring HIV comprising a) a toxic magnetic resonance imaging (MRI) contrast agent linked to b) an antisense phosphorothioate-modified oligodeoxynucleotide (AS-sODN), wherein an AS-ODN comprises a nucleotide sequence that binds to a mRNA coding sequence of the HIV genome.

Paragraph 23. The suicide contrast agent of paragraph 22, wherein the AS-sODN targets an HIV mRNA coding sequence selected from the group consisting of gag, pol, VPr2, vpr1, vpu, gp160, or vif.

Paragraph 24. The suicide contrast agent of paragraph 23, wherein the AS-sODN comprises a nucleotide sequence selected from the group consisting of: SEQ ID NO: 9. SEQ ID NO: 10, SEQ ID NO: 11, SEQ ID NO: 12, SEQ ID NO: 13, SEQ ID NO: 14, SEQ ID NO: 15.

Paragraph 25. The suicide contrast agent of any of paragraphs 23-24 wherein the toxic MRI contrast agent comprises gadolinium III (Gd3+) or Lanthanide (Ln 3+).

Paragraph 26. The suicide contrast agent of paragraph 23-24, wherein the agent is selected from the group consisting of gadolinium ($Gd^{3+}$), dysprosium ($Dy^{3+}$), and agents that are used for paracest contrast.

Paragraph 27. A method for determining targeted drug delivery in latent HIV infection (i.e. HIV reservoirs) in a subject comprising administering to a subject an agent of any of paragraphs 22-26 and treating subject with magnetic resonance.

Paragraph 28. A method of reducing latent HIV infection in a subject comprising administering to a subject an agent of any of paragraphs 22-26 and treating subject with magnetic resonance.

Paragraph 29. A method for generating a model of latent HIV reservoir infection in the central nervous system comprising contacting a neural cell with a superparamagnetic iron oxide nanoparticle (SPIO) linked to a phosphorothioate-modified oligodeoxynucleotide (sODN), wherein the sODN comprises a) a neural target DNA nucleotide sequence and b) a mRNA coding sequence of the HIV genome.

Paragraph 30. The method of paragraph 29, wherein the neural target DNA nucleotide sequence is an antisense sequence ("−" strand) that targets mRNA of a protein selected from the group consisting of Ran, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

Paragraph 31. The method of any of paragraphs 29-30, wherein the neural target DNA sequence is a sense sequence ("+" stand) that targets the transcribe strand of genomic DNA, selected from the group consisting of Ran, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

Paragraph 32. The method of paragraph 30, wherein the neural target DNA sequence targets gfap mRNA.

Paragraph 33. The method of paragraph 32, wherein the gfap comprises a "−" strand sequence selected from the group consisting of SEQ ID NO: 1, SEQ ID NO: 2 and SEQ ID NO: 3.

Paragraph 34. The method of paragraph 31, wherein the neural target DNA sequence targets gfap genomic DNA.

Paragraph 35. The method of paragraph 34, wherein the neural target DNA sequence that targets gfap genomic DNA comprises SEQ ID NO: 7 or SEQ ID No: 8 of human glioma cells.

Paragraph 36. The method of any of paragraphs 29-35, wherein the mRNA coding sequence of the HIV genome is selected from the group consisting of gag, pol, VPr2, vpr1, vpu, gp160, or vif.

Paragraph 37. The method of paragraph 36, wherein the mRNA coding sequence of the HIV genome is a vif mRNA coding sequence.

Paragraph 38. The method of paragraph 37, wherein the vif mRNA coding sequence comprises SEQ ID NO: 57.

Paragraph 39. The method of paragraph 29, wherein the sODN comprises a) a nucleotide sequence that targets gfap mRNA and b) a mRNA coding sequence of vif, and wherein the sODN comprises a sequence selected from the group consisting of SEQ ID NO: 16, SEQ ID NO: 17, SEQ ID NO: 18, SEQ ID NO: 19, SEQ ID NO: 20, and SEQ ID NO: 21.

Paragraph 40. The method of paragraph 29, wherein the sODN comprises a) a nucleotide sequence that targets Oct4 mRNA and b) a mRNA coding sequence of vif, and wherein the sODN comprises a sequence selected from SEQ ID NO: 22 or SEQ ID NO: 23.

Paragraph 41. The method of any of paragraphs 29-40, wherein the superparamagnetic iron oxide nanoparticle (SPIO) is linked to the phosphorothioate-modified oligodeoxynucleotide (sODN) by a Schiff-base linkage.

Paragraph 42. The method of any of paragraphs 29-41, wherein the superparamagnetic iron oxide nanoparticle (SPIO) linked to the phosphorothioate-modified oligodeoxynucleotide (sODN) by a by an avidin-biotin linkage.

Paragraph 43. The method of any of paragraphs 29-42, wherein the neural cell is in vitro.

Paragraph 44. The method of paragraph 43, wherein the neural cell is in a population of neural cells in culture.

Paragraph 45. A population of neural cells produced by the method of paragraph 44.

Paragraph 46. The method of any of paragraphs 29-45, wherein the neural cell is in vivo in a non-human animal.

Paragraph 47. The method of paragraph 46, wherein the non-human animal is selected from the group consisting of a rat, a mouse, and a rhesus macaque.

Paragraph 48. An animal model of HIV reservoirs produced by the method of any of paragraphs 29-42 and paragraphs 46-47.

Paragraph 49. A neural cell comprising a phosphorothioate-modified oligodeoxynucleotide (sODN), wherein the sODN comprises a) a neural target DNA nucleotide sequence that targets a sequence in the neural cell and b) a mRNA coding sequence of a viral genome.

Paragraph 50. The neural cell of paragraph 49, wherein the neural target DNA nucleotide sequence is an antisense sequence ("−" strand) that targets mRNA of a protein selected from the group consisting of Ran, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

Paragraph 51. The neural cell of paragraph 49, wherein the neural target DNA sequence is a sense sequence ("+" stand) that targets the transcribe strand of genomic DNA, selected from the group consisting of Ran, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

Paragraph 52. The neural cell of any of paragraphs 49-51, wherein the neural target DNA sequence targets gfap and comprises a sequence selected from the group consisting of SEQ ID NO: 1, SEQ ID NO: 2 and SEQ ID NO: 3, SEQ ID NO: 7 and SEQ ID No: 8.

Paragraph 53. A method for generating a model of latent HIV reservoir infection in the central nervous system comprising contacting a neural cell with a superparamagnetic iron oxide nanoparticle (SPIO) linked to a phosphorothioate-modified oligodeoxynucleotide (sODN), wherein the sODN comprises a) a neural target DNA nucleotide sequence and b) a mRNA coding sequence of a viral genome.

Paragraph 54. The method of paragraph 53, wherein the neural target DNA nucleotide sequence is an antisense sequence ("−" strand) that targets mRNA of a protein selected from the group consisting of Ran, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

Paragraph 55. The method of any of paragraphs 53-54, wherein the neural target DNA sequence is a sense sequence ("+" stand) that targets the transcribe strand of genomic DNA, selected from the group consisting of Ran, cFos, actin, FosB, deltafosB, matrix metalloproteinase-9 (mmp9), nestin, gilal fibrillary acidic protein (gfap), histones deacetylase 5 (hdac5AS2), ionized calcium-binding adaptor molecule 1 or allograft inflammatory factor (AIF) (1lba1), and octamer-binding transcription factor 4 (OCT4).

Paragraph 56. The method of any of paragraphs 53-55, wherein the neural target DNA sequence targets gfap and comprises a sequence selected from the group consisting of SEQ ID NO: 1, SEQ ID NO: 2 and SEQ ID NO: 3, SEQ ID NO: 7 and SEQ ID No: 8.

Paragraph 57. The neuronal cell of any of paragraphs 49-56, wherein the neural cell is in vitro.

Paragraph 58. The neuronal cell of any of paragraphs 49-56, wherein the neural cell is in vivo.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLE 1

Suicide Contrast Agents Targeting HIV Reservoir for Theranostic Eradication

Human immunodeficiency virus (HIV) causes acquired immuno-deficiency syndrome (AIDS). Although antiviral therapies including stem cell transplant effectively suppress HIV below the limit of detection by clinical assays available and diminish AIDS, recurrence of AIDS has been reported due to latent virus (HIV reservoir) in the body. We have delivered specific magnetic resonance (MR) contrast agents to cells expressing unique RNA in living brains with a similar specificity and sensitivity to RT-PCR; one of such contrast agent kills PC12 cells that harbor a partial HIV genome. We will deliver suicide contrast agents to cells that harbor the recombinant HIV genome in living mice or rhesus macaques (*Macaca mulatta*) and examine the potential to eradicate viral reservoir in vivo.

Host cells for latent human immuno-deficiency virus (HIV) may express HIV RNA or proteins at levels undetectable by existing methods. Such latent HIV (reservoirs) are sequestered in microglia and astroglia of the brain and can be activated without new HIV infection. We have reported neural cell targeting magnetic resonance imaging (MRI) in living brains of C57/black6 mice, and validated by optical and transmission electron microscopies (TEM, for iron oxide) postmortem. This MR technique is based on nucleic acid hybridization and reports RNA at very low levels without biopsy (from one to more than 2500 copies per $10^{-9}$ gram RNA by TaqMan analysis, linear regression of correlation=$r^2 \geq 0.9$). We can (1) detect HIV or SIV with the specificity similar to those of RT-PCR and (2) deliver toxic molecules to eradicate host cells with HIV or SIV genome. We have synthesized a phosphorothioate-modified DNA (sODN) that has recombinant reservoirs (partial viral infectivity factor (vif) RNA, [+]hiv-vif or [+]-siv-vif, 36 nucleotides [nts]) and an antisense (AS) sODN (20 nts) to glial fibrillary acidic protein (gfap) mRNA in the host cells. We also generated a sODN with negative sequence of vif RNA ([−]-hiv-vif or [−]-siv-vif, 20 nts) to target sODN of reservoir; the sODN [−]-hiv-vif is linked to a cyanine (Cy)-5.5 labeled superparamagnetic iron oxide nanoparticle (SPION, a biocompatible T2 MR susceptibility agent) with Schiff base as a beacon for MRI. We showed PC12 cells retained this recombinant HIV reservoir, which was detected by SPION-[−]-hiv-vif. When linked to gadolinium (Gd, a T1 agent), Gd-[−]hiv-vif (Gd=28 nmole per ml) inhibited 50% colony-forming ability in PC12 harboring the reservoir (p=0.03, n=2). This strategy has been translated to the brain of C57black6 mice (n=4).

Background, Impact, Challenge and Significance:

HIV is an RNA virus that infects only humans. Sharing needles or other devices used for drug injection and engaging in high-risk sexual behaviors with infected individuals are two main ways to acquire HIV infection. Infected pregnant women can pass HIV to their babies during pregnancy, delivery and breastfeeding. HIV destroys CD4+ cells in the immune system and compromises the body's disease fighting abilities (or acquired immune deficiency syndrome [AIDS]). Human antibodies against HIV by enzyme-linked immunosorbent assay (ELISA) and Western blot are currently used for HIV tests but the results may not be accurate for someone who just gets infected or new born babies who may carry antibodies from mothers.

There are currently 31 antiviral drugs approved by the Food and Drug Administration to treat HIV infection. These drugs are inhibitors of reverse transcriptase, of protease, or of enzymes for fusion/entry of HIV. Gene knockdown using antisense DNA and RNAi is in the pipeline. Multidrug combination products or highly active antiretroviral therapies (HAART), in addition to transplantation of HIV-resistant stem cells from CCR5-Δ32 individuals, have been proven effective for suppressing HIV and halting disease progression. However, none of these is a cure; HIV reservoirs containing the viral genome may allow recurrence of AIDS if the therapy is stopped. In the lysogenic phase, the viral life cycle persists even though new virus is not actively produced; resting $CD4^+$ T cells serve as reservoirs for latent HIV. Although the number of viral transcripts is below detection limits (or transcripts below the detection limit of standard clinical assays), the virus genome remains intact (Lin et al., 2003), enabling the latent virus to reactivate and produce viral progeny without new infection (Kovochich et al., 2011).

HIV-1 also infects macrophages, astroglia and microglia among other T cells. The infected/activated macrophages traffic the virus through the BBB into the brain early after infection (Fischer-Smith et al., 2008). Latent virus can be located in the microglia of the brain and a recurrence of AIDS has been reported. Although most studies have indicated that the virus does not infect neurons, neurons can be injured, and subsequently die, as a byproduct of infection. Neuronal injury may be caused either directly by overstimulation of viral protein, which leads to free radical formation similar to that in neurodegenerative disorders, or indirectly by toxins released from infected microglia and macrophages. Therefore, HIV-1 can also induce dementia. To eradicate the HIV reservoir will significantly impact health care (Namanja et al., 2012).

Diagnosis from the cerebrospinal fluid (CSF) has been the only source for neurological disorders but titer in the CSF can be diluted and the location of infection is uncertain. However, biopsy of the CNS is not routinely performed for clinical purposes except for therapeutic applications. To determine whether or not a person is free of latent HIV is a challenge, and calls for new strategies for latent HIV detection. The challenge is to develop a theranostic strategy to eradicate brain cells harboring HIV reservoir, especially in the central nervous system (CNS) of living subjects, followed by transplants of stem cell from CCR5-Δ32 individuals. To meet this first challenge, we proposed to deliver toxic molecules to eliminate cells harboring HIV; we have validated the delivery of a RNA-targeting MR contrast agent for the living brains without biopsy (Table 1); this technology deliver large cargo of MR contrast agent (up to 30±20 nanometers in diameter) to cells having unique RNA in living mouse brains which has the sensitivity and specificity of RT-PCR (Liu et al., 2013). Herein, this technology has been applied to delivery of two separated MR contrast agents for imaging and diagnosis (iron oxide a biocompatible T2 susceptability agent), and for eradication (Gd, a T1 agent, but is toxic when it is internalized in cells) (Blank et al., 1986, Song et al., 2009, Dumont et al., 2012).

MRI is a powerful minimally invasive tool for in vivo detection of neural cells in whole body with excellent penetrance. We have developed unique in vivo targeting modality with high specificity and sensitivity to target cells harboring pathological genes in vivo and have applied the one and only technology using T1 and T2 MR contrast agents for neural cells (neurons, astroglia, microglia and neural progenitor cells). The agents can diagnose (imaging beacons) and deliver toxic contrast agent to eliminate cells that harbor the HIV/SIV genome (suicide beacons) in living animals.

This strategy has significant advantages of being less invasive and showing specificity and sensitivity longitudinal applications based on gene targeting in living systems. Being able to eradicate cells harboring viral reservoir in rodents and rhesus macaques (*Macaca mulatta*) in the animal modes described herein, indicates that the technology can be translated to humans with viral infection (clinically).

The imaging modality can also be used to evaluate the VL when viral enzymes are not produced and to demonstrate quantifiably the effectiveness of stem cells replacement therapy. Various strains of simian immunodeficiency virus (SIV) are used in research using the nonhuman primate (NHP) rhesus macaque; NHP-SIV models mimic human HIV latency (Barber et al., 2006).

HP-SIV models have served as excellent models in AIDS research (Clements et al., 2008). Our in vivo gene specific contrast agent can measure the level of VL in SIVmac251 infected NHP-macaques (NHP-SIV models). The VL will be quantitated using phantoms with known concentrations of contrast agent so that the VL by MRI can be correlated with the result from RT-PCR. The correlation can be the index for VL reduction and efficacy evaluation when the suicide beacon is included in CART to NHP-SIV models.

Viral targeting contrast agent has been demonstrated in preliminary studies (FIG. 1). Recombinant DNA with a partial HIV genome can be applied to cell culture and animals for modifications of viral genome-targeting contrast agent. This is a novel approach to apply a partial HIV genome to living brains of rodents and NHP as a reservoir for repeat testing of eradication strategies. A rodent model of acute HIV-1 infection has been recently proposed (Gorantla et al., 2010, Dash et al., 2011), however, it appears that this model may be an acute version of the NHP-SIV model without latency. This HIV reservoir we describe here has a 56-bp sODN consisting of a 36-bp partial vif coding sequence from HIV or SIV genome and a 20-bp sODN with sequence homologous to the transcribed strand of GFAP genome (AS to the mRNA of GFAP). This AS-gfap sODN hybridizes to mRNA in the cytoplasm and to the non-transcribed strand of the gfap gene in the nucleus. The sODN of ASgfap sequestered reservoir sODN to astroglia/microglia to make an intracellular pool (reservoir) of a partial vif gene in the host based on hybridization described previously (Liu et al., 2013). In addition, there are several unique gene targets that are expressed in different neural cells and we have made sODN for targeting (Table 1); the partial HIV reservoir can be transfected to these cells when the need arises for reservoir in different hosts, except the randomized sODN for it will not produce any reservoir and it will be a control. All DNA are modified by phosphorothiate (s-ODN) to protect them from nucleases, and to alter charge for interaction with cell membrane as required for endocytosis (Liu et al., 2008a). Because the reservoir does not have the entire HIV genome, this model is safe for laboratory research without level 2 clearance; the animal with such a reservoir can be used to test the efficacies of imaging or suicide beacons.

TABLE 1

MR visible contrast agents for various cellular mRNA/Protein targeting

| MR visible agents | Target (mRNA/transcription factor protein) | References |
|---|---|---|
| SPION-Ran | Radom or scrambled sequence, no cellular target, a control | (Liu et al., 2007a) |
| SPION-cfos | c-fos mRNA (neurons) | (Liu et al., 2007c) |
| SPION-actin | Actin mRNA (multi-cellular origin) | (Liu et al., 2007b) |
| SPION-fosB | fosB mRNA (neurons) | (Liu et al., 2009a) |
| SPION-ΔfosB | Delta-fosB mRNA (truncated FosB mRNA) | (Liu et al., 2009a) |
| SPION-mmp9 | matrix metalloproteinase-9 (mmp-9) mRNA (BBB leakage) | (Liu et al., 2009b) |
| SPION-nestin | Nestin mRNA (pericytes, neuroglia) (angiogenesis) | (Liu et al., 2012) |
| SPION-gfap | Glial fibrillary acidic protein (GFAP) mRNA (gliogenesis) | (Liu et al., 2008a, Liu et al., 2013) |
| SPION-hdac5AS2 | HDAC5 mRNA (no known binding of miRNAs) | (Liu et al., 2013) |
| SPION-iba1 | IBA1 mRNA (activated microglia) | In progress |
| sODN-[+]hiv-vif-ASgfap | Reservoir of partial hiv vif coding sequence in asgroglia | This project We use [+] to denote RNA in the cytoplasm. |
| sODN-[+]hiv-vif-ASiba1 | Reservoir of partial hiv vif coding sequence in activated microglia | This project |
| SPION-[−]hiv-vif | Contrast agent for partial vif coding sequence in the hiv reservoir | This project |

TABLE 1-continued MR visible contrast agents for various cellular mRNA/Protein targeting

| MR visible agents | Target (mRNA/transcription factor protein) | References |
|---|---|---|
| Gd-[−]hiv-vif | Suicide contrast agent to cell with partial [+]hiv vif coding sequence | This project |

Schiff-base Linkage

To avoid possible confounding factors introduced by the immunogenic properties of Avidin for biotinylated sODN linkage in our original design, we have synthesized SPION-sODN with Schiff-base linkage (SPION-SB-gfap); the stability of Schiff-base linkage in serum can be protected by exosomes for our future application (Alvarez-Erviti et al., 2011).

Administration of Suicide Beacon

The suicide beacon can be administered using intracranial injection (icy route) for homogenous distribution. However, we have demonstrated delivery by intraperitoneal (i.p.) injection when BBB is known to open in neurological disorders; therefore, I.p. can serve as a delivery alternative (Liu et al., 2008a). We also demonstrated an sODN with sequence homologous to non-transcribed strand of GFAP genome (sense sequence of GFAP mRNA); this sODN of Sense-gfap hybridizes only to genomic DNA (Liu et al., 2013). Although gold has been used for cancer eradication, gold-tagged nanoparticles will generate heat in MR and cannot be used in MR. We have generated Gd-[−]-hiv-vif (a cytotoxic T1 contrast agent) for detection and toxicity within the host. Additionally, Adriamaycin, Doxil or Myocet may be linked to the beacon for enhanced eradication of host cells. Thus, in certain embodiments, the suicide beacon is further linked to Adriamaycin, Doxil or Myocet.

We anticipate that HIV or SW will have a high mutation rate as the host cell replicates. We have demonstrated that DNA:RNA hybridization can be reduced when there are 3 mismatches in 17-nts, i.e., ~1/6 mutation rate (Liu et al., 1994). If one expects that RNA polymerase will make $2 \times 10^{-4}$ mutation in each infection cycle (Blank et al., 1986), we anticipate one mutation after $10^4$ reverse transcription and the mutation has to be sequestered in target site of the reservoir. Nevertheless, we can overcome this rare event by changing the target site within the 9000 bases in the genome, and there will be 450 potential target sites available. For HIV-1 see http://www.hiv.lan1.gov/content/sequence/HIV/MAP/landmark.html (adapted FIG. 16—See Exemplary HIV genome, SEQ ID NO: 28.

Detection of a partial HIV reservoir in PC-12 neural progenitor cells (undifferentiated PC12 cells in culture). FIG. 1 shows PC12 cells retained sODN of Cy3-hiv-vif (either [+] or [−] strand of Cy3-hiv-vif-ASgfap) (FIGS. 1A & 1D respectively). Although both groups took up sODN of Cy5.5-SPION-[−] hiv-vif (the imaging beacon) (FIG. 1E left); the cells harbor HIV reservoir ([+]hiv-vif-Asgfap) retained the imaging beacon for longer time than the control (FIGS. 1B and 1E right). We observed 50% killing when imaging beacon was replaced with Gd-[−]-hiv-vif (the suicide beacon). Mechanisms of anchorage and reporting are based on sequence complementation as discussed in FIGS. 2-9 (Liu et al., 2013).

We have reported a novel AS strategy for evaluating neural cell population based on unique gene transcript in living brains (Liu et al., 2013). This strategy uses a multi-modal agent, which contains Cy-5.5 labeled SPION (a biocompatible T2 MR susceptibility contrast agent) and a small single-stranded AS DNA linked with Avidin-biotin conjugates (FIG. 2A). The Avidin-biotin allow less expensive preparation for research applications. A direct linkage for DNA and SPION has been made with a Schiff-base linkage for human cells (Hogemann et al., 2000), and we observed a similar efficiency in both (unpub. obs.).

Figure 5A:
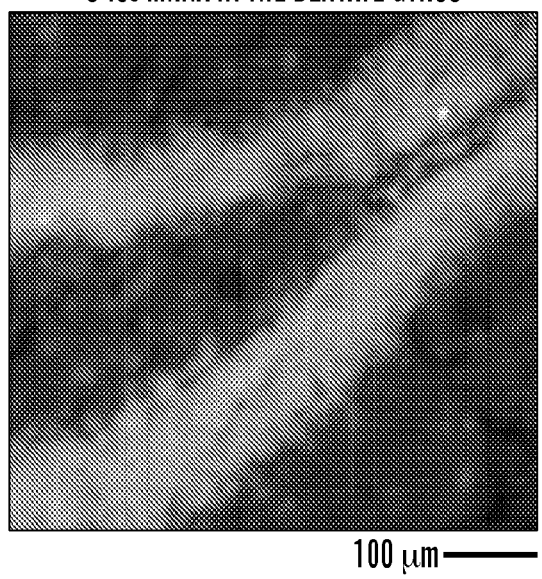
FIG. 5. Show in situ RT-PCR indicating validation of AS-sODN-cfos target binding in vivo by in situ RT-PCR. SPION-cfos was delivered to living mice, and frozen brain slices were prepared for primer-free reverse transcription followed by PCR amplification with cfos primers (5A) or randomized primer (not shown) or without primers (5B).
Figure 5B:
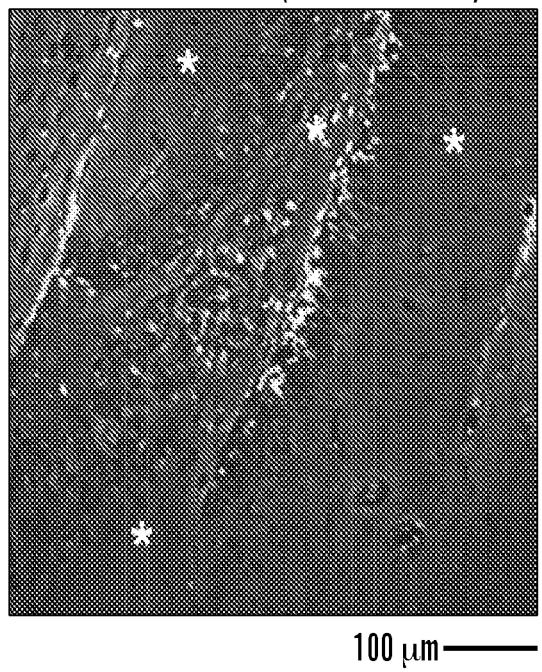
Figure 6A:
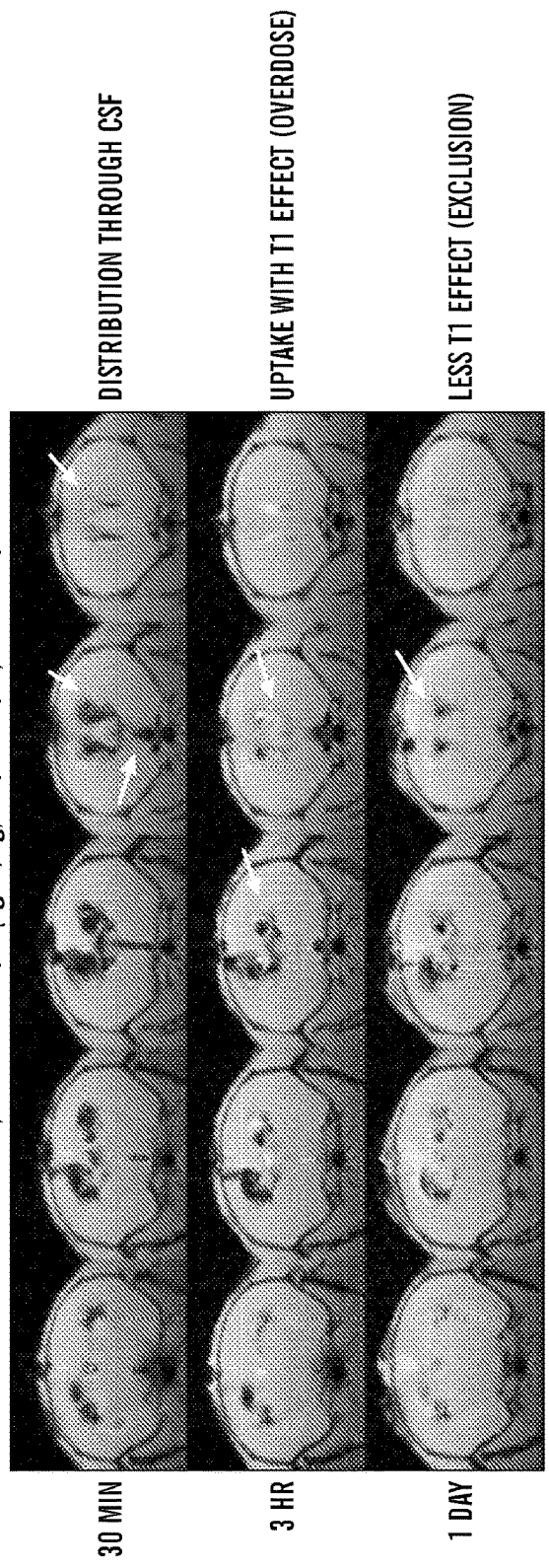
FIGS. 6A and 6B. Shows a 9.4 Tesla MRI showing living brains retain SPION-sODN (6A), but not SPION without targeting sODN (6B) (see (Liu et al., 2007c). Signal reduction is dependent on a linkage between sODN and iron oxides.
Figure 6B:
Figure 7A:
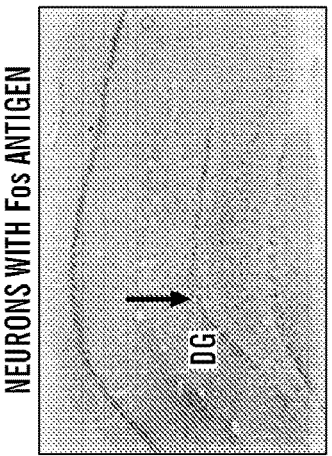
FIGS. 7a to 7E. Show MRI in normal mice, neurons in the dentate gyrus (DG) are Fos-positive (7A) and take up SPION-cfos (7B); they are not GFAP-positive (7C) and do not take up SPION-gfap (D). T2*-weighted MRI (panels 7B, 7D & 7E) acquired using a 14T magnet. See detail in (Liu et al., 2013). The results show specific retention and targeting of SPION-cfos or SPION-gfap in neurons or astroglia, respectively.
Figure 7B:
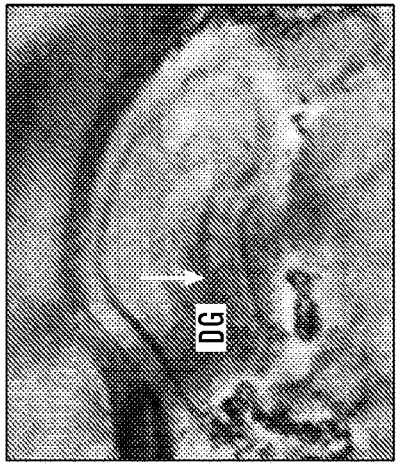
Figure 7C:
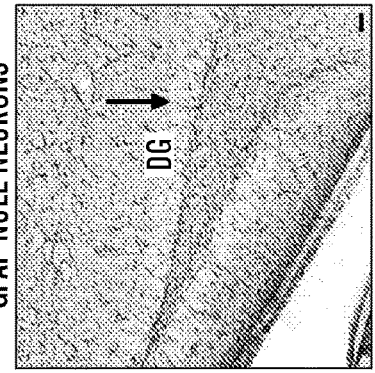
Figure 7D:
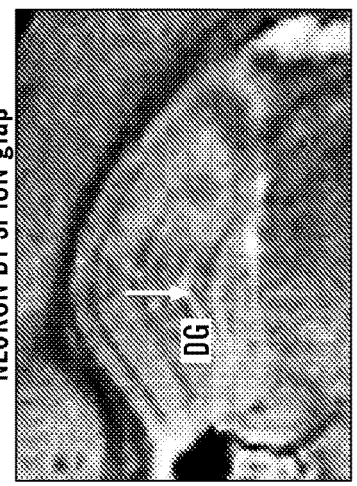
Figure 7E:
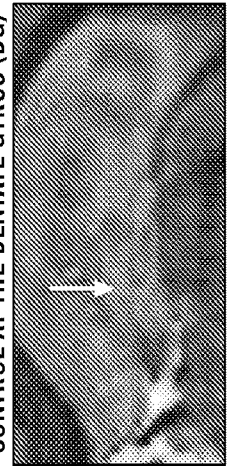

Upon delivery by intracerebroventricular (icy) or intraperitoneal (i.p.) injection, SPION-sODN is taken up by endocytosis (FIGS. 2B & 3), supporting the result reported by others (Beltinger et al., 1995). The single-stranded As DNA seeks its RNA and form hybrids (FIGS. 2C & 4); such hybrids can be demonstrated using primer-free reverse transcription in situ (FIG. 5). For the excess SPION-sODN without hybridized RNA target or SPION-randomized (Ran), the living cell excludes them (FIG. 2D). Such exclusion allows a retention of targeting agent (FIG. 6A) and no retention of SPION by fast exclusion over no longer than the first 30 min post delivery (FIG. 6B).

Figure 8:
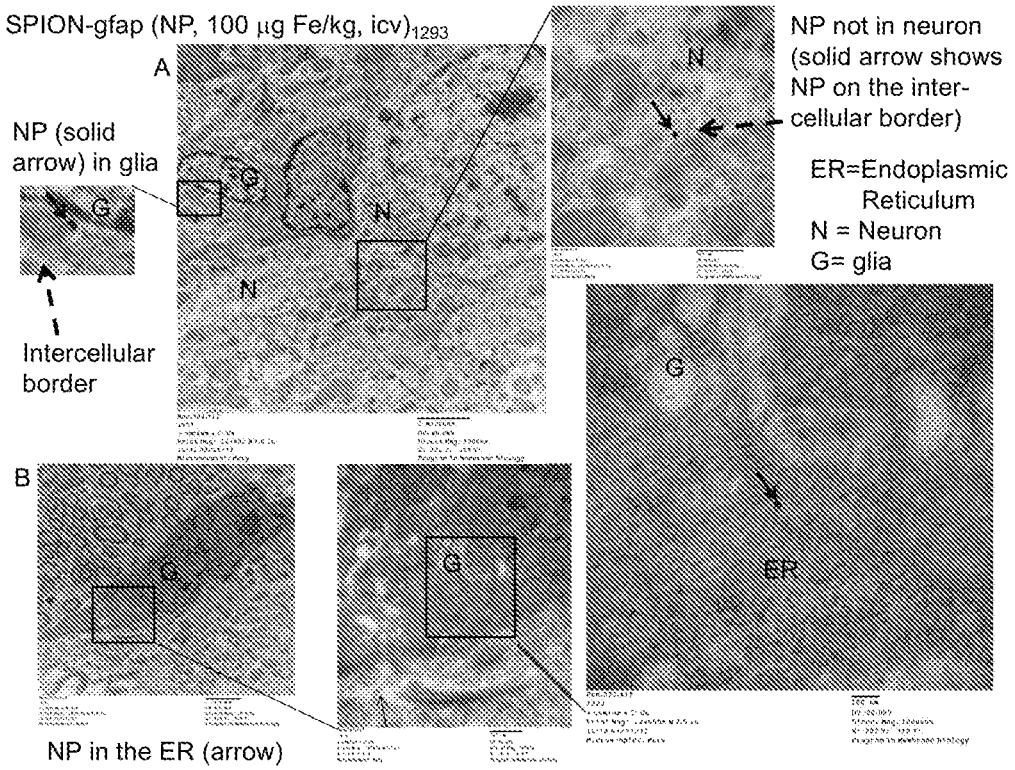
FIG. 8 shows electon micrographs. SPION-gfap is present in the endoplasmic reticulum (ER) of astroglia (G) but not neurons (N). See (Liu et al., 2013). The results show specific retention and targeting of SPION-gfap in astroglia.

This principle of hybrid formation and exclusion allows a precise cell profiling because SPION conjugated with single-stranded AS sODN (e.g., for GFAP mRNA, SPION-gfap) that targets astroglia/microglia, but not neurons, when SPION-gfap are delivered to normal mouse brains, detectable by MRI (FIG. 7) and with validation by TEM (FIG. 8). This in vivo technique quantifiably reports RNA at very low levels from one (Fosb mRNA) to 2500 (GFAP mRNA) copies per $10^{-9}$ gram (ng) with linear regression of >0.9 (p=0.02) compared to TaqMan analysis in normal mouse brains (FIG. 9), and in disease models that increase or decrease glial cell populations in living brains (Liu et al., 2013).

We achieve this precision by a careful procedure of MR acquisition with excellent and uniform uptake as shown in the contrast to noise ratio in vivo (FIG. 10). The contrast to noise ratio is most optimal for MRI detection at 6 hrs after delivery. In our experience, as little as 18% mismatches (E value>0.1) by NCIB/BLAST program between the SPION-sODN and mRNA will have no signal reduction in MR. RNA-targeting MRI can detect activated microglia with a voxel of 0.03 mm$^3$ in a 9.4Tesla MR system, without biopsy, in the whole brain of the same mice over time (Liu et al., 2012). Such precision reveals in the detection of changes in the astroglia cell population (reduction in the striatum and gliogenesis in the subventricular zone) by MRI in living brains (FIG. 11A) and with validation by optical microscopy post mortem (FIG. 11B).

Figure 12A:
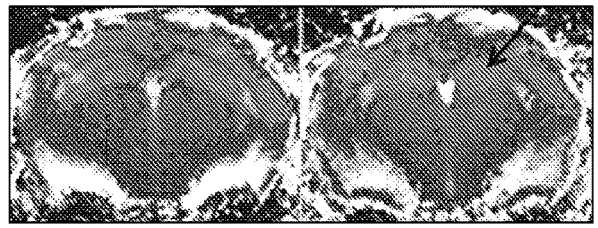
Figure 12B:
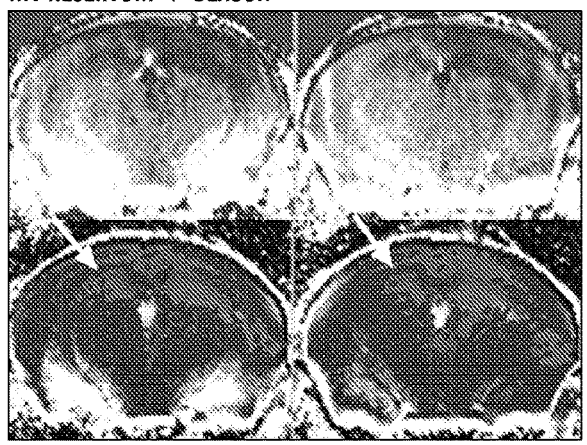
Figure 12C:
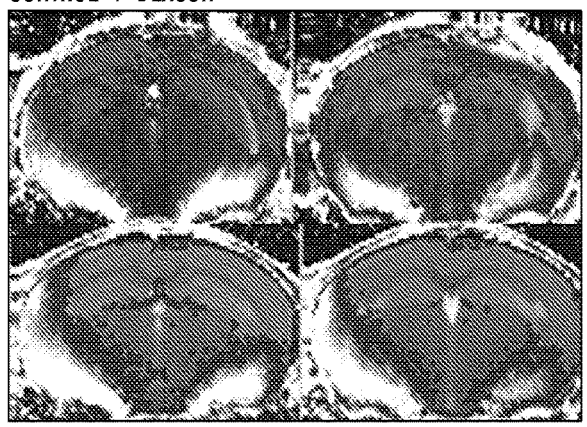

Detection of Cells Harboring the Vif Gene in Living Brains. We translated our cell culture finding (FIG. 1) to the CNS of living C57black6 mice by transfection of the sODN of reservoir or control (n=2 each); the reservoir was detected by the imaging beacon (FIG. 12 B); no elevation in R2* maps in control mice (FIG. 12C). The R2* maps of the control mice was no different from those of before sODN transfection (FIG. 12A).

Sensitivity The threshold concentration for detection of iron oxide nanoparticles without DNA in the brain is 62.2 ng Fe/mm$^2$ with a 1.5T magnet (Zimmer et al., 1995). Our studies show that changes in gene transcript levels can be modulated in vivo by low dose iron oxide using MRI technologies in living mouse brains (Liu et al., 2007c, Liu et al., 2009a), and the results are supported by those using reporter gene systems (Renthal et al., 2008). The threshold concentration for a 4.7T or 9.4T magnet using our RNA-targeting contrast agents was 1 ng Fe per mm$^3$. The SPION-sODNs are made of antisense DNA/RNA and iron oxide nanoparticles (FIG. 2A or 6B) or Gd-DOTA; both of which can be approved by FDA for human applications.

NHP-SIV Model in AIDS Research: The SIV-infected rhesus macaque shares very similar pathology with HIV-infected human patients, including the development of AIDS and CNS disease (Desrosiers, 1990, Murray et al., 1992, Zink et al., 1997, Zink et al., 1998, Burudi and Fox, 2001). Similar to HIV, SIV infects CD4+ macrophages, lymphocytes, and microglia. Neuroinvasion occurs early in infection for both HIV and SIV (Chakrabarti et al., 1991). Peak viremia is typically observed at ~2 weeks after infection (Reimann et al., 1994, Staprans et al., 1999, Fuller et al., 2004, Greco et al., 2004).

After the acute stage of SIV infection, SIV reproduces at very low levels, although it is still active. The disease moves into a chronic stage. This period can last up to several years similar to the stage of clinical latency observed in humans infected with HIV. Toward the end of this period, VL begins to rise again, CD4 cell count begin to drop and animals start to develop AIDS.

Figure 13:
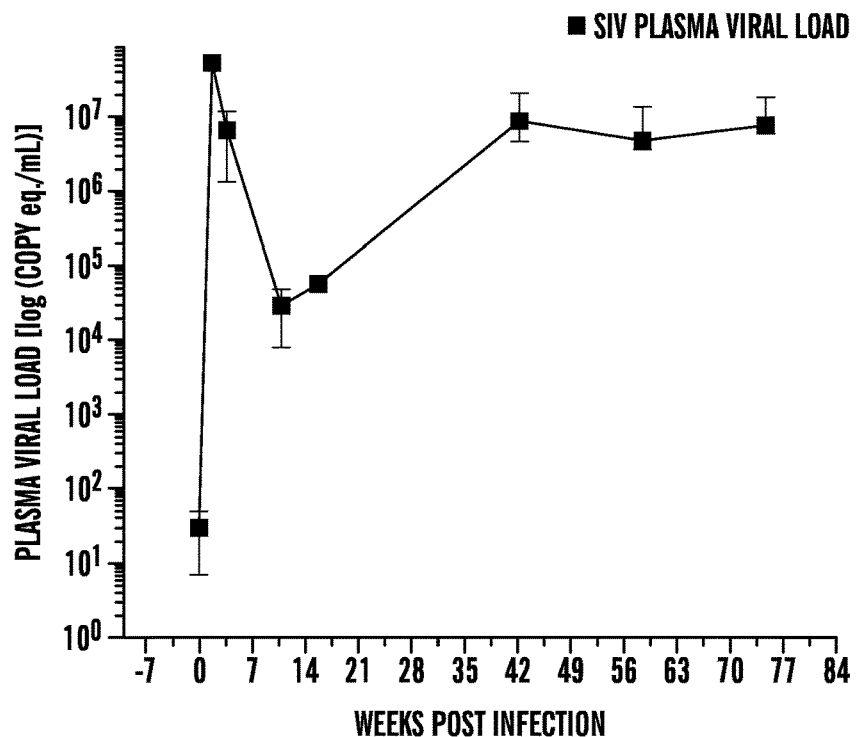
FIG. 13 shows a graph of plasma viral load vs weeks post infection. Longitudinal plasma viral loads in SW-infected macaques. Eight juvenile rhesus macaques were inoculated intravenously with SIVmac251. Virion-associated SIV RNA in plasma was quantified using a real-time RT-qPCR assay.

FIG. 13 shows the average plasma VL levels of eight juvenile rhesus macaques (*Macaca mulatta*) inoculated intravenously with SIVmac251 (50 ng p27/kg) (Kodama et al., 1993). Virion associated SIV RNA in plasma was quantified by using a real-time reverse transcription-PCR assay on an Applied Biosystems Prism 7700 sequence detection system as described previously (Desrosiers et al., 1998). Results are averages of duplicate determinations (Credit: Analyses of viral RNA levels were performed by Drs. Jeffrey Lifson and Michael Piatak at SAIC-Frederick, collaborators of Dr. E Ratai, Co-investigator of this application).

Combination antiretroviral therapy (CART) has been successfully applied to SIV-infected macaques (Fox et al., 2000, Williams et al., 2005). Rhesus macaques inoculated with pathogenic SIVmac239 and treated with CART from weeks 13 to 41 post infection (wpi) revealed viral loads below 200 RNA copies/mL during CART (zur Megede et al., 2008). The CART regimen consisted of 9-R-2-Phosphonomethoxypropyl adenine (PMPA), 5-Fluoro-1-[(2R,5S)-2-(hydroxymethyl)-[1,3]oxathiolan-5-yl]cytosine (FTC), and 2'-3'-didehydro-2'-3'-dideoxythymidine (Stavudine, Zerit®).

Figure 9:
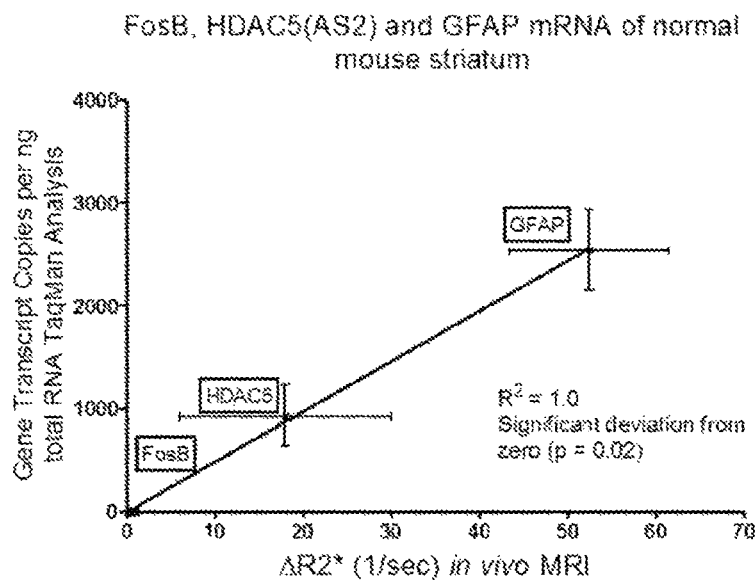
FIG. 9 shows a graph of gene transcript copies per change in R2. The change in ΔR2* in response to three different mRNA is positively proportional to mRNA copy number (Liu et al., 2013). The results show target precision of our contrast agent is similar to that of quantitative PCR.
Figure 14:
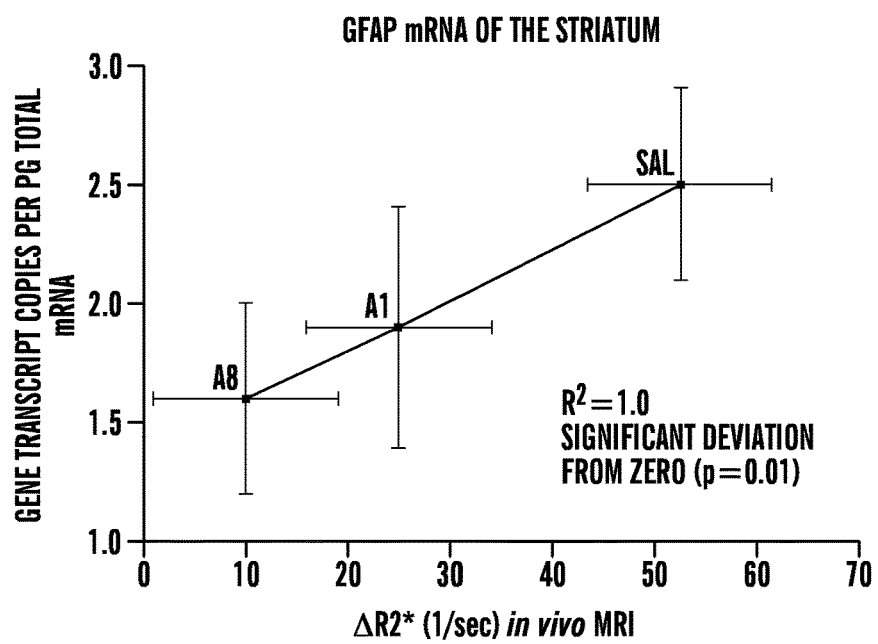
FIG. 14 shows a graph of gene transcripts vs change in R2. A direct correlation of R2* values and mRNA copy number. (Published as supplemental Figure S4 in Liu et al., 2013). Shows three copy numbers of the same mRNA in three different disease conditions. See also FIG. 9. These results provide another proof for precise targeting according to the expression of genes within cells.

We have demonstrated SPION-[−]-hiv-vif (exemplary imaging beacon) detects an HIV reservoir of [+]-hiv-vif and Gd-[−]hiv-vif (exemplary suicide beacon) reduces cells with HIV reservoir. The technology is based on sensitivity and specificity of RT-PCR under normal or pathological conditions (FIGS. 9 and 14). We have delivered SPION-c-fos contrast agent to NHP-macaques at 10 mg/kg (icy) and found no toxicity at all (unpulished Veterinary Report from the Center for Comparative Medicine of MGH).

Gd in a suicide beacon can be delivered to the NHP-SIV model before, during and after CART to confirm that Gd-[−]-siv-vif reduces SIV-VL further and to aid in dosing form humans.

To overcome potential mutations in the target HIV site, multiple additional sODN suicide beacons can be delivered to multiple HIV genome variants or multiple mRNAs, such as gap, pol, vif, vpr, vpu and gp160. The design focus' on neural cells harboring the HIV genome of living animal brains, first in mice then in NHP-Macaque animal model. In theory, an HIV genome of approximately 9000 nts should allow at least 250 different sODN of 36 nucleotides in length for recombinant reservoirs. A combination of HIV genes sequence in the reservoir sODN will increase the number of Gd-beacon per viral DNA per cell, therefore, enhance toxicity to the cell hosting the HIV reservoir. Alternatively doxorubicin can be linked to the beacon ([−]hiv-vif-dox) for future translational use in humans with kidney problems.

Reduction in Neural Cell Population with HIV Reservoir by MRI:

Traditionally, neural cell death is shown by histology ex vivo. We have shown the ability of MRI to demonstrate a reduction in neuronal or astroglial cell populations in living brains based on a direct correlation of ΔR2* values and mRNA copy number, with validation by histology (Liu et al., 2008a, Liu et al., 2013). FIG. 11 shows a reduction in striatal astroglia population is based on a reduction in GFAP mRNA copy number that is reflected by in vivo R2* values (FIG. 14). This method can be used to evaluate the efficacy of suicide beacon.

Figure 15A:
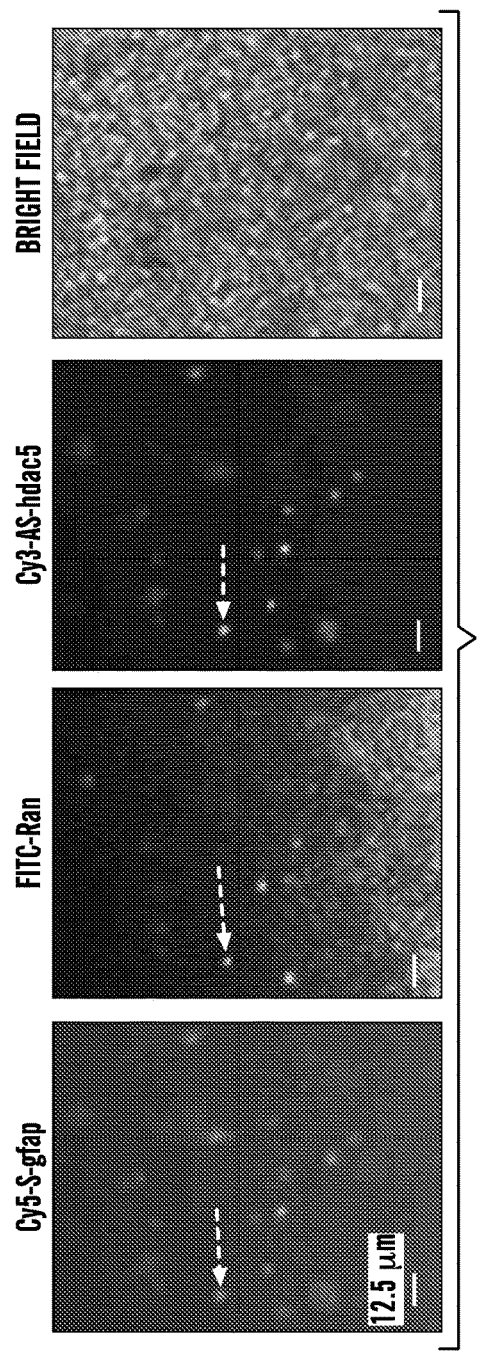
FIG. 15A to 15C show immunofluorescence. Evidence of transient retention of the sense sequence (Cy5-S-gfap) in the nucleus of PC12 cells (published as FIG. 2 in Liu et al., 2013). We transfected cy5-S-gfap, FITC-Ran, Cy3-AS-hdac5 sODN (10 nM) to fresh brain slice (60 micron, from C57black6 mice) in a stage incubator (model UK, Tokei Hit, Japan) for multichannel, real time photography (published as FIG. 2 in Liu et al., 2013). All sODN were retained (15A), except sODN-Ran which was no longer visible within 5 min after washing (15B). The sODN of Cy3-S-gfap was retained in the nucleus at 10 min (15C).
Figure 15B:
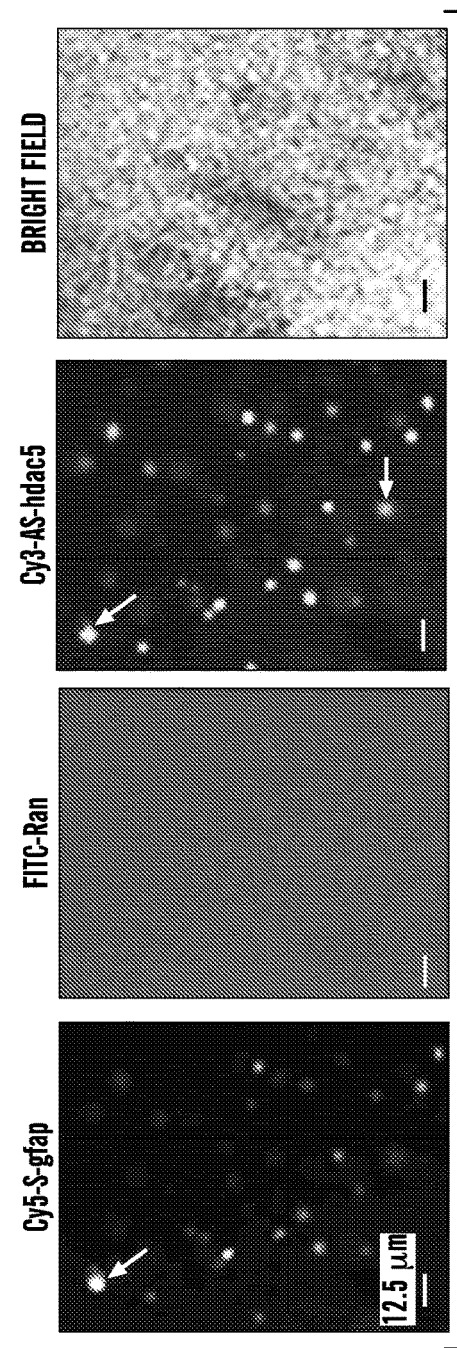
Figure 15C:
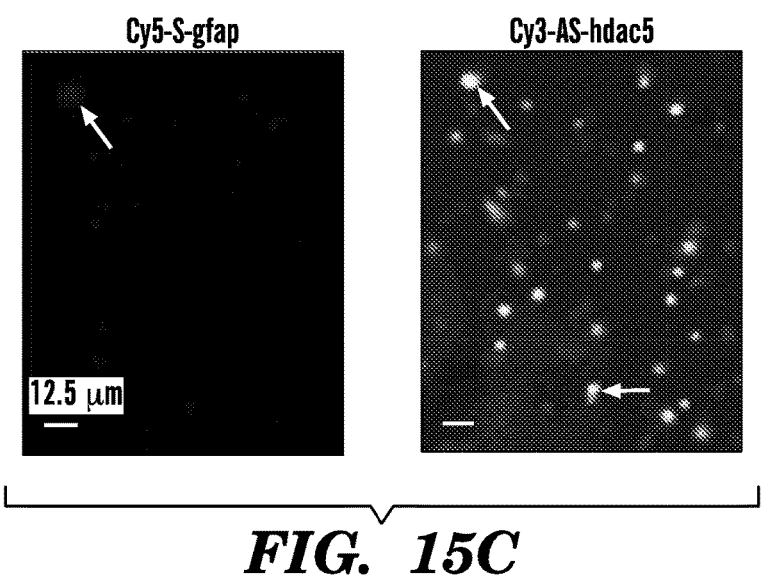

Targeting Genomic HIV in the Latent Reservoir: Because the dose for MRI for sODN in the contrast agent is at least ¹⁄₁₀₀ of recommended dose gene knockdown, we have not observed gene knockdown effect using RNA targeted MRI (Liu et al., 2009b, Liu et al., 2012). We denote cytoplasmic RNA to be [+] sequence; therefore, SPION-[−]siv-vif should have two targets: one in cytosol and the other will be in the nucleus. To target the genomic DNA of SIV when the virus does not produce RNA we will use SPION-[+]siv-vif for imaging, which should have one target in the nucleus. When antisense DNA binds to genomic DNA, there may be a formation of transient triplet DNA. FIG. 15 shows the sODN with sense sequence of gfap mRNA targets genomic DNA (Liu et al., 2013).

Avidin-free contrast agents: Micro DNA can be conjugated to an MR-visible contrast agent by either a disulfide linker (SS) moiety (Chrisey et al., 1996), or a Schiff base (BS) linkage (Josephson et al., 1999). We initially selected Avidin-biotin conjugation because it allows us to apply a wide variety of intracellular targets by changing the biotinylated micro DNA, as a click-on approach. This approach has served as a cost-effective means to establish our novel MRI technique for imaging gene activities in live brains. We now have further generated NeutrAvidin-free MR agents using linker of BS. We found BS linker (SPION-gfap) has similar stability in cell culture and in living mouse brains. We have tested a range of low to high doses (0.04-10 μg per kg, icy) in rhesus macaques, and have observed no lethal effect; however, because the high dose may reduce the rate of clearance and prevent longitudinal MRI, we will determine the dose that yields optimal contrast-to-noise ratio (CNR) within a reasonable time frame and allows tissue to clear the contrast agent for appropriate longitudinal MRI scheduling. To increase SPION-BS-sODN in serum, we will test exosome-mediated transfection (Alvarez-Erviti et al., 2011), first in rodents, and later in NHP.

Method to Quantify the VL in Plasma of NHP after SIV Infection (Yrs 1-2)

One key demonstration of the advantage of our technology is a positive correlation between copy number and R2* values. We expect that imaging contrast agent will detect VL of SIV in vivo. Because copy number equivalent per ml of blood is commonly used for VL in NHP-SIV model, we aim to determine that SPION-siv-vif targeting SIV in the serum by MRI will have the same specificity and sensitivity by RT-qPCR.

Juvenile Rhesus macaques will be inoculated with SIV-mac251 (20 ng SIVp27, i.v.) and then treated with CART consisting of PMPA, FTC and Zerit®] starting at 10 weeks post inoculation (wpi) for 2 months. For VL determination using SIV-targeted MRI, we will draw blood from NHP-macaques infected with SIV (n=3) and the VL will be determined with RT-qPCR and MRI with SIV targeting SPION-sODN at various times as followings:

| MRI Scan | Expected Viral Load |
| --- | --- |
| −2 weeks post infection (wpi) | 0 |
| −1 days post infection | 0 |
| 2 wpi | Peak viral ~$10^7$ copies/mL |
| 10 wpi (initiate CART on 13 wpi) | ~$10^4$ copies/mL |
| 2 months after CART | ~$10^2$ copies/mL |
| 1 month after terminating CART (41 wpi) | ~$10^3$ copies/mL |

Viral Load of SIV by MRI: In NHP-SIV macaques, we will withdraw blood (0.5-1 ml) from NHP immediately before the delivery of SPION-sic-vif as baseline. We will then deliver SPION-siv-vif (1 mg Fe or 3 nmol sODN per kg, iv); we will draw the blood again at hourly intervals for 6 hours after SPION-siv-vif injection (0.5-1 ml each). We will divide each sample into two: one part will be sent for SIV copy number measurement by an independent laboratory and the other half will be mixed with 2 ml of agarose (2%) in 4 aliquots for R2* acquisition by MRI. The average of 4 determinations in MR will be compared for significant elevation above the baseline. The optimal R2* values is the peak elevation during the 6 hours period and the optimal time for future VL measurements; the peak value will be compared for correlation between copy number as VL and R2* values (FIG. 9). The control will be injected with SPION-randomized sODN (which has no target in living cells) and produce no significant elevation in R2* values (therefore no optimal time). MR imaging will take place at the A. A. Martinos Center for Biomedical Imaging. We will generate a standard curve with increasing amount of SPION added to serum (0.1 ml) from the baseline and mixed with agarose for phantoms. The standard curve will be included in each MRI when post SPION-[−]siv-vif is acquired tof MRI.

Animal Care. Animals will be housed at the MGH/Martinos Center for Biomedical Imaging. All animals will be monitored clinically for general health with complete blood counts, fecal ova and parasite examinations, and physical examinations performed before inoculation and every other week thereafter. Body weight, food consumption and stool character will also be recorded daily. Blood and CSF will be collected prior to inoculation and at multiple time points thereafter including at the time of imaging. Animals will be euthanized by licensed veterinary at MGH with an overdose of sodium pentobarbital (100 mg/kg), when moribund with AIDS as a service by the Center for Comparative Medicine.

Animal Preparation. The macaque will be restrained with a squeeze cage apparatus and anesthetized by administration of ketamine (15.0-20.0 mg/kg, i.m.) for transport within the facilities. After arrival at the imaging site, an endotracheal tube will be inserted and an intravenous catheter with a 3-way stopcock will be inserted into a peripheral vein. Propofol (0.25 mg/kg/min) will be administered intravenously to maintain anesthesia. Once placed in the magnet, the animal's heart rate, oxygen saturation, pulse rate, end-tidal $CO_2$, and temperature will be monitored by MR compatible equipment.

MR Imaging. All ex vivo MR experiments will be performed on a 4.7 or 9.4 T MR imager (Liu et al., 2007c). We will have 7 samples (baseline+6 post SPION samples) in three test tubes (triplets) per animal per time point, each animal will need 1.5 hr MRI time each or 6 hours each time point for 6 time points in a group of 3 animals. We will need 36 hours. We request 40 hours MRI time each year for years one and two.

Expected Results: We expect to observe a positive correlation between MRI and RT-qPCR (~$r^2 \geq 0.7$) based on results we have on different RNA imaging (FIGS. 9 & 15) and preliminary study on HIV reservoir detection (FIG. 1). Gd-siv-vif will then be administered to evaluate reduction on SIV-VL.

How to Find an Optimal Window to Apply Gd-[−]-Siv-Vif and Reduce the VL in SIV Infected NHP-Macaques.

Expected Gd-[−]-siv-vif reduces VL in NHP-SIV model. All ex vivo MR experiments will be performed on a 4.7 or 9.4 T MR system. To investigate whether Gd-[−]-siv-vif will reduce the VL in NHP-SIV model, we will first demonstrate efficacy in reducing SIV-VL in the blood (A), then in the CNS (B). The control will be a sODN of randomized sequence (sODN-Ran) without any RNA or DNA target in mammalian cells; this sODN-Ran will be linked to Gd (Gd-Ran).

We will apply the theranostic strategies of Gd-[−]-siv-vif in NHP-SIV (n=6 or any from Aim 1 if they survive). When the VL of SIV reaches the peak level (~2 weeks post infection), the animal will be randomly separated to three groups (n=3) to receive Gd-[−]-siv-vif treatment (0.1 mmol Gd or 100 nmol sODN per kg, weekly, iv) for 8 weeks at three different times (see schedule); the remaining two groups will receive the same dose with the same interval of Gd-Ran as placebo. The Gd-siv-vif administration will be before (Group 1), along with (Group 2) and after CART (Group 3). At the end of CART, we will compare the SIV-VL by MRI (weekly for 3 weeks) of the blood obtained from all animals (baseline and at the optimal time determined in Aim 1) four weeks after termination of Gd-siv-vif delivery (to avoid T1 effect); a significant reduction in the VL of SIV would indicate an effective Gd-[−]-siv-vif beacon treatment. We will repeat the SIV-VL measurement by MRI at termination of CART and one month later (41 and 45 wpi) to demonstrate if VL re-elevates.

Expected Results and Alternative approaches: We expect to observe a transient effect in VL reduction (less than $10^{-3}$ copies/ml expected one month after CART) in NHP-SIV after CART with Gd-siv-vif because we obtained only 50% killing in single target Gd-beacon (28 nmol/ml) during preliminary studies. We may have to increase 8 weeks to 16-week treatment duration. Alternatively, we will increase the number of targets per SIV genome. We have outlined a strategy to increase the concentration of Gd per cell without actually increasing the total amount of Gd (C. Design or D.3.B). In theory, we can make over 250 targeting sODN of 36 nts in length per SIV genome of 9000 nucleotides in length (same length as HIV genome). Another alternative is to link Gd-siv beacon to Adriamaycin, -Doxil or -Myocet.

| Time course | Weekly injection | MRI by SPION-siv-vif |
| --- | --- | --- |
| −2 weeks post infection (wpi) | none | once |
| −1 days post infection | none | once |
| 2 wpi | Gd-siv-vif or Gd-Ran 2-10 wpi | Weekly between 14-16 wpi |

| Time course | Weekly injection | MRI by SPION-siv-vif |
|---|---|---|
| 10 wpi (initiate CART on 13 wpi) | Gd-siv-vif or Gd-Ran 13-21 wpi | Weekly between 24-26 wpi |
| 2 months after CART | Gd-siv-vif or Gd-Ran 21-29 wpi | Weekly between 32-34 wpi |
| terminating CART at 41 wpi | none | once |
| 1 month after terminating CART | none | once |

We aim to reduce SIV-VL in the CNS with Gd-siv-vif. Because the viral reservoir in CNS may occur as soon as infection started, we will compare VL in the cerebrospinal fluid (CSF) from NHP-SIV after CART with and without Gd-siv-vif. We will acquire brain images (T2 weighted MRI) of all SIV infected NHP-macaques (n=9, D.2.A.) one month after CART termination as baseline MRI. The MRI will allow us to determine the suitable site and the depth of insertion for intracerebroventricular (icy) delivery near the bregma so that the SPION-siv-vif will be distributed evenly within ventricular space to most neural cells. We will then deliver SPION-siv-vif (40 μg/kg) by mixing SPION-siv-vif with CSF (0.5 ml, obtained from the insertion site before SPION-siv-vif) from each NHP-SIV and re-inject back to the same monkey. We will acquire R2* maps (Mandeville et al., 2011). The difference between these two maps will be the VL in the CNS after treatment. If there is no significant difference, we will determine the VL in SIV infected NPH-macaques (n=2) without treatment with Gd-siv-vif. The VL of the two groups (with and without Gd-siv-vif) will show the effectiveness of suicide beacon. If there is no difference, we will deliver Gd-siv-vif (or combination of Gd-siv suicide beacons) via icy route (Gd=0.1 mmole per kg) weekly for 8 weeks with VL monitor by MRI. Intracranial delivery can be approved for therapeutic purposes, such as the one we are proposing. At the end of 8-week treatment, we will determine the VL in the CNS.

In the event that SPION-siv-vif detects VL of SIV before SL reaches the peak (by RT-PCR), we will administer Gd-[−]siv-vif (0.1 mmol Gd per kg, weekly, iv) before the VL of SIV reaches the peak level (~2 weeks post infection). This early treatment may eliminate SW infected cells and viral enzyme for ELISA assays.

Because most viral reservoir is presented in astroglia, we will acquire MRI using SPION-gfap. Detecting astroglial population reduction is an established in vivo procedure for rodent astrocytes (Liu et al., 2013). We expect to observe significant reduction in astroglial populations in NHP-Macaques that received Gd-siv compared to those without. All in vivo MR experiments on NHP will be performed on a 3 or 7 T MR imager.

We will demonstrate the retention of C5.5-SPION-[−]hiv-vif in cells harboring reservoir sODN, but not in cells harboring control sODN.

In preparation for eradicating HIV reservoir, we will synthesize 20 bp of anchoring DNA, using primate sequences indexed in GenBank. We will focus on two targeting GFAP mRNA of astroglia (sODN-gfap) and/or IBA1 mRNA of microglia (sODN-iba1); we will focus on the sODN that anchors [+]-hiv-vif-ASgfap on primate gfap mRNA. The AS-gfap to primate gfap mRNA will be validated as a primer for PCR of gfap cDNA of one single fragment from primate cDNA library (Liu et al., 2011). We predict no amplification will be observed with a control probe of randomized sequence (sODN-Ran). We will Cy3-tagged single-stranded DNA with partial HIV-1 vif gene with ASgfap of NHP or humans for HIV reservoir (Cy3-[+] hiv-vif-ASpgfap or Cy3-[+]hiv-vif-AShgfap, respectively) or control (Cy3-[−]hiv-vif-ASpgfap or Cy3-[−]hiv-vif-AShgfap, respectively). We will use the same Gd-[−]-hiv-vif as a suicide beacon. Alternatives will be Cy5.5-beacon-Adriamaycin, -Doxil or -Myocet.

To Determine Dose of Suicide Beacon

HIV reservoir or control sODN can be transfected into human cells (HELA or MCF-10). For example, one can test three different doses of suicide beacon to find the lowest but effective dose. We expect to demonstrate the specificities of cell killing by elimination of cells with an HIV reservoir.

Rodent Models with a Partial HIV Reservoir (Yrs 1-3):

Rationale: One can also make a recombinant HIV reservoir in rodents to determine optimal uptake and effective dose. We will determine the optimal time of uptake after delivery of this recombinant DNA containing partial hiv vif gene.

One can make rodent models (C57black6 mice or Sprague Dawley rats) with a partial HIV reservoir by transfecting sODN of reservoir or control (120 pmol/kg, icy) to the brains of C57black6 mice. For example, for optimal uptake, we will label these sODN with Cy5.5-SPION and detect R2* values by MR. We will determine the optimal contrast to noise ratio and peak uptake by R2* values; the optimal time is the optimal time to deliver the beacon to living brains of rodents. We will acquire MRI at 3, 5, 7, 16 (overnight), 24, 48 and 72 hrs after delivery (n=4 each time point). We expect both sODN should have similar uptake. The time course of uptake for sODN of reservoir and control should provide information of the optimal retention time of the reservoir in NHP brains to delivery of theranostic modality. The second control will be Cy5.5-SPION-labed randomized sODN and we expect there will be no significant uptake and no reservoir. We will demonstrate the evidence of uptake of the reservoir by ex vivo histology at the peak uptake using optical and electron microscopies using established and published methods. We will determine the optimal time to deliver Gd-beacon by T1 weighted MRI to cells with HIV reservoir in living brains previously transfected with unlabeled sODN of reservoir. We will also determine whether or not the suicide beacon is retained in the brain for longer period time than Gd-DOTA without [−]hiv-vif. The protocol for T1 weighted MRI for mouse brain has been published in peer-reviewed manuscripts (Liu et al., 2013).

For translation to clinic, we will determine workable theranostic strategies in non-human primate animals harboring [+]hiv vif genome. We will determine the efficacy of this Gd-beacon to eradicate astroglia harboring an HIV reservoir. The protocol has been presented in C.2.E (Liu et al., 2013). We will also compare the stability of the recombinant HIV reservoir in serum or CSF from NHP. We will use three assays to test stability. First, we will inject Avidin-containing or Avidin-free SPION probes (SPION-[+]hiv-vif or [−]hiv-vif-AS gfap, -ASibal, 4 mg/kg, i.p) and obtain serum from 5 ml of blood at 0, 1, 2, 3, 4, 5, 6 and 24 hour intervals to measure iron content by ICP-MS.

Second, the sODN of reservoir or of control will be incubated with serum of NHP for 0, 1, 2, 3, 4, 5, 6 and 24 hours. The Cy3-labeled sODN will be resolved in agarose (1%) by gel electrophoresis; the breakdown of Cy3-sODN will produce a smear after agarose gel electrophoresis.

MRI For scanning at 9.4 Tesla, we will use 4 reservoir-sODN or 4 control-sODN each and 8 time points at 0.5 hr each=32 hours for CNR and (4)×4 doses×0.5 hr each=8 hrs for optimal dose determinations. All MRI will be repeated at the optimal dose and with optimal CNR for power analysis. We estimate the minimum number is n=4 measurements or 40×4=160 hrs×2 (mRNA targeting and genomic DNA targeting)=320 hrs. When parameter optimization is complete, we will repeat the measurements.

The theranostic strategies of Gd-beacon can be applied in rhesus monkey with [+]hiv-vif-gfap reservoir (Yr 5). We will deliver the lowest but effective dose of Gd-[−]hiv-vif-FITC. For cell death of astroglia, we will acquire weekly MRI using SPION-gfap two weeks after the suicide beacon delivery; this is an established in vivo procedure for rodent astrocytes (Liu et al., 2013). We expect to observe significant reduction in astroglial populations in NHP-Macaque received sODN of [+]hiv-vif-ASgfap compare to those receiving [−]hiv-vif-gfap. Alternatives will be Cy5.5-SPION-[−]hiv-vif-adriamaycin, -Doxil or -Myocet.

Alternative Reservoirs: HIV latency can be associated with no measurable viral RNA (Barber et al., 2006), it is uncertain whether RNA is not expressed, or whether production continues with a very low and undetectable level by conventional means. The situation will call for a design to target genomic DNA. FIG. 15 shows the sense sequence of a mRNA in the sODN will have only one target in the transcribed strand of the genome (Liu et al., 2013). Therefore, we will modify our design when there is a need for genomic HIV gene detection; we will use the sODN of sense gfap mRNA (or sODN-G-gfap) for anchorage in the nucleus. In the event we find concrete evidence of nuclear retention (D.3.C), we will focus our efforts on genomic DNA tagging. We will synthesize Cy3-hiv-vif-G-iba1, -G-actin, and -G-fosB hiv reservoirs to tag the corresponding mRNA. We expect to observe similar in R2* elevation in these hiv reservoirs with our preliminary studies, especially we have demonstrated RNA tagging will reflect RNA copy numbers.

Possible alternative methods may include tagging RNA probe with para-CEST (Chemical Exchange Saturation Transfer) because para-CEST agents can be as toxic, if not more than, Gd.

Methods and Data Acquisition: We have published detailed methods and data acquisition of RNA targeting MRI. Here we cited some specific considerations that we have taken to avoid non-specific reporting.

Noise Reduction: We have noted a potential methodological confounding factor in the estimation of relaxation rate (R2*, i.e., the frequency of T2 signal reduction expressed as $second^{-1}$, $R_2{}^*=1/T_2{}^*\times1000$) across different time points when an animal is removed from the scanner, then returned for restudy at a later time (hours or days later): how does one account for variations in magnetic field ($B_0$) in all MR systems across different brain regions? We always perform auto-shimming before each scan to reduce signal inhomogeneity resulting from $B_0$. In addition, we will use the following design for each MR acquisition, to determine if the MR scanner itself contributes significantly to variation in MRI data acquired at different time points. The followings are what we did to acquire MRI in mice, but will adjust or revise protocol for two monkeys in this project.

On each day that we acquire MRI data we will include a control group along with the experimental (treatment) group. SPION-sODN will be delivered to at least four, but no more than eight mice, with two mice reserved as controls (baseline without SPION, SPION-NA, SPION-ran or SPION-gfap). We will acquire at least 5 brain slices (0.5 mm each) from each mouse. Comparing the data from all mice in the control group to assess potential variation, our first criteria are that the average and standard deviation (SD) for each region of interest (ROI) in the 5 brain slices are not statistically significantly different (t test, p>0.05). Second, the mean and standard error of the mean (SEM) of the two controls will not be statistically different from those of previous control groups that received similar treatment on different days. By analyzing the accumulated data from control mice scanned on different days, as well as from different litters, we can examine within- and between-litter differences as well spikes of inhomogeneity related to $B_0$. Third, to determine the overall number of mice required for each experiment (to achieve p=80%; α=0.05%), we will perform power analysis using the means and SEM from both the experimental group and the control group scanned on the same day. By using power analysis to calculate sample size we are able to minimize type II error. Once we complete MRI scans on the minimum number of mice, we will perform statistical analysis (Student t test). We will use a similar design for scanning at 7 Tesla to reduce the noise, using two monkeys.

Contrast-to-noise Ratio (CNR). When RNA-targeting SPION is delivered to a living system, the beacon is taken up by most cells, but a specific retention is determined by the presence of targeted RNA (FIG. 2B), those SPION-sODN without a target is excluded (FIG. 2D). An optimal exclusion ensures an optimal R2* value acquisition and CNR (Liu et al., 2012). CNR is defined (Liu et al., 2013). Although susceptibility artifacts resulting from field inhomogeneity when scanning at 9.4T does exist, in C57black mice the CNR is at least 10 at peak retention when SPION-gfap is used (Liu, et al., 2013). Using 9.4T MRI we have detected a cohort of neural progenitor cells measuring less than 0.1 $mm^3$ after acute neurological disorder in mice (Liu et al., 2008b). We expect the negative aspects of high-field MRI in small animals may not be as severe in large animals such as rhesus macaque or other non-human primates (NHP).

BBB bypass and theranostic application: We have chosen to use intracranial puncture at the lateral ventricular space to bypass the BBB for Gd-[−]-hiv-vif delivery because this method has a uniform point of entry that is superior compared to nonspecific BBB bypass induced by osmotic shock or focus ultrasound. Intracranial delivery in humans can be approved for therapeutic purposes.

Footnotes:

[1] Notes on nomenclature of MR probes: To be consistent with capital letters for proteins, we use lower case for mRNA targeting probes (SPION-actin, SPION-fosB or SPION-gfap), and probes with sense sequence for genomic DNA (SPION-g-actin, SPION-G-fosB or SPION-G-gfap). We use abbreviations for probes with no micro DNA (SPION-NA) or DNA with a randomized sequence (SPION-Ran). For Avidin-free agents, we insert SPION-SB-sODN to represent Schift-base linkage.

References for Example 1

Alvarez-Erviti L, Seow Y, Yin H, Betts C, Lakhal S, Wood M J (2011) Delivery of siRNA to the mouse brain by systemic injection of targeted exosomes. Nat Biotechnol 29:341-345.

Barber S A, Gama L, Dudaronek J M, Voelker T, Tarwater P M, Clements J E (2006) Mechanism for the establishment of transcriptional HIV latency in the brain in a simian immunodeficiency virus-macaque model. J Infect Dis 193: 963-970.

Beltinger C, Saragovi H U, Smith R M, LeSauteur L, Shah N, DeDionisio L, Christensen L, Raible A, Jarett L, Gewirtz A M (1995) Binding, uptake, and intracellular trafficking of phosphorothioate-modified oligodeoxynucleotides. J Clin Invest 95:1814-1823.

Blank A, Gallant J A, Burgess R R, Loeb L A (1986) An RNA polymerase mutant with reduced accuracy of chain elongation. Biochemistry 25:5920-5928.

Burudi E M E, Fox H S (2001) Simian Immunodeficiency Virus Model of HIV-Induced Central Nervous System Dysfunction. Adv Virus Reaserch 56:435-468.

Chakrabarti L, Hurtrel M, Maire M A, Vazeux R, Dormont D, Montagnier L, Hurtrel B (1991) Early viral replication in the brain of SIV-infected rhesus monkeys. Am J Pathol 139:1273-1280.

Chrisey L A, Lee G U, O'Ferrall C E (1996) Covalent attachment of synthetic DNA to self-assembled monolayer films. Nucleic Acids Res 24:3031-3039.

Clements J E, Mankowski J L, Gama L, Zink M C (2008) The accelerated simian immunodeficiency virus macaque model of human immunodeficiency virus-associated neurological disease: from mechanism to treatment. J Neurovirol 14:309-317.

Dash P K, Gorantla S, Gendelman H E, Knibbe J, Casale G P, Makarov E, Epstein A A, Gelbard H A, Boska M D, Poluektova L Y (2011) Loss of neuronal integrity during progressive HIV-1 infection of humanized mice. The Journal of neuroscience: the official journal of the Society for Neuroscience 31:3148-3157.

Desrosiers R C (1990) The simian immunodeficiency viruses Annu Rev Immunol 8:557-578.

Desrosiers R C, Lifson J D, Gibbs J S, Czajak S C, Howe A Y, Arthur L O, Johnson R P (1998) Identification of highly attenuated mutants of simian immunodeficiency virus. J Virol 72:1431-1437.

Dumont M F, Baligand C, Li Y, Knowles E S, Meisel M W, Walter G A, Talham D R (2012) DNA Surface Modified Gadolinium Phosphate Nanoparticles as MRI Contrast Agents. Bioconjugate chemistry.

Fischer-Smith T, Bell C, Croul S, Lewis M, Rappaport J (2008) Monocyte/macrophage trafficking in acquired immunodeficiency syndrome encephalitis: lessons from human and nonhuman primate studies. J Neurovirol 14:318-326.

Fox H S, Weed M R, Huitron-Resendiz S, Baig J, Horn T F W, Dailey P J, Bischofberger N, Henriksen S J (2000) Antiretroviral Treatment Normalizes Neurophysiological but not Movement Abnormalities in Simian Immunodeficiency Virus-Infected Monkeys. J Clin Invest 106:37-45.

Fuller R A, Westmoreland S V, Ratai E, Greco J B, Kim J P, Lentz M R, He J, Sehgal P K, Masliah E, Halpern E, Lackner A A, Gonzalez R G (2004) A prospective longitudinal in vivo 1H MR spectroscopy study of the SIV/macaque model of neuroAIDS. BMC Neurosci 5:10.

Gorantla S, Makarov E, Finke-Dwyer J, Castanedo A, Holguin A, Gebhart C L, Gendelman H E, Poluektova L (2010) Links between progressive HIV-1 infection of humanized mice and viral neuropathogenesis. Am J Pathol 177:2938-2949.

Greco J B, Westmoreland S V, Ratai E M, Lentz M R, Sakaie K, He J, Sehgal P K, Masliah E, Lackner A A, Gonzalez R G (2004) In vivo 1H MRS of brain injury and repair during acute SIV infection in the macaque model of neuroAIDS. Magn Reson Med 51:1108-1114.

Hogemann D, Josephson L, Weissleder R, Basilion J P (2000) Improvement of MRI probes to allow efficient detection of gene expression. Bioconjug Chem 11:941-946.

Josephson L, Tung C H, Moore A, Weissleder R (1999) High-efficiency intracellular magnetic labeling with novel superparamagnetic-Tat peptide conjugates. Bioconjug Chem 10:186-191.

Kodama T, Mori K, Kawahara T, Ringler D J, Desrosiers R C (1993) Analysis of simian immunodeficiency virus sequence variation in tissues of rhesus macaques with simian AIDS. J Virol 67:6522-6534.

Kovochich M, Marsden M D, Zack J A (2011) Activation of latent HIV using drug-loaded nanoparticles. PLoS One 6:e18270.

Lewis M G, Norelli S, Collins M, Barreca M L, Iraci N, Chirullo B, Yalley-Ogunro J, Greenhouse J, Titti F, Garaci E, Savarino A (2010) Response of a simian immunodeficiency virus (SIVmac251) to raltegravir: a basis for a new treatment for simian AIDS and an animal model for studying lentiviral persistence during antiretroviral therapy. Retrovirology 7:21.

Lin X, Irwin D, Kanazawa S, Huang L, Romeo J, Yen T S, Peterlin B M (2003) Transcriptional profiles of latent human immunodeficiency virus in infected individuals: effects of Tat on the host and reservoir. Journal of virology 77:8227-8236.

Liu C H, Huang S, Cui J, Kim Y R, Farrar C T, Moskowitz M A, Rosen B R, Liu P K (2007a) MR contrast probes that trace gene transcripts for cerebral ischemia in live animals. Faseb J 21:3004-3015.

Liu C H, Huang S, Kim Y R, Rosen B R, Liu P K (2007b) Forebrain ischemia-reperfusion simulating cardiac arrest in mice induces edema and DNA fragmentation in the brain. Mol Imaging 6:156-170.

Liu C H, Kim Y R, Ren J Q, Eichler F, Rosen B R, Liu P K (2007c) Imaging cerebral gene transcripts in live animals. In: J Neurosci, vol. 27, pp 713-722.

Liu C H, Ren J Q, Yang J, Liu C M, Mandeville J B, Rosen B R, Bhide P G, Yanagawa Y, Liu P K (2009a) DNA-based MRI probes for Specific Detection of Chronic Exposure to Amphetamine in Living Brains. J Neurosci 29:10663-10670.

Liu C H, Ren J Q, You Z, Yang J, Liu C M, Uppal R, Liu P K (2011) Noninvasive detection of neural progenitor cells in living brains by MRI. The FASEB journal: official publication of the Federation of American Societies for Experimental Biology.

Liu C H, Ren J Q, You Z, Yang J, Liu C M, Uppal R, Liu P K (2012) Noninvasive detection of neural progenitor cells in living brains by MRI. FASEB journal: official publication of the Federation of American Societies for Experimental Biology 26:1652-1662.

Liu C H, Yang J, Ren J Q, Liu C M, You Z, Liu P K (2013) MRI reveals differential effects of amphetamine exposure on neuroglia in vivo. FASEB journal: official publication of the Federation of American Societies for Experimental Biology 27:712-724.

Liu C H, You Z, Liu C M, Kim Y R, Whalen M J, Rosen B R, Liu P K (2009b) Diffusion-weighted magnetic resonance imaging reversal by gene knockdown of matrix metalloproteinase-9 activities in live animal brains. J Neurosci 29:3508-3517.

Liu C H, You Z, Ren J, Kim Y R, Eikermann-Haerter K, Liu P K (2008a) Noninvasive delivery of gene targeting probes to live brains for transcription MRI. Faseb J 22:1193-1203.

Liu C H, You Z, Ren J, Kim Y R, Eikermann-Haerter K, Liu P K (2008b) Noninvasive delivery of gene targeting probes to live brains for transcription MRI. The FASEB journal 22:1193-1203.

Liu P K, Salminen A, He Y Y, Jiang M H, Xue J J, Liu J S, Hsu C Y (1994) Suppression of ischemia-induced fos expression and AP-1 activity by an antisense oligodeoxynucleotide to c-fos mRNA. Ann Neurol 36:566-576.

Mandeville J B, Choi J K, Jarraya B, Rosen B R, Jenkins B G, Vanduffel W (2011) fMRI of cocaine self-administration in macaques reveals functional inhibition of basal ganglia. Neuropsychopharmacology 36:1187-1198.

Murray E A, Rausch D M, Lendvay J, Sharer L R, Eiden L E (1992) Cognitive and motor impairments associated with SIV infection in rhesus monkeys. Science 255:1246-1249.

Namanja H A, Emmert D, Davis D A, Campos C, Miller D S, Hrycyna C A, Chmielewski J (2012) Toward eradicating HIV reservoirs in the brain; inhibiting P-glycoprotein at the blood-brain barrier with prodrug abacavir dimers. J Am Chem Soc 134:2976-2980.

Reimann K A, Tenner-Racz K, Racz P, Montefiori D C, Yasutomi Y, Lin W, Ransil B J, Letvin N L (1994) Immunopathogenic events in acute infection of rhesus monkeys with simian immunodeficiency virus of macaques. J Virol 68:2362-2370.

Renthal W, Carle T L, Maze I, Covington H E, 3rd, Truong H T, Alibhai I, Kumar A, Montgomery R L, Olson E N, Nestler E J (2008) Delta FosB mediates epigenetic desensitization of the c-fos gene after chronic amphetamine exposure. J Neurosci 28:7344-7349.

Song Y, Xu X, MacRenaris K W, Zhang X Q, Mirkin C A, Meade T J (2009) Multimodal gadolinium-enriched DNA-gold nanoparticle conjugates for cellular imaging. Angew Chem Int Ed Engl 48:9143-9147.

Staprans S I, Dailey P J, Rosenthal A, Horton C, Grant R M, Lerche N, Feinberg M B (1999) Simian immunodeficiency virus disease course is predicted by the extent of virus replication during primary infection. J Virol 73:4829-4839.

Williams K, Westmoreland S, Greco J, Ratai E, Lentz M, Kim W K, Fuller R A, Kim J P, Autissier P, Sehgal P K, Schinazi R F, Bischofberger N, Piatak M, Lifson J D, Masliah E, Gonzalez R G (2005) Magnetic resonance spectroscopy reveals that activated monocytes contribute to neuronal injury in SIV neuroAIDS. J Clin Invest 115:2534-2545.

Zimmer C, Weissleder R, O'Connor D, LaPointe L, Brady T J, Enochs W S (1995) Cerebral iron oxide distribution: in vivo mapping with M R imaging. Radiology 196:521-527.

Zink M C, Amedee A M, Mankowski J L, Craig L, Didier P, Carter D L, Munoz A, Murphey-Corb M, Clements J E (1997) Pathogenesis of SIV encephalitis. Selection and replication of neurovirulent SIV. Am J Pathol 151:793-803.

Zink M C, Spelman J P, Robinson R B, Clements J E (1998) SIV infection of macaques—modeling the progression to AIDS dementia. J Neurovirol 4:249-259.

zur Megede J, Sanders-Beer B, Silvera P, Golightly D, Bowlsbey A, Hebblewaite D, Sites D, Nieves-Duran L, Srivastava R, Otten G R, Rabussay D, Zhang L, Ulmer J B, Barnett S W, Donnelly J J (2008) A therapeutic SIV DNA vaccine elicits T-cell immune responses, but no sustained control of viremia in SIVmac239-infected rhesus macaques. AIDS Res Hum Retroviruses 24:1103-1116.

EXAMPLE 2

We have synthesized a phosphorothioate-modified DNA (sODN) that has recombinant reservoirs (partial viral infectivity factor (vif) RNA, [+]hiv-vif, 36 nucleotides [nts]) and an antisense (AS) sODN (20 nts) to Oct4 mRNA in the host cells. We also generated a sODN with negative sequence of vif RNA ([−]-hiv-vif, 20 nts) to target the ODN of reservoir; the sODN [−]-hiv-vif is linked to a cyanine (Cy)-5.5 labeled superparamagnetic iron oxide nanoparticle (SPION, a biocompatible T2 MR susceptibility agent) or gadolinium (Gd, a T1 agent) for proof of delivery to cells with [+]-hiv-vif RNA by MRI for MRI.

Results: We showed PC12 cells retained this recombinant HIV reservoir, which was detected by SPION-[−]-hiv-vif. When linked to gadolinium (Gd, a T1 agent), Gd-[−]hiv-vif (Gd=28 nmole per ml) inhibited 50% of PC12 cells harboring HIV reservoir (p=0.03, n=2). No reduction occurred in cells that had received the control reservoir.

EXAMPLE 3

Targeted—Guided Delivery

Figure 17A:
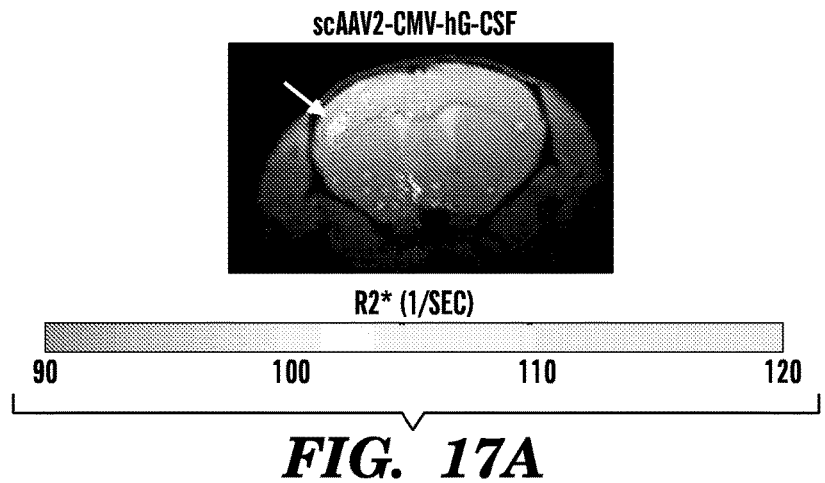
FIG. 17A-17D.
Figure 17B:
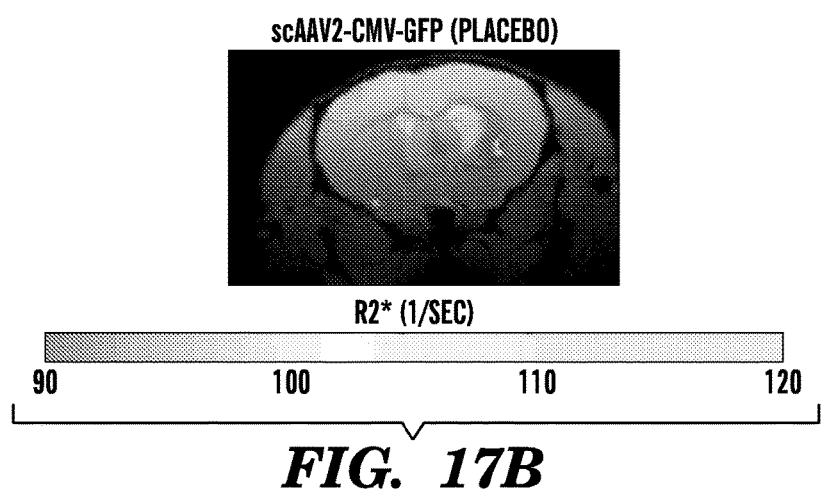
Figure 17C:
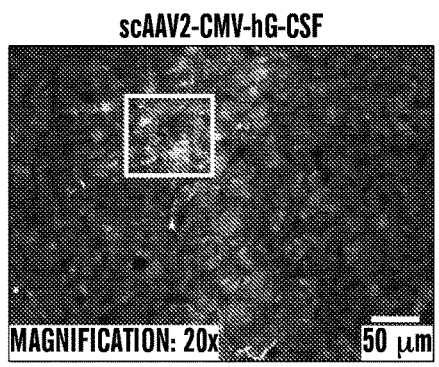
Figure 17D:
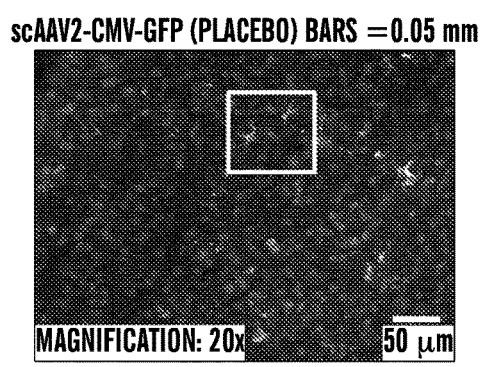

We selected an Adeno-associate viral (AAV-2) vector with a human cDNA for granulocyte-stimulating factor (hGCSF) cDNA. The control is the same virus with a green fluorescent protein (GFP) cDNA. These viruses (scAAV2-CMV-hG-CSF or scAAV2-CMV-GFP) have been shown to express hGCSF and GFP protein in rat PC-12 cells, respectively. We designed a targeting sequence to hGCSF ("−"hGCSF is 22 nucleotides AACTCGGGGGAGATCCCTTCCA-biotin SEQ ID NO: 29); we made targeting contrast agent for MRI by linkage to SPION. We treated mice with scAAV2-CMV-hG-CSF or placebo group (scAAV2-CMV-GFP) (3×10⁹ pfu; 1.5 μl to the eye sac of the left eye) immediately after cerebral ischemia. We detected the presence of viral gene (hG-CSF mRNA) using "−"hG-CSF targeting CA (SPION-hGCSF, 4 mg Fe per kg, i.p.) two weeks later. We found the expression of hG-CSF mRNA was clearly shown as unique ROI in $\Delta R2^*$ map using SPION-hG-CSF (arrow pointed to a region of interest [ROI] of high expression above baseline R2* value (90 per sec or frequency of signal per sec at 3 standard error of the mean above the average R2* values of mice without SPION-hGCSF, FIG. 17A), although there was common noise, we observed no such ROI in placebo group (FIG. 17B). We then obtained necropsy samples from both group and the histology shows hGCSF protein in the ROI identified in MRI in vivo (box, FIG. 17C); we validated hG-CSF antigen expression to be in the non-astrogial population of the brain. The expression of hG-CSF in the placebo group was negligible except astrocytes (box, FIG. 17D).

REFERENCES

The references cited throughout this Specification and Examples are incorporated herein in their entirety by reference.

The invention claimed is:

1. A magnetic resonance imaging (MRI) agent for detecting or killing an HIV-infected cell, the agent comprising a T1 or a T2 contrast agent linked to a single stranded phosphorothioate-modified oligodeoxynucleotide (sODN) that includes a nucleotide sequence that binds specifically to an HIV nucleic acid sequence, wherein the nucleotide sequence is selected from the group consisting of SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 9, SEQ ID NO: 10, SEQ ID NO: 11, SEQ ID NO: 12, SEQ ID NO: 13, SEQ ID NO: 14, and SEQ ID NO: 15.

2. The MRI agent of claim 1, wherein the nucleotide sequence is selected from the group consisting of SEQ ID NO: 51, SEQ ID NO: 52, SEQ ID NO: 53, SEQ ID NO: 54, SEQ ID NO: 55, SEQ ID NO: 56, and SEQ ID NO: 57.

3. The MRI agent of claim 1, wherein the nucleotide sequence is selected from the group consisting of SEQ ID NO: 9, SEQ ID NO: 10, SEQ ID NO: 11, SEQ ID NO: 12, SEQ ID NO: 13, SEQ ID NO: 14, and SEQ ID NO: 15.

4. The MRI agent of claim 2, wherein the contrast agent is a toxic T1 agent containing a member selected from the group consisting of gadolinium ($Gd^{3+}$), dysprosium ($Dy^{3+}$), lanthanide ($Ln^{3+}$), and a paracest imaging agent.

5. The MRI agent of claim 3, wherein the contrast agent is a toxic T1 agent containing a member selected from the group consisting of $Gd^{3+}$, $Dy^{3+}$, $Ln^{3+}$, and a paracest imaging agent.

6. The MRI agent of claim 2, wherein the contrast agent is a T2 agent that contains a superparamagnetic iron oxide nanoparticle (SPION).

7. The MRI agent of claim 3, wherein the contrast agent is a T2 agent that contains a SPION.

8. The MRI agent of claim 1, wherein the contrast agent contains a SPION and a toxic agent selected from the group consisting of $Gd^{3+}$, $Dy^{3+}$, $Ln^{3+}$, and a paracest imaging agent.

9. A method for treating an HIV infection in a subject, the method comprising administering to the subject in need thereof an MRI agent containing a toxic T1 contrast agent linked to a single stranded sODN including a nucleotide sequence that binds specifically to an HIV nucleic acid sequence, wherein the nucleotide sequence is selected from the group consisting of SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 9, SEQ ID NO: 10, SEQ ID NO: 11, SEQ ID NO: 12, SEQ ID NO: 13, SEQ ID NO: 14, and SEQ ID NO: 15.

10. The method of claim 9, wherein the nucleotide sequence is selected from the group consisting of SEQ ID NO: 9, SEQ ID NO: 10, SEQ ID NO: 11, SEQ ID NO: 12, SEQ ID NO: 13, SEQ ID NO: 14, and SEQ ID NO: 15.

11. The method of claim 9, wherein the HIV infection is a latent infection and the nucleotide sequence is selected from the group consisting of SEQ ID NO: 51, SEQ ID NO: 52, SEQ ID NO: 53, SEQ ID NO: 54, SEQ ID NO: 55, SEQ ID NO: 56, and SEQ ID NO: 57.

12. A method for detecting an HIV infection in a subject, the method comprising
administering to the subject an MRI agent containing a T2 contrast agent linked to a single stranded sODN that includes a nucleotide sequence that binds specifically to an HIV nucleic acid sequence, and
obtaining an MRI image of the subject after administering the MRI agent, wherein the nucleotide sequence is selected from the group consisting of SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 9, SEQ ID NO: 10, SEQ ID NO: 11, SEQ ID NO: 12, SEQ ID NO: 13, SEQ ID NO: 14, and SEQ ID NO: 15.

13. The method of claim 12, wherein the HIV infection is a latent infection.

14. The MRI agent of claim 8, wherein the nucleotide sequence is selected from the group consisting of SEQ ID NO: 9, SEQ ID NO: 10, SEQ ID NO: 11, SEQ ID NO: 12, SEQ ID NO: 13, SEQ ID NO: 14, and SEQ ID NO: 15.

* * * * *